(12) United States Patent
Lee et al.

(10) Patent No.: US 12,358,961 B2
(45) Date of Patent: Jul. 15, 2025

(54) METHODS OF TREATING SPINAL CORD INJURY USING A SUPRESSOR OF CYTOKINE SIGNALING-3 (SOCS3) REDUCTION PEPTIDE (SRP) COMPRISING A CELL MEMBRANE PENETRATING DOMAIN, A SOCS3 BINDING DOMAIN, AND A LYSOSOME TARGETING DOMAIN

(71) Applicant: The Cleveland Clinic Foundation, Cleveland, OH (US)

(72) Inventors: Yu-Shang Lee, Solon, OH (US); Ching-Yi Lin, Solon, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 40 days.

(21) Appl. No.: 18/159,483

(22) Filed: Jan. 25, 2023

(65) Prior Publication Data
US 2023/0303644 A1  Sep. 28, 2023

Related U.S. Application Data

(60) Division of application No. 17/137,875, filed on Dec. 30, 2020, now Pat. No. 11,981,711, which is a
(Continued)

(51) Int. Cl.
| | |
|---|---|
| *A61K 38/00* | (2006.01) |
| *A61K 9/00* | (2006.01) |
| *A61K 31/727* | (2006.01) |
| *A61K 38/17* | (2006.01) |
| *A61K 38/18* | (2006.01) |
| *A61K 49/00* | (2006.01) |
| *A61P 25/00* | (2006.01) |
| *A61P 25/28* | (2006.01) |
| *C07K 14/00* | (2006.01) |
| *C07K 14/47* | (2006.01) |
| *C07K 14/475* | (2006.01) |
| *C07K 14/48* | (2006.01) |
| *C07K 19/00* | (2006.01) |
| *A61K 31/737* | (2006.01) |
| *A61K 38/16* | (2006.01) |
| *A61K 38/39* | (2006.01) |
| *A61K 39/00* | (2006.01) |

(Continued)

(52) U.S. Cl.
CPC ........ *C07K 14/4703* (2013.01); *A61K 9/0019* (2013.01); *A61K 31/727* (2013.01); *A61P 25/00* (2018.01); *A61P 25/28* (2018.01); *C07K 19/00* (2013.01); *A61K 31/737* (2013.01); *A61K 38/00* (2013.01); *A61K 38/16* (2013.01); *A61K 38/1709* (2013.01); *A61K 38/39* (2013.01); *A61K 2039/55516* (2013.01); *A61K 2039/6031* (2013.01); *A61K 47/42* (2013.01); *A61K 47/64* (2017.08); *A61K 47/645* (2017.08); *A61K 48/005* (2013.01); *A61K 49/0056* (2013.01); *A61K 49/14* (2013.01); *A61K 2121/00* (2013.01); *A61K 2300/00* (2013.01); *A61L 27/22* (2013.01); *A61L 2300/236* (2013.01); *A61L 2300/252* (2013.01); *A61L 2430/32* (2013.01); *A61P 17/02* (2018.01); *C07K 2319/03* (2013.01); *C07K 2319/70* (2013.01); *C07K 2319/95* (2013.01); *G01N 33/5058* (2013.01); *G01N 33/68* (2013.01)

(58) Field of Classification Search
CPC .. A61K 38/00; A61K 38/1709; A61K 38/177; A61K 2039/55516; A61K 2039/6031; A61K 38/16; C07K 2319/70; C07K 14/00; C07K 14/73; C07K 2319/31; C07K 2319/71; C07K 2319/95; C07K 2319/06; C07K 2319/10; C07K 2319/00; C07K 2317/77; C07K 2319/03; A61P 25/28; A61P 25/00; A61P 29/00
See application file for complete search history.

(56) References Cited

U.S. PATENT DOCUMENTS

| | | | | |
|---|---|---|---|---|
| 6,664,374 | B1 * | 12/2003 | Saxinger | C07K 14/7155 530/328 |
| 7,144,986 | B2 * | 12/2006 | Saxinger | C07K 14/7155 530/323 |

(Continued)

FOREIGN PATENT DOCUMENTS

| | | | |
|---|---|---|---|
| WO | 0166128 A1 | 9/2001 | |
| WO | WO-2006031330 A2 * | 3/2006 | ............ A61K 38/07 |

(Continued)

OTHER PUBLICATIONS

Stadelman et al., Biochimica Biophy. Acta, 2011; 1812:275-282.*

(Continued)

*Primary Examiner* — Chang-Yu Wang
(74) *Attorney, Agent, or Firm* — Jason R. Bond; Casimir Jones, S.C.

(57) ABSTRACT

Provided herein are compositions, systems, kits, and methods for treating nervous system injuries caused by trauma or neurodegeneration or aging in a subject by administering a CSPG or SOCS3 reduction peptide (CRP and SRP respectively), or a nucleic acid sequence encoding the CRP or SRP, wherein both the CRP and SRP comprise a cell membrane penetrating domain, and a lysosome targeting domain, and the CRP further comprises a chondroitin sulfate proteoglycan (CSPG) binding domain, and the SRP further comprises a suppressor of cytokine signaling-3 (SOCS3) binding domain.

7 Claims, 40 Drawing Sheets

Specification includes a Sequence Listing.

Related U.S. Application Data continuation of application No. 16/626,940, filed as application No. PCT/US2018/039539 on Jun. 26, 2018, now Pat. No. 10,906,949.

(60) Provisional application No. 62/526,160, filed on Jun. 28, 2017.

(51) Int. Cl.

| | | |
|---|---|---|
| A61K 47/42 | (2017.01) | |
| A61K 47/64 | (2017.01) | |
| A61K 48/00 | (2006.01) | |
| A61K 49/14 | (2006.01) | |
| A61L 27/22 | (2006.01) | |
| A61P 17/02 | (2006.01) | |
| G01N 33/50 | (2006.01) | |
| G01N 33/68 | (2006.01) | |

(56) References Cited

U.S. PATENT DOCUMENTS

| | | | |
|---|---|---|---|
| 7,256,007 B2* | 8/2007 | Nicholson | A61P 37/06 435/7.8 |
| 8,207,316 B1 | 6/2012 | Bentwich | |
| 8,420,096 B2* | 4/2013 | Hawiger | A61P 3/10 514/2.7 |
| 9,744,188 B2* | 8/2017 | Flanagan | A61P 25/00 |
| 10,287,333 B2* | 5/2019 | Wang | A61P 25/28 |
| 10,323,063 B2* | 6/2019 | Jo | C07K 7/08 |
| 10,323,072 B2* | 6/2019 | Jo | C07K 7/08 |
| 10,385,103 B2* | 8/2019 | Jo | C07K 14/4703 |
| 10,689,424 B2* | 6/2020 | Jo | A61P 3/00 |
| 10,781,241 B2* | 9/2020 | Jo | A61K 38/1761 |
| 10,787,492 B2* | 9/2020 | Jo | C07K 7/08 |
| 10,961,292 B2* | 3/2021 | Jo | A61K 38/1761 |
| 10,975,132 B2* | 4/2021 | Jo | C07K 14/4703 |
| 11,186,620 B2* | 11/2021 | Wang | C12Y 207/11001 |
| 11,274,129 B2* | 3/2022 | Li | G01N 33/574 |
| 2002/0177207 A1 | 11/2002 | Sugiyama et al. | |
| 2004/0029114 A1 | 2/2004 | Mack et al. | |
| 2004/0156826 A1 | 8/2004 | Dangond et al. | |
| 2005/0222029 A1 | 10/2005 | Bartel et al. | |
| 2007/0065415 A1 | 3/2007 | Kleinsek et al. | |
| 2007/0276126 A1 | 11/2007 | Elliott et al. | |
| 2009/0082265 A1 | 3/2009 | Bartel et al. | |
| 2009/0169573 A1 | 7/2009 | Schultz et al. | |
| 2013/0065267 A1 | 3/2013 | Mao | |
| 2014/0045762 A1* | 2/2014 | Flanagan | A61K 38/177 514/17.7 |
| 2015/0266935 A1* | 9/2015 | Wang | A61K 9/00 514/17.7 |
| 2015/0299687 A1 | 10/2015 | Gruskin et al. | |
| 2017/0137482 A1* | 5/2017 | Jo | C07K 14/4703 |
| 2018/0051060 A1* | 2/2018 | Jo | C07K 14/51 |
| 2018/0327462 A1 | 11/2018 | Matouschek | |
| 2019/0040378 A1 | 2/2019 | Fotin-Mleczek et al. | |
| 2019/0160146 A1* | 5/2019 | Shen | A61K 38/12 |
| 2019/0211070 A1 | 7/2019 | Wang | |

FOREIGN PATENT DOCUMENTS

| | | | | |
|---|---|---|---|---|
| WO | WO-2006045750 A2 * | 5/2006 | | C07K 14/4748 |
| WO | WO-2012112953 A2 * | 8/2012 | | A61K 31/727 |
| WO | WO-2014047741 A1 * | 4/2014 | | A61K 31/00 |
| WO | 2015112904 A1 | 7/2015 | | |
| WO | WO 2017/079723 | 5/2017 | | |
| WO | WO-2017197253 A2 * | 11/2017 | | A61K 38/10 |

OTHER PUBLICATIONS

Abraham, Spinal Cord Injury, Trauma Reports, Nov. 1, 2016.*
The Initial Management of Closed Head Injury from Ministry of Health, NSW, published Feb. 8, 2012.*
Alaoui-Ismaili et al., Design of second generation therapeutic recombinant bone morphogenetic proteins. Cytokine Growth Factor Rev. Oct.-Dec. 2009;20(5-6):501-7.
Anger, Animal test systems to study behavioral dysfunctions of neurodegenerative disorders. Neurotoxicology. Fall 1991;12(3):403-13.
Aricescu et al., Heparan Sulfate Proteoglycans Are Ligands for Receptor Protein Tyrosine Phosphatase sigma. Mol Cell Biol. Mar. 2002;22(6):1881-92.
Atwood et al., A Unified Hypothesis of Early- and Late-Onset Alzheimer's Disease Pathogenesis. J Alzheimers Dis. 2015;47(1):33-47.
Blight, Miracles and molecules—progress in spinal cord repair. Nat Neurosci. Nov. 2002;5 Suppl:1051-4.
Bowie et al., Deciphering the message in protein sequences: tolerance to amino acid substitutions. Science. Mar. 16, 1990;247(4948):1306-10.
Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
Djerbal et al., Chondroitin sulfates and their binding molecules in the central nervous system. Glycoconj J. Jun. 2017;34(3):363-376.
Falkenburger et al., Limitations of cellular models in Parkinson's disease research. J Neural Transm Suppl. 2006;(70):261-8.
Guo et al., Protein tolerance to random amino acid change. Proc Natl Acad Sci U S A. Jun. 22, 2004;101(25):9205-10.
Henstridge et al., Beyond the neuron-cellular interactions early in Alzheimer disease pathogenesis. Nat Rev Neurosci. Feb. 2019;20(2):94-108.
Hoke et al., Mechanisms of Disease: what factors limit the success of peripheral nerve regeneration in humans? Nat Clin Pract Neurol. Aug. 2006;2(8):448-54.
Jagmag et al., Evaluation of Models of Parkinson's Disease. Front Neurosci. Jan. 19, 2016;9:503.
Keough et al., An Inhibitor of Chondroitin Sulfate Proteoglycan Synthesis Promotes Central Nervous System Remyelination. at Commun . Apr. 26, 2016;7:11312.
Lang et al., Modulation of the proteoglycan receptor PTPσ promotes recovery after spinal cord injury. Nature. Feb. 19, 2015;518(7539):404-8.
Moore et al., Molecular pathophysiology of Parkinson's disease. Annu Rev Neurosci. 2005;28:57-87.
Pawson et al., Assembly of cell regulatory systems through protein interaction domains. Science. Apr. 18, 2003;300(5618):445-52.
Potashkin et al., Limitations of animal models of Parkinson's disease. Parkinsons Dis. Dec. 20, 2010;2011:658083.
Sarter, Animal cognition: defining the issues. Neurosci Biobehav Rev. Nov. 2004;28(7):645-50.
Schmidt et al., Neural tissue engineering: strategies for repair and regeneration. Annu Rev Biomed Eng. 2003;5:293-347.
Shen et al., PTPsigma Is a Receptor for Chondroitin Sulfate Proteoglycan, an Inhibitor of Neural Regeneration. Science. Oct. 23, 2009;326(5952):592-6.
Swerdlow, Pathogenesis of Alzheimer's disease. Clin Interv Aging. 2007;2(3):347-59.
T' Hart et al., The use of animal models to investigate the pathogenesis of neuroinflammatory disorders of the central nervous system. Curr Opin Neurol. Jun. 2003;16(3):375-83.
Tayebati, Animal models of cognitive dysfunction. Mech Ageing Dev. Feb. 2006;127(2):100-8.
ISR and Written Opinion for PCT/US2018/039539 mailed Nov. 19, 2018, 14 pages.
Extended EP Search Report for EP18823329.0, mailed Jun. 11, 2021, 12 pages.
European Search Report for European Application No. 24205892.3, mailed May 27, 2025, 11 Pages.
International Preliminary Report on Patentability for International Application No. PCT/US2018/039539, mailed Jan. 9, 2020, 7 Pages.

(56) References Cited

OTHER PUBLICATIONS

Jin J.W., et al., "Development of an Alpha-synuclein Knockdown Peptide and Evaluation of Its Efficacy in Parkinson's Disease Models", Communications Biology, 2021, vol. 4, No. 1, pp. 1-15.

Madonna S., et al., "SOCS3 Inhibits the Pathological Effects of IL-22 in Non-melanoma Skin Tumor-derived Keratinocytes", Oncotarget, vol. 8, No. 15, Feb. 22, 2017, p. 24652-24667, XP093249074, United States, ISSN: 1949-2553, DOI: 10.18632/oncotarget. 15629, abstract, table 1.

Park K.W., et al., "Effects of Reducing Suppressors of Cytokine Signaling-3 (SOCS3) Expression on Dendritic Outgrowth and Demyelination after Spinal Cord Injury", PLOS One, vol. 10, No. 9, Sep. 18, 2015, e0138301, XP055778921, pp. 1-19, DOI: 10.1371/journal.pone.0138301, abstract, figure 2.

Partial Supplementary European Search Report for European Application No. 18823329.0, mailed Mar. 11, 2021, 12 Pages.

\* cited by examiner

FIG. 2
Experimental Design
1. Sub-acute treatment of CRP:
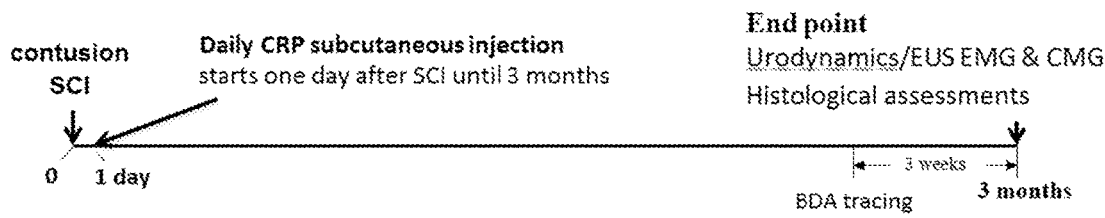
2. Chronic treatment of CRP:
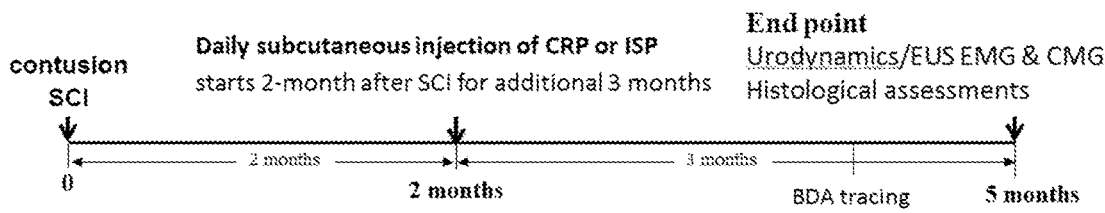
BBB locomotion test: once a week after SCI
Voiding pattern test by metabolic cage: every two weeks after SCI CRP improves voiding patterns after SCI
-- Assessment by metabolic cage CRP improves bladder function after SCI
-- Assessment by Urodynamic analyses CRP treatment reduces residual volume and volume per void toward normal condition

CRP improves bladder function after SCI

-- Assessment by Urodynamic analyses

CRP treatment reduces overactive bladder by the reduction of both the number and the amplitude of non-voiding contraction CRP enhances nerve sprouting below lesion from neurons in brain stem and red nuclei after SCI FIG. 19A
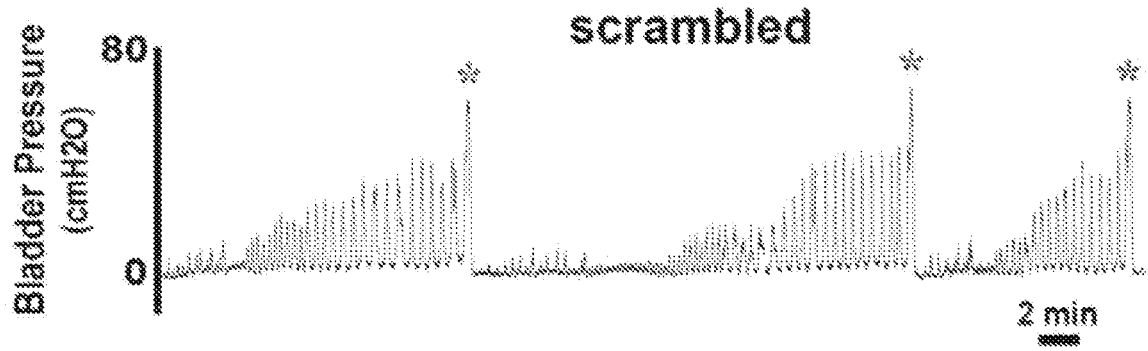
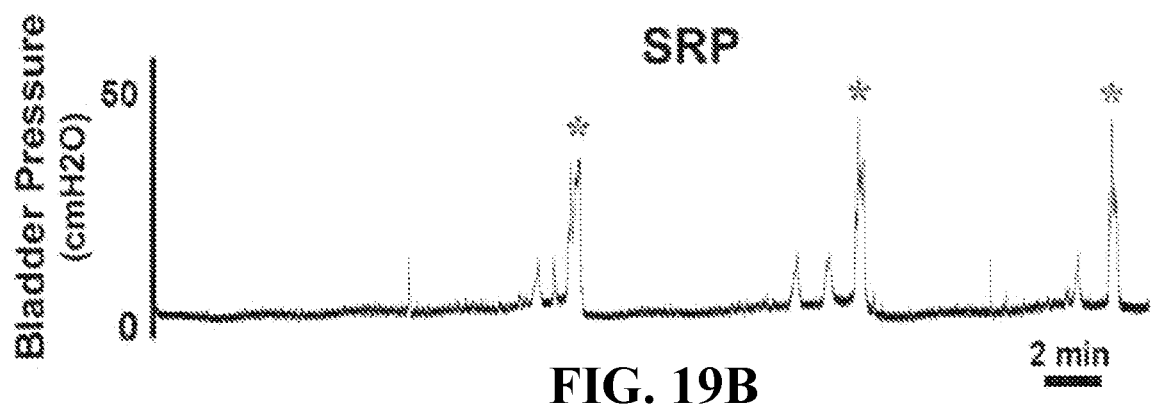
FIG. 19B
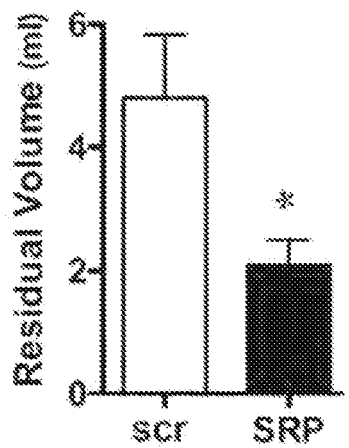
FIG. 19C
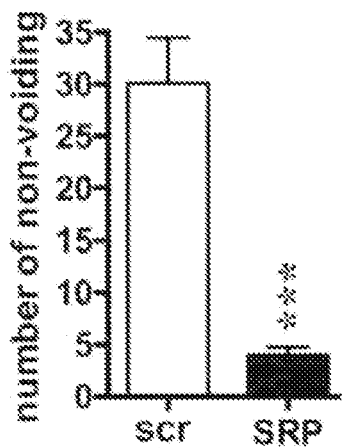
FIG. 19D
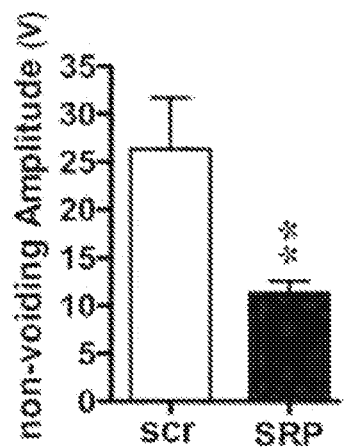
FIG. 19E

FIG. 20
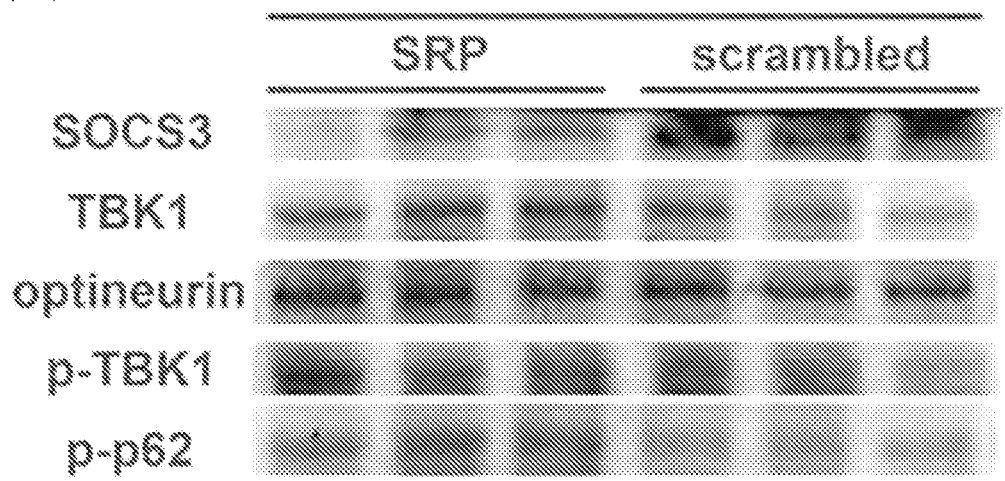
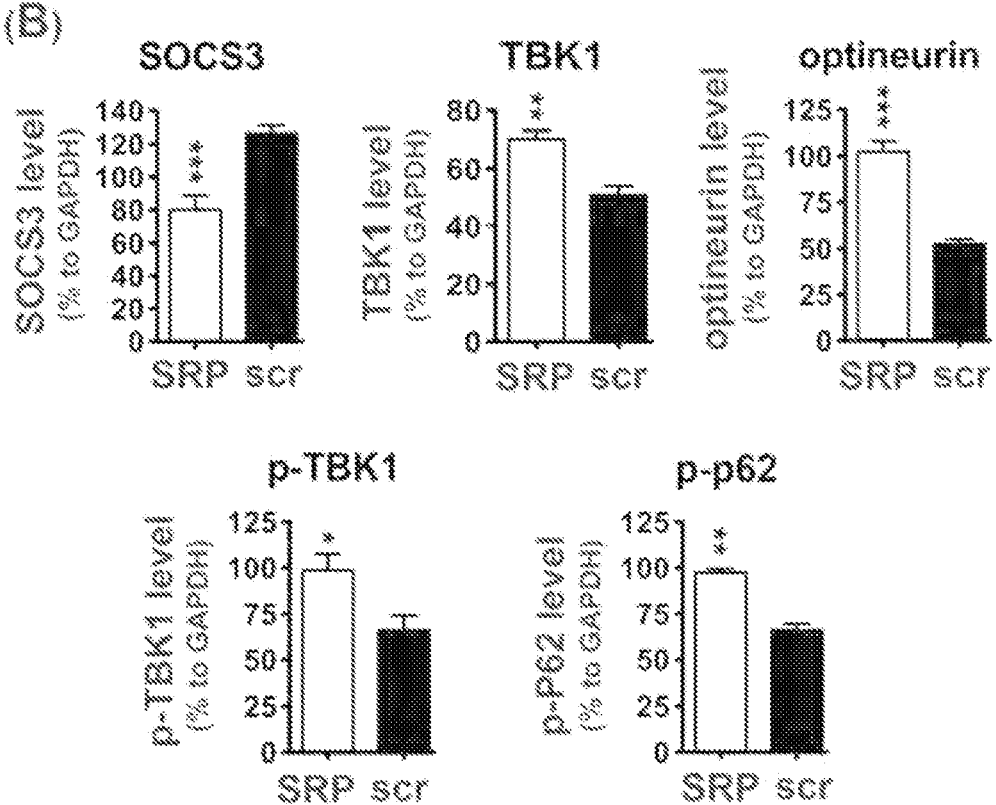

FIG. 24
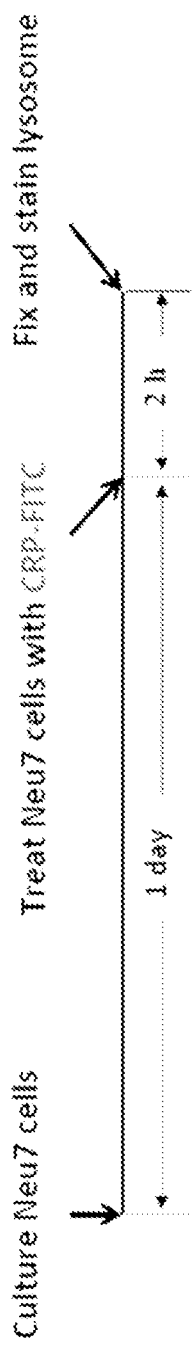 

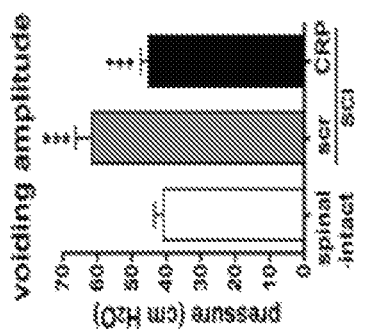
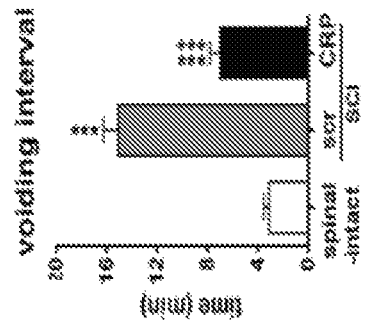
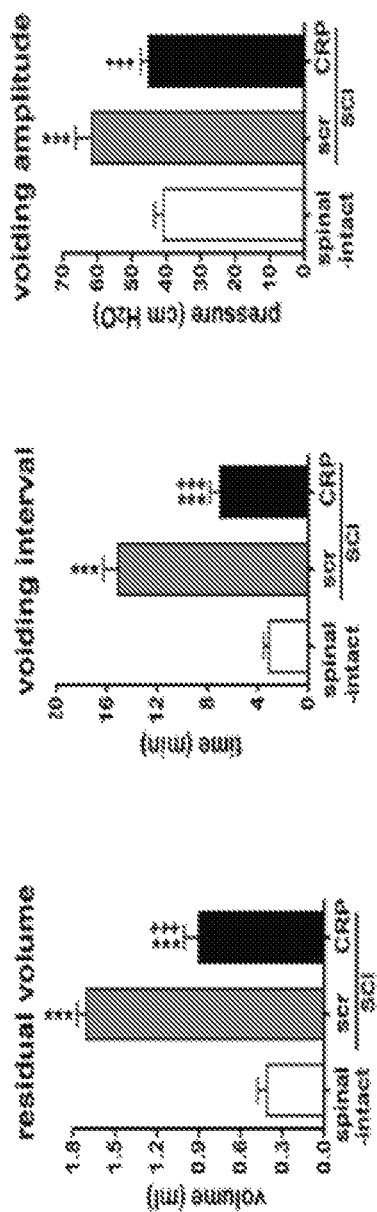
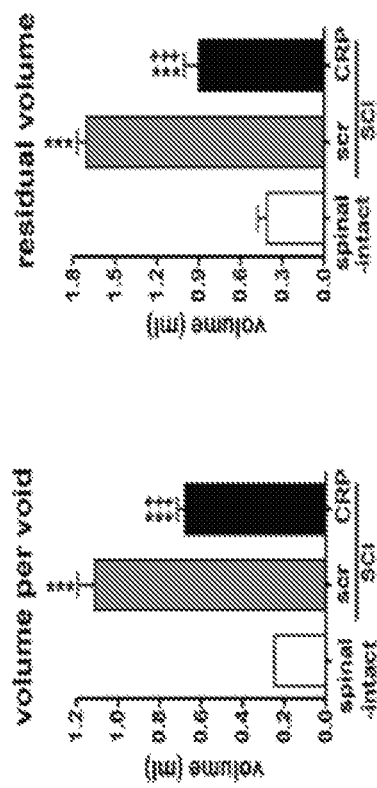
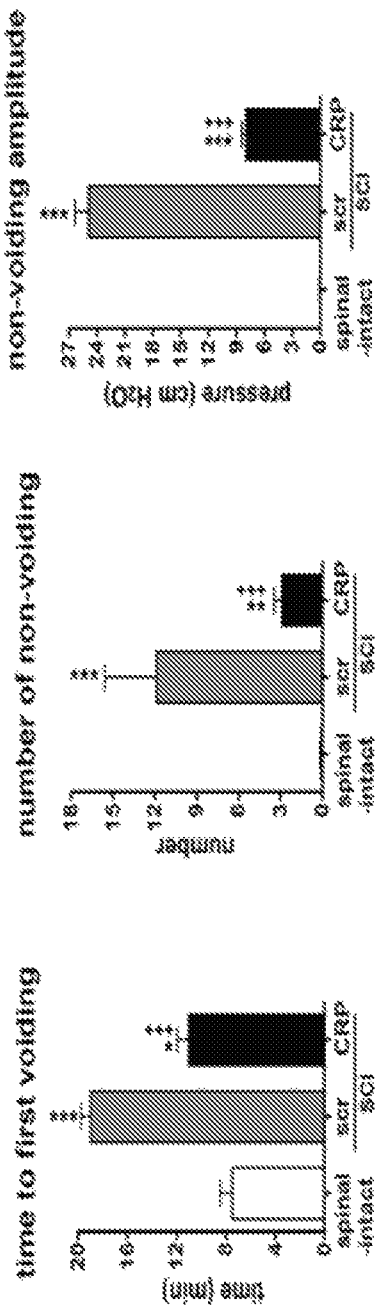
FIG. 27E, FIG. 27D, FIG. 27C, FIG. 27B, FIG. 27H, FIG. 27G, FIG. 27F

FIG. 35
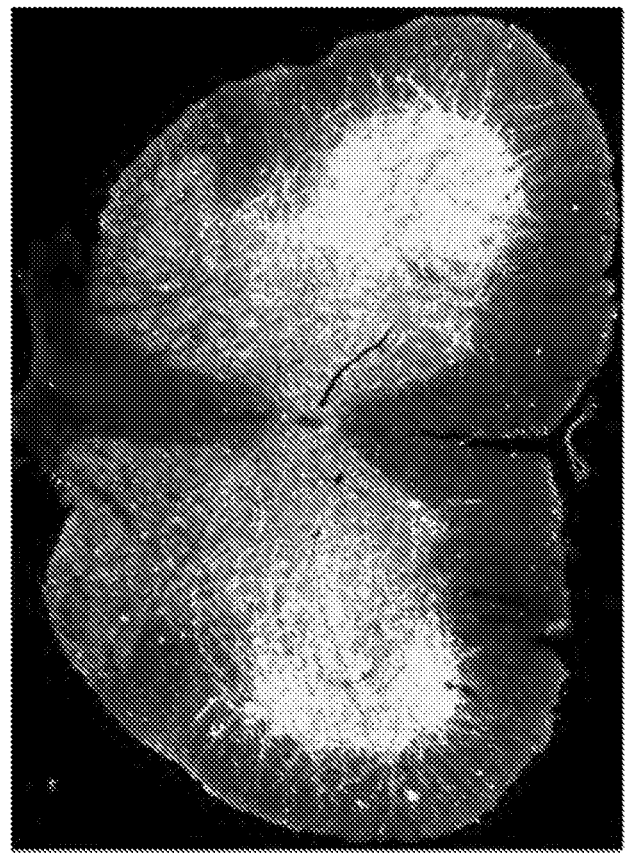
CRP
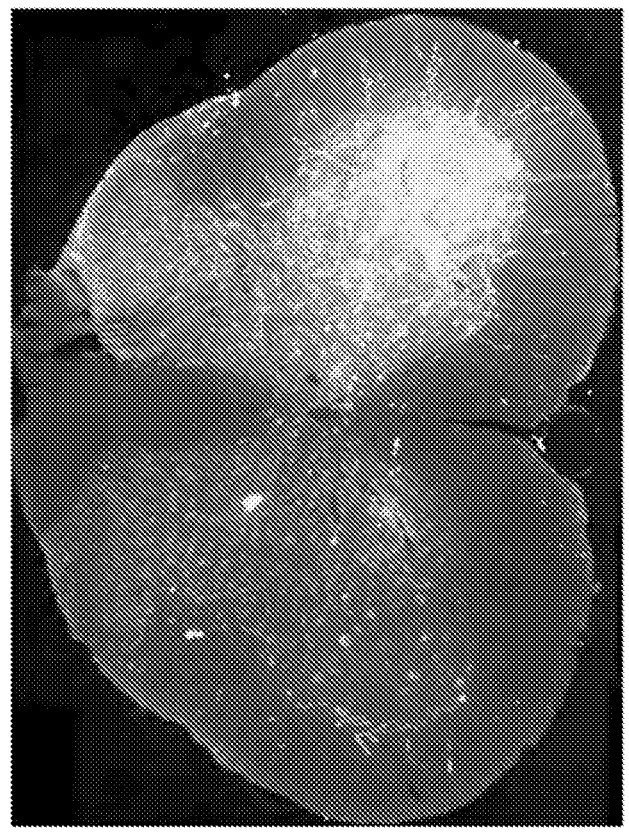
scrambled peptide

METHODS OF TREATING SPINAL CORD INJURY USING A SUPRESSOR OF CYTOKINE SIGNALING-3 (SOCS3) REDUCTION PEPTIDE (SRP) COMPRISING A CELL MEMBRANE PENETRATING DOMAIN, A SOCS3 BINDING DOMAIN, AND A LYSOSOME TARGETING DOMAIN

CROSS REFERENCE TO RELATED APPLICATIONS

The present application is a continuation of U.S. patent application Ser. No. 17/137,875, filed on Dec. 30, 2020, which is a continuation of U.S. patent application Ser. No. 16/626,940 filed on Dec. 27, 2019, now U.S. Pat. No. 10,906,949, which is a § 371 U.S. National Entry Application of PCT/US2018/039539, which claims priority to U.S. Provisional application Ser. No. 62/526,160 filed Jun. 28, 2017, each of which is herein incorporated by reference in its entirety.

SEQUENCE LISTING

The text of the computer readable sequence listing filed herewith, titled "35302-404_SEQUENCE_LISTING", created Jan. 25, 2023, having a file size of 79,254 bytes, is hereby incorporated by reference in its entirety.

FIELD

Provided herein are compositions, systems, kits, and methods for treating nervous system injuries caused by trauma or neurodegeneration or aging in a subject by administering a CSPG or SOCS3 reduction peptide (CRP and SRP respectively), or a nucleic acid sequence encoding the CRP or SRP, wherein both the CRP and SRP comprise a cell membrane penetrating domain, and a lysosome targeting domain, and the CRP further comprises a chondroitin sulfate proteoglycan (CSPG) binding domain, and the SRP further comprises a suppressor of cytokine signaling-3 (SOCS3) binding domain.

BACKGROUND

There is a huge market desire to remove scares caused by trauma and/or neurodegeneration to facilitate nerve regrowth and to enhance functional outcomes in both Peripheral Nervous System (PNS) and Central Nervous System (CNS) clinically. There is currently no intervention available clinically to target the spinal cord injury (SCI) and to address its associated neurological disorders including bladder control. The patients with SCI in the U.S. have been estimated to be approximately 276,000 people, with a range from 240,000 to 337,000 persons in 2014. The new cases are about 13,000 per year. The bladder function is a high priority that patients with SCI would like to be returned.

There are two major approaches applied in experiments to reduce chondroitin sulfate proteoglycan (CSPG, the major component of scarring) are bacterial enzyme chondroitinase ABC and Lentiviral delivery of chondroitinase ABC. However, both chondroitinase ABC and Lentiviral delivery of chondroitinase ABC have only limited efficacy and are not clinically applicable. Chondroitinase ABC has low thermal stability, short longevity and must be applied locally. These disadvantages limit its efficacy and clinical application. Lentiviral delivery of chondroitinase ABC has a relatively low transfection rate, and biological safety concerns. In addition, Lentivirus needs to be applied about two weeks before injury/trauma. The timing and amount applied cannot be controlled. All of these disadvantages limit efficacy and clinical application of Lentiviral delivery of chondroitinase ABC.

Another newly published peptide, intracellular sigma peptide (ISP), was originally designed to interfere the function of one of the receptors of CSPG (i.e. PTPG) in order to block the inhibitory effects of CSPG, but has no effects on CSPG itself in vivo. While ISP when applied immediately after SCI in rats has been reported to have minor effects on promoting functional recovery after SCI, the underlying mechanisms are still unknown even after extensive investigation for years. The most critical disadvantage of ISP is that ISP has no effects on chronic SCI when ISP was applied two-month after SCI. Such disadvantages and the unknown mechanisms underlying its published effects significantly limit the efficacy and clinical application of ISP.

SUMMARY

Provided herein are compositions, systems, kits, and methods for treating nervous system injuries caused by trauma or neurodegeneration or aging in a subject by administering a CSPG or SOCS3 reduction peptide (CRP and SRP respectively), or a nucleic acid sequence encoding the CRP or SRP, wherein both the CRP and SRP comprise a cell membrane penetrating domain, and a lysosome targeting domain, and the CRP further comprises a chondroitin sulfate proteoglycan (CSPG) binding domain, and the SRP further comprises a SOCS3 binding domain.

In certain embodiments, provided herein are methods of treating nervous system injury or trauma or degeneration or aging (e.g., advanced years, such as over 75 years old) in a subject comprising: administering a CSPG reduction peptide (CRP), or a nucleic acid sequence encoding the CRP, to a subject with a nervous system injury or trauma or degeneration or aging, wherein the CRP comprises: i) a first amino acid sequence encoding a cell membrane penetrating domain, ii) a second amino acid sequence encoding a chondroitin sulfate proteoglycan (CSPG) binding domain, and iii) a third amino acid sequence encoding a lysosome targeting domain.

In some embodiments, the nervous system injury or trauma or degeneration or aging is localized to at least one nervous system site on the subject (e.g., particular location between certain vertebrate on the spinal cord). In other embodiments, the administering is under conditions such that the CRP reduces the level of CSPG present at the at least one nervous system site (e.g., one site, two sites, three sites, etc.). In other embodiments, the nervous system site is in the spinal cord of the subject. In other embodiments, the nervous system site is in the degenerated brain and/or spinal cord of the subject. In further embodiments, the nervous system injury or trauma or degeneration or aging is to the subject's central nervous system (CNS). In some embodiments, the nervous system injury or trauma or degeneration or aging is to the subject's peripheral nervous system (PNS).

In certain embodiments, administering is conducted within about 24 hours of the nervous system injury or trauma or degeneration or aging (e.g., within 1 hour . . . 5 hours . . . 15 hours . . . 20 hours, or within 24 hours). In some embodiments, the administering is conducted after at least two days of the nervous system injury or trauma or degeneration or aging (e.g., after 2 days . . . 4 days . . . or 6 days). In other embodiments, the administering is conducted at least one week after the nervous system injury or trauma or degeneration or aging (e.g., after 7 days . . . 15 days . . . or 25 days). In further embodiments, the administering is conducted at least one month after the nervous system injury or trauma or degeneration or aging (e.g., at least one month or 1.5 months). In additional embodiments, the administering is conducted at least two months after nervous system injury or trauma or degeneration or aging (e.g., at least 2 months . . . 5 months . . . 1 year . . . 2 years . . . or 5 years after the injury or trauma).

In certain embodiments, provided herein are methods of treating multiple sclerosis (MS), or aiding in limb transplant, in a subject comprising: administering a CSPG reduction peptide (CRP), or a nucleic acid sequence encoding the CRP, to a subject with MS (or other neurological condition) or undergoing limb transplant, wherein the CRP comprises: i) a first amino acid sequence encoding a cell membrane penetrating domain, ii) a second amino acid sequence encoding a chondroitin sulfate proteoglycan (CSPG) binding domain, and iii) a third amino acid sequence encoding a lysosome targeting domain.

In some embodiments, provided herein are compositions, systems, and kits comprising: a CSPG reduction peptide (CRP) (e.g., to reduce scars), or a nucleic acid sequence encoding the CRP, wherein the CRP comprises: a) a first amino acid sequence encoding a cell membrane penetrating domain, b) a second amino acid sequence encoding a chondroitin sulfate proteoglycan (CSPG) binding domain, and c) a third amino acid sequence encoding a lysosome targeting domain. In particular embodiments, the compositions, systems, further comprise a device for injecting a composition comprising the CRP into a subject's nervous system.

In particular embodiments, the first amino acid sequence is located at the N-terminal or C-terminal of the CRP. In other embodiments, the third amino acid sequence is located at the N-terminal or C-terminal of the CRP. In additional embodiments, the second amino acid sequence is located between the first and third amino acid sequences. In further embodiments, the first amino acid sequence comprises or consists of an amino acid sequence shown in SEQ ID NOS: 1 and 5-27, or a sequence with one amino acid addition, subtraction or substitution. In additional embodiments, the third amino acid sequence comprises or consists of an amino acid sequence shown in SEQ ID NOS: 3 or 28-36, or a sequence with one amino acid addition, subtraction or substitution. In additional embodiments, the second amino acid sequence comprises or consists of an amino acid sequence shown in SEQ ID NO: 2 or 37-53, or a sequence with one amino acid addition, subtraction or substitution.

In certain embodiments, provided herein are methods of treating nervous system injury or trauma or degeneration or aging (e.g., older than 75 . . . 85 . . . or 95) in a subject comprising: administering a SOCS3 reduction peptide (SRP), or a nucleic acid sequence encoding the SRP, to a subject with a nervous system injury or trauma or degeneration or aging, wherein the SRP comprises: i) a first amino acid sequence encoding a cell membrane penetrating domain, ii) a second amino acid sequence encoding a Suppressor of cytokine signaling 3 (SOCS3) binding domain, and iii) a third amino acid sequence encoding a lysosome targeting domain.

In some embodiments, the nervous system injury or trauma or degeneration or aging is localized to at least one nervous system site on the subject (e.g., particular location between certain vertebrate on the spinal cord). In other embodiments, the administering is under conditions such that the SRP reduces the level of SOCS3 present at the at least one nervous system site (e.g., one site, two sites, three sites, etc.). In other embodiments, the nervous system site is in the spinal cord of the subject. In other embodiments, the nervous system site is in the degenerated brain and/or spinal cord of the subject. In further embodiments, the nervous system injury or trauma or degeneration or aging is to the subject's central nervous system (CNS). In some embodiments, the nervous system injury or trauma or degeneration or aging is to the subject's peripheral nervous system (PNS).

In certain embodiments, administering is conducted within about 24 hours of the nervous system injury or trauma or degeneration or aging (e.g., within 1 hour . . . 5 hours . . . 15 hours . . . 20 hours, or within 24 hours). In some embodiments, the administering is conducted after at least two days of the nervous system injury or trauma or degeneration or aging (e.g., after 2 days . . . 4 days . . . or 6 days). In other embodiments, the administering is conducted at least one week after the nervous system injury or trauma or degeneration or aging (e.g., after 7 days . . . 15 days . . . or 25 days). In further embodiments, the administering is conducted at least one month after the nervous system injury or trauma or degeneration or aging (e.g., at least one month or 1.5 months). In additional embodiments, the administering is conducted at least two months after nervous system injury or trauma or degeneration or aging (e.g., at least 2 months . . . 5 months . . . 1 year . . . 2 years . . . or 5 years after the injury or trauma).

In certain embodiments, provided herein are methods of treating multiple sclerosis, motor neuron disease (MND), ALS, or aiding in limb transplant, in a subject comprising: administering a SOCS3 reduction peptide (SRP), or a nucleic acid sequence encoding the SRP, to a subject with MND (or other neurological condition) or undergoing limb transplant, wherein the SRP comprises: i) a first amino acid sequence encoding a cell membrane penetrating domain, ii) a second amino acid sequence encoding SOCS3 binding domain, and iii) a third amino acid sequence encoding a lysosome targeting domain.

In some embodiments, provided herein are compositions, systems, and kits comprising: a SOCS3 reduction peptide (SRP) (e.g., to reduce scars), or a nucleic acid sequence encoding the SRP, wherein the SRP comprises: a) a first amino acid sequence encoding a cell membrane penetrating domain, b) a second amino acid sequence encoding a SOCS3 binding domain, and c) a third amino acid sequence encoding a lysosome targeting domain. In particular embodiments, the compositions, systems, further comprise a device for injecting a composition comprising the SRP into a subject's nervous system.

In particular embodiments, the first amino acid sequence is located at the N-terminal or C-terminal of the SRP. In other embodiments, the third amino acid sequence is located at the N-terminal or C-terminal of the SRP. In additional embodiments, the second amino acid sequence is located between the first and third amino acid sequences. In further embodiments, the first amino acid sequence comprises or consists of an amino acid sequence shown in SEQ ID NOS: 1 and 5-27, or a sequence with one amino acid addition, subtraction or substitution. In additional embodiments, the third amino acid sequence comprises or consists of an amino acid sequence shown in SEQ ID NOS: 3 or 28-36, or a sequence with one amino acid addition, subtraction or substitution. In additional embodiments, the second amino acid sequence comprises or consists of an amino acid sequence shown in SEQ ID NO: 54-89, or a sequence with one amino acid addition, subtraction or substitution.

DESCRIPTION OF THE FIGURES

FIG. 2 shows a schematic of the experimental design for in vivo testing when a CRP was applied sub-acutely (one-day after SCI) or chronically (two-month after SCI) in Example 1.

FIG. 19A-G show SRP treatment improved bladder function after T8 contusive SCI. Animals were treated daily with SRP for one month, beginning one day after SCI. Urodynamic analyses were conducted 3 months post-SCI. A representative cystometrograms (CMG) of three cycles of micturition events (red * indicates where micturition occurred) shows hyperactive bladder activity before reaching the voiding point in scrambled peptide-treated animals (A). SRP treatment (SRP) significantly reduced bladder hyperactivity (B). Statistical analysis revealed that SRP significantly reduced (C) residual volume, (D) the number of non-voiding contractions, and (E) the non-voiding contraction amplitude when compared to the scrambled peptide group (scr). FIG. 19 (F and G) also shows SRP treatment improved bursting activities of external urethral sphincter (EUS) recorded by electromyogram (EMG) after T8 contusive SCI. EUS EMG recording were conducted 3 months post-SCI. The EUS EMG during the void period showed improvement in bursting activity indicated by red rectangle following SRP (G) when compared to the scrambled peptide (scrambled) group (F).

FIG. 20, panels A and B, shows that SRP significantly increased TBK1 and mitophagy adaptors in the spinal cord after SCI. SCI-upregulated SOCS3 was significantly reduced by SRP treatment (SRP) beginning one day after SCI (once per day) compared to the scrambled peptide group (scr). The protein levels of TBK1 and optineurin were significantly increased with SRP treatment. Additionally, significant activation of TBK1 and p62, as indicated by phospho-TBK1 Ser172 (p-TBK1) and phosphor-p62 Ser403 (p-p62) expression, was observed in SRP-treated SCI animals. (A). Graphs represented mean±SEM of six samples per group for the % to GAPDH (B).

FIG. 24 shows that applied CRP is found in the lysosome of Neu7 astrocytes and provides the results of an in vitro assays that demonstrates the concept of lysosmoal target domain in CRP. Such an in vitro assay was used to demonstrate the co-localization of FITC-CRP and lysosomal marker (LAMP1). Representative images indicate that FITC-CRP is brought to lysosomes (LAMP1+) for degradation after entering Neu7 cells (arrow).

FIG. 25 shows that CRP significantly reduces CSPG produced by Neu7 cells to a comparable level what ChABC does. Note there is also a dosage response by CRP application.

FIG. 26 shows Kinematics assessment in SCI rats. (A) Representative total of hindlimb movement trajectories for spinal-intact, SCI+scrambled peptide (scr) and SCI+CRP groups at 3 months post-SCI. (B-G) CRP treatment significantly improved several parameters of gait pattern with trajectories more consistent to what the spinal-intact animals did, when compared to scr treatment.

FIGS. 27A-H show that CRP treatment improves bladder function after SCI. (A) Representative cystometrograms (CMG) with micturition (voiding) events (indicated by asterisk) for spinal-intact, SCI+scrambled peptide (scr) and SCI+CRP groups at 3 months post-SCI. (B~H) CRP treatment reduces hyperactive bladder and improve CMG parameters including lower voiding pressure and smaller bladder capacity when compared to scr application after T8 SCI.

FIG. 31 shows BBB scores that show that CRP treatment improves hindlimb locomotion after chronic SCI (N=6 to 8 animals per group). Note the significant increases in BBB locomotion scale by CRP at 5 months post SCI when compared to what at the time (two months post SCI) of beginning treatment.

FIG. 32 shows representative 2D trajectory patterns indicated CRP treatment improved stepping kinematic of both hindlimbs by CRP at 5 months post SCI when it compared to what at the time (two months post SCI) of beginning treatment.

FIG. 33 shows representative cystometrograms (CMG) data indicated 3 months of CRP treatment (starting at 2 months post SCI) can reduce hyperactive bladder and improve other CMG parameters.

FIG. 34 shows representative urodynamic and external urethral sphincter (EUS) electromyogram (EMG) recordings indicated CRP treatment can improve EUS bursting activity during the void period when compared to the scrambled peptide application after chronic SCI. The box area indicates the bursting activity.

FIG. 35 shows CRP enhances 5HT fibers sprouting in lumbar cord after chronic SCI. In particular, FIG. 35 shows representative spinal cord transverse images that CRP treatment can enhance 5HT+nerve fibers sprouting in lumbosacral level when compared to the scrambled peptide treatment after chronic SCI.

FIG. 36 shows 5HT immunoreactivity in lumbosacral level after chronic SCI. Representative spinal cord transverse images show that low amount of 5HT fibers found at L4 levels after contusive SCI, while CRP treatment significantly increases immunoreactivity of 5HT fibers. Representative images with double staining of WFA and 5HT shows areas with robustly decreased PNN (indicated by WFA+) but enhanced 5-HT sprouting.

FIG. 37 shows the acute treatment of CRP with allograft of a peripheral nerve segment (2 cm) improved the stepping performance of hindlimbs at 3 months after complete sciatic nerve transection. The representative 2D trajectory and improved kinematics parameters indicated CRP treated animals improved the stepping more toward to what the uninjured limb did, while compared to the vehicle treated animals. The CRP was delivered through subcutaneous injection near the injured site (once per day) staring immediately after surgery for 3 months.

DETAILED DESCRIPTION

Figure 1:
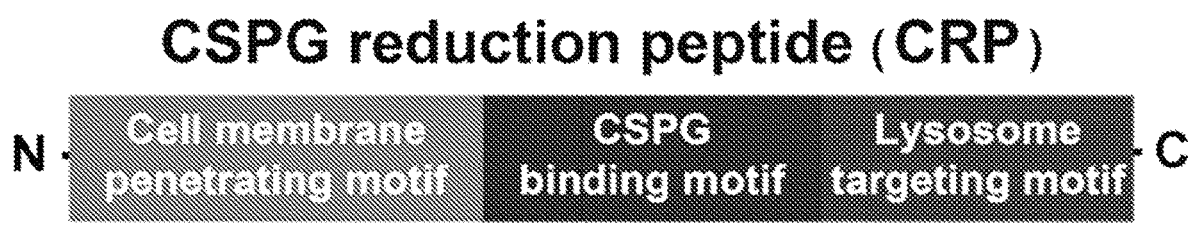
FIG. 1 shows a schematic of the exemplary CRP employed in Example 1.

Provided herein are compositions, systems, kits, and methods for treating nervous system injuries caused by trauma or neurodegeneration or aging in a subject by administering a CSPG or SOCS3 reduction peptide (CRP and SRP respectively), or a nucleic acid sequence encoding the CRP or SRP, wherein both the CRP and SRP comprise a cell membrane penetrating domain, and a lysosome targeting domain, and the CRP further comprises a chondroitin sulfate proteoglycan (CSPG) binding domain, and the SRP further comprises a SOCS3 binding domain.

Chondroitin sulfate proteoglycans (CSPGs) are the major components of scar, which are significantly increased after injury/trauma to both peripheral nervous system (PNS) and central nervous system (CNS). However, there is no clinically applicable strategy to reduce CSPGs now. The CSPG reduction peptides (CRPs), and nucleic acid sequences encoding CRPs, provide an effective way to remove CSPGs from the site of injury caused by trauma or neurodegeneration or aging to CNS and PNS. The benefits of removing CSPGs after injury include promoting the regrowth of damaged nerves and enhancing functional outcomes.

In certain embodiments, the CRP has the following sequence: N—YGRKKRRQRRR-PKPRVTWNKKGKKVNSQRF-KFERQKILDQRFFE—C (SEQ ID NO: 4). One of skill in the art could construct a corresponding nucleic acid sequence based on the known codon triplets for the amino acids specified in SEQ ID NO:4. The SEQ ID NO:4 sequence has the following three components:
- Cell membrane penetrating domain: YGRKKRRQRRR (SEQ ID NO:1);
- Central CSPG binding domain: PKPRVTWNKKGKKVNSQRF (SEQ ID NO: 2); and
- Lysosome targeting domain: KFERQKILDQRFFE (SEQ ID NO: 3).

In certain embodiments, the SRP has the following sequence:
- N-terminal cell membrane penetrating domain: YGRKKRRQRRR (SEQ ID NO:1);
- Central CSPG binding domain from PTP sigma: VQpYSTVVHS (SEQ ID NO:54); and
- C-terminal lysosome targeting domain: KFERQKILDQRFFE (SEQ ID NO:3).

Each of these domains may be constructed with longer, shorter, or mutated versions of the sequences shown in SEQ ID NOS: 1-3 and 54. For example, one could change one, two, three amino acids in these sequences. For example, one could make conservative changes to a particular amino acid sequence. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, and asparagine-glutamine. In certain embodiments, provided herein are peptides that have substantial identity to at least a portion of the amino acid sequences shown in SEQ ID NOs: 1-89.

In certain embodiments, the N-terminal cell-membrane penetrating domain of a CRP or SRP is an amino acid sequence as shown in SEQ ID NOs: 1 and 5-27 of Table 1 or such a peptide with one, two, or three (or more) N-terminal or C-terminal additions, subtractions or mutations therein. One of skill in the art could construct a corresponding nucleic acid sequence based on the known codon triplets for the amino acid sequences shown in Table 1.

TABLE 1

| | Amino acid (AA) sequences | SEQ ID NO: |
|---|---|---|
| HIV-1 Tat-(47-57) | YGRKKRRQRRR | 1 |
| HIV-1 Tat-(47-57)-C | YGRKKRRQRRR-C | 5 |
| HIV-1 Tat-(47-57)-GC | YGRKKRRQRRR-GC | 6 |
| CA-HIV-1 Tat-(47-57) | CA-YGRKKRRQRRR | 7 |

TABLE 1-continued

| | Amino acid (AA) sequences | SEQ ID NO: |
|---|---|---|
| HIV-1 Tat-(47-57) 3x | YGRKKRRQRRRYGRKKRRQRRRYGRKKRRQRRR | 8 |
| HIV-1 Tat-(48-57) | GRKKRRQRRR | 9 |
| HIV-1 Tat-(48-57)-G | GRKKRRQRRR-G | 10 |
| HIV-1 Tat-(48-57)-CG | GRKKRRQRRR-CG | 11 |
| HIV-1 Tat-(48-59) | GRKKRRQRRRPP | 12 |
| HIV-1 Tat-(48-60) | GRKKRRQRRRPPQ | 13 |
| HIV-1 Tat-(48-60)-C | GRKKRRQRRRPPQ-C | 14 |
| HIV-1 Tat-(49-57) | RKKRRQRRR | 15 |
| D-Tat (49-57) | rkkrrqrrr | 16 |
| Retro - Tat (57-49) | RRRQRRKKR | 17 |
| D-Retro - Tat (57-49) | rrrqrrkkr | 18 |
| R9-TAT | GRRRRRRRRRPPQ | 19 |
| HIV-1 Rev-(34-50) | TRQARRNRRRRWRERQR-GC | 20 |
| HTLV-II Rex-(4-16) | TRRQRTRRARRNRGC | 21 |
| CCMV Gag-(7-25) | KLTRAQRRAAARKNKRNTR-GC | 22 |
| FHV coat-(35-49) | RRRRNRTRRNRRRVR | 23 |
| Arg6 | RRRRRR-GC | 24 |
| Arg8 | RRRRRRRR-GC | 25 |
| Pep-1 | KETWW-ETWWTEWSQPKKKRKV | 26 |
| Antp-(43-58) | RQILIWFQNRRMKWKK | 27 |

In other embodiments, the cell membrane penetrating peptide is a protein transduction domain (PTD) with the presence of multiple arginine (R) residues as shown in SEQ ID NOs: 1 and 5-27 of Table 1. In other embodiments, the cell membrane penetrating peptide is a cell penetrating peptide (CPP) from the CPPsite 2.0, which is an updated version of database CPPsite. This site contains around 1700 unique cell penetrating peptides (CPPs) along with their secondary & tertiary structure, and can be found at www. followed by "crdd.osdd.net/raghava/cppsite/."

In certain embodiments, the C-terminal lysosomal targeting domain of a CRP or SRP is an amino acid sequence as shown in SEQ ID NOs: 23 and 28-36 of Table 2 or such a peptide with one, two, or three (or more) N-terminal or C-terminal additions, subtractions or mutations therein. In other embodiments, the lysosomal targeting domain is a chaperone-mediated autophagy (CMA)-targeting motif (CTM) containing a KFERQ-like motif, such as those shown in SEQ ID NOs: 2 and 28-36 of Table 2. One of skill in the art could construct a corresponding nucleic acid sequence based on the known codon triplets for the amino acid sequences shown in Table 2.

TABLE 2

| Amino acid (AA) sequences | SEQ ID NO: |
|---|---|
| KFERQKILDQRFFE | 2 |
| KFERQ-like | 28 |
| KFERQ | 29 |
| QKILD | 30 |
| QRFFE | 31 |
| KFERQKILD | 32 |
| QKILDQRFFE | 33 |
| KFERQRFFE | 34 |
| QRFFERQ | 35 |
| QRKFERQ | 36 |

In certain embodiments, the CSPG binding domain of a CRP is an amino acid sequence as shown in SEQ ID NOs: 2 and 37-53 of Table 3 or such a peptide with one, two, or three (or more) N-terminal or C-terminal additions, subtractions or mutations therein. One of skill in the art could construct a corresponding nucleic acid sequence based on the known codon triplets for the amino acid sequences shown in Table 3.

TABLE 3

| Amino acid (AA) sequences | SEQ ID NO: |
|---|---|
| PKPRVTWNKKGKKVNSQRF | 3 |
| KKGKK | 37 |
| NKKGKKV | 38 |
| NKKGKKVNS | 39 |
| KKGKKVNSQRF | 40 |
| RVTWNKKGKKVNSQR | 41 |
| PKPRVTWNKKGKKVNSQRFE | 42 |
| TGDPKPRVTWNKKGKKVNSQRF | 43 |
| TGDPKPRVTWNKKGKKVNSQRFE | 44 |
| PKPRVTWNRKGKKVNSQRF | 45 |
| PKPRVTWNRRGKKVNSQRF | 46 |
| PKPRVTWNRRGRKVNSQRF | 47 |
| PKPRVTWNRRGRRVNSQRF | 48 |
| PKPRVTWNKRGKKVNSQRF | 49 |
| PKPRVTWNKRGRKVNSQRF | 50 |
| PKPRVTWNKRGRRVNSQRF | 51 |
| PKPRVTWNKKGRKVNSQRF | 52 |
| PKPRVTWNKKGRRVNSQRF | 53 |

In certain embodiments, the SOCS3 binding domain of a SRP is an amino acid sequence as shown in SEQ ID NOs: 54-89 of Table 4 or such a peptide with one, two, or three (or more) N-terminal or C-terminal additions, subtractions or mutations therein. One of skill in the art could construct a corresponding nucleic acid sequence based on the known codon triplets for the amino acid sequences shown in Table 4.

TABLE 4

SOCS3 binding domain peptides

| Amino acid (AA) sequences | SEQ ID NO: |
|---|---|
| V-Q-pY-S-T-V-V-H-S | 54 |
| V-Q-Y-S-T-V-V-H-S | 55 |
| V-E-pY-S-T-V-V-H-S | 56 |
| V-E-Y-S-T-V-V-H-S | 57 |
| V-X-pY-X-X-V-V-X | 58 |
| V-X-pY-X-X-L-V-X | 59 |
| V-X-pY-X-X-V-L-X | 60 |
| L-X-pY-X-X-V-V-X | 61 |
| V-X-pY-X-X-L-L-X | 62 |
| L-X-pY-X-X-V-L-X | 63 |
| L-X-pY-X-X-L-V-X | 64 |
| L-X-pY-X-X-L-L-X | 65 |
| V-X-Y-X-X-V-V-X | 66 |
| V-X-Y-X-X-L-V-X | 67 |
| V-X-Y-X-X-V-L-X | 68 |
| L-X-Y-X-X-V-V-X | 69 |
| V-X-Y-X-X-L-L-X | 70 |
| L-X-Y-X-X-V-L-X | 71 |
| L-X-Y-X-X-L-V-X | 72 |
| L-X-Y-X-X-L-L-X | 73 |
| V-X-pY-X-X-V-V-X-S | 74 |
| V-X-pY-X-X-L-V-X-S | 75 |
| V-X-pY-X-X-V-L-X-S | 76 |
| L-X-pY-X-X-V-V-X-S | 77 |
| V-X-pY-X-X-L-L-X-S | 78 |
| L-X-pY-X-X-V-L-X-S | 79 |
| L-X-pY-X-X-L-V-X-S | 80 |
| L-X-pY-X-X-L-L-X-S | 81 |
| S-T-A-S-T-V-E-pY-S-T-V-V-H-S-G | 82 |
| S-T-A-S-T-V-E-pY-S-T-V-V-H-S | 83 |
| S-T-A-S-T-V-Q-pY-S-T-V-V-H | 84 |
| S-T-A-S-T-V-Q-pY-S-T-V-V | 85 |
| S-T-A-S-T-V-Q-pY-S-T-V-V-H-S-G | 86 |
| S-T-A-S-T-V-Q-pY-S-T-V-V-H-S | 87 |
| S-T-A-S-T-V-Q-pY-S-T-V-V-H | 88 |
| S-T-A-S-T-V-Q-pY-S-T-V-V | 89 | pY: phosphorylated tyrosine;
X: any amino acid

Work conducted during development of embodiments described herein demonstrate that injected SRP distributes to macrophages/microglia to be co-localized with lysosomes and SCI-upregulated SOCS3. SRP specifically and significantly reduces SOCS3, and it is associated with increased STAT3 activity. SRP treatment post-SCI significantly decreased pro-inflammatory responses, as indicated by decreased expression of both inducible nitric oxide synthase (iNOS) and TNF-α. Furthermore, SRP treatment significantly increased the amounts of TBK1 and the mitophagy adaptor optineurin, and enhanced phosphorylation of TBK1 and the mitophagy adaptor p62, as compared to treatment with scrambled peptide. Work conducted during development of embodiments described herein demonstrated that in a T8 contusion SCI model, SRP treatment significantly improves recovery of both locomotion and micturition three months after SCI.

EXAMPLES

Example 1

This Example describes treating spinal cord injury (SCI) in a model using a CSPG reduction peptide (CRP). The CRP had the following three components:

N-terminal cell membrane penetrating domain:

```
                                          (SEQ ID NO: 1)
YGRKKRRQRRR;
```

Central CSPG binding domain from PTP sigma;

```
                                          (SEQ ID NO: 2)
PKPRVTWNKKGKKVNSQRF;
``` and
C-terminal lysosome targeting domain:

```
                                          (SEQ ID NO: 3)
KFERQKILDQRFFE.
```

The full CRP sequence is as follows:

```
                                          (SEQ ID NO: 4)
N - YGRKKRRQRRR-PKPRVTWNKKGKKVNSQRF-KFERQKILDQRFF
E - C.
```

The designed CRP (SEQ ID NO:4) includes an N-terminal cell membrane-penetrating domain (SEQ ID NO:1), a central CSPGs binding domain (SEQ ID NO:2), and a C-terminal lysosome targeting domain (SEQ ID NO:3) for directing the CRP-CSPGs complex to lysosomes for degradation. FIG. 1 shows a schematic of the exemplary CRP employed in this Example, as well as some of the benefits of such constructs.

In this Example, the CRP has been applied in a preclinical rat model to test the efficacy of the treatment of spinal cord injury (SCI). The injury was made at thoracic 8 level using contusive injury device. The contusive SCI is the most clinical relevance among all experimental SCI models. We have assessed both motor and bladder control as functional outcomes and analyzed anatomical evidences to support these findings. We also selected sub-acute phase (ONE-DAY after SCI) and chronic phase (TWO-MONTHs after SCI) to start our treatment. FIG. 2 shows a schematic of the experimental design for the in vivo testing in this Example.

For the sub-acute treatment, continuous daily subcutaneous injection of CRP beginning one-day after SCI significantly reduces SCI-induced overexpression of CSPGs. Furthermore CRP can efficiently improve locomotion and bladder electromyography (EMG) activities and voiding patterns after SCI. Particularly, we found that CRP increases sprouting/regeneration of axons including serotonin (5-HT) and anterogradely traced fibers from brain stem and red nuclei, the critical pathways regulating both locomotion and bladder functions, below the SCI lesion and even in the lumbosacral spinal cord.

Figure 3:
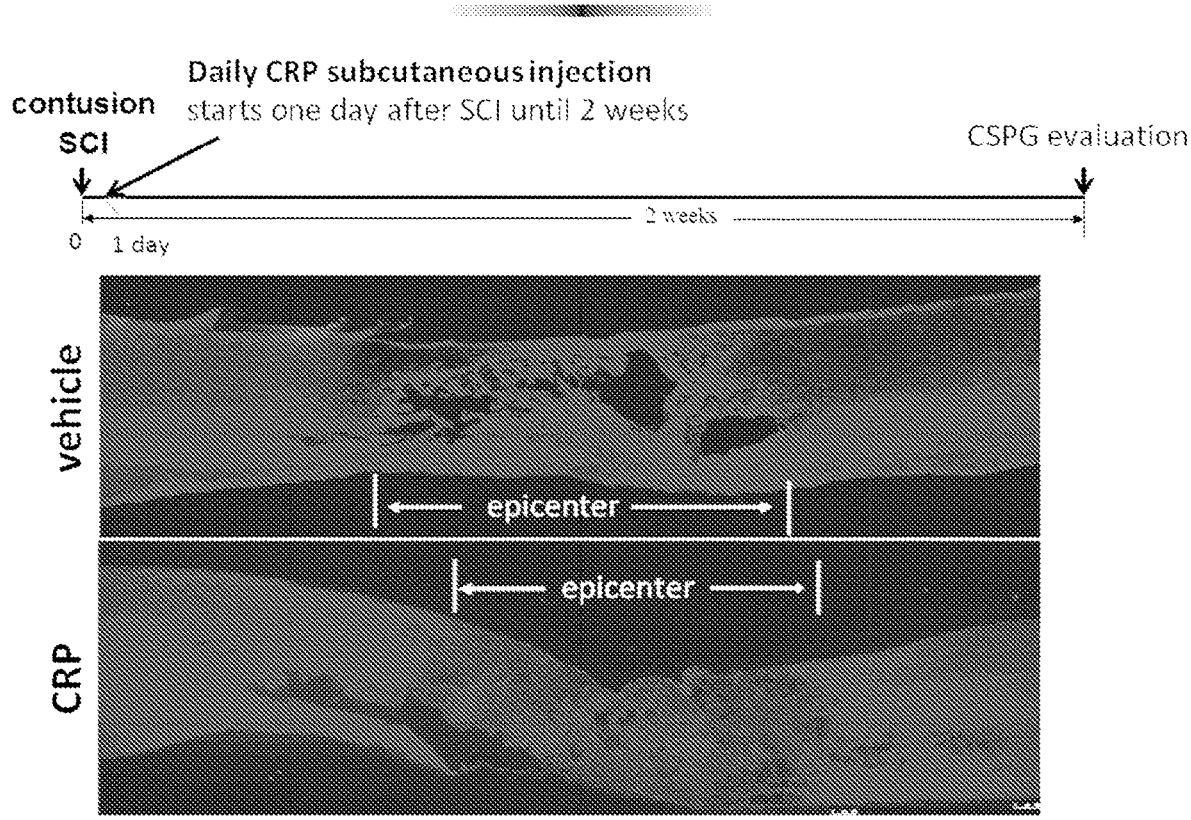
FIG. 3 shows histological results from the testing when CRP was applied sub-acutely in Example 1, where the CRP effectively decreased CSPG (the major component of scars) in lesion epicenter and adjacent tissue two weeks after SCI.
Figure 4:
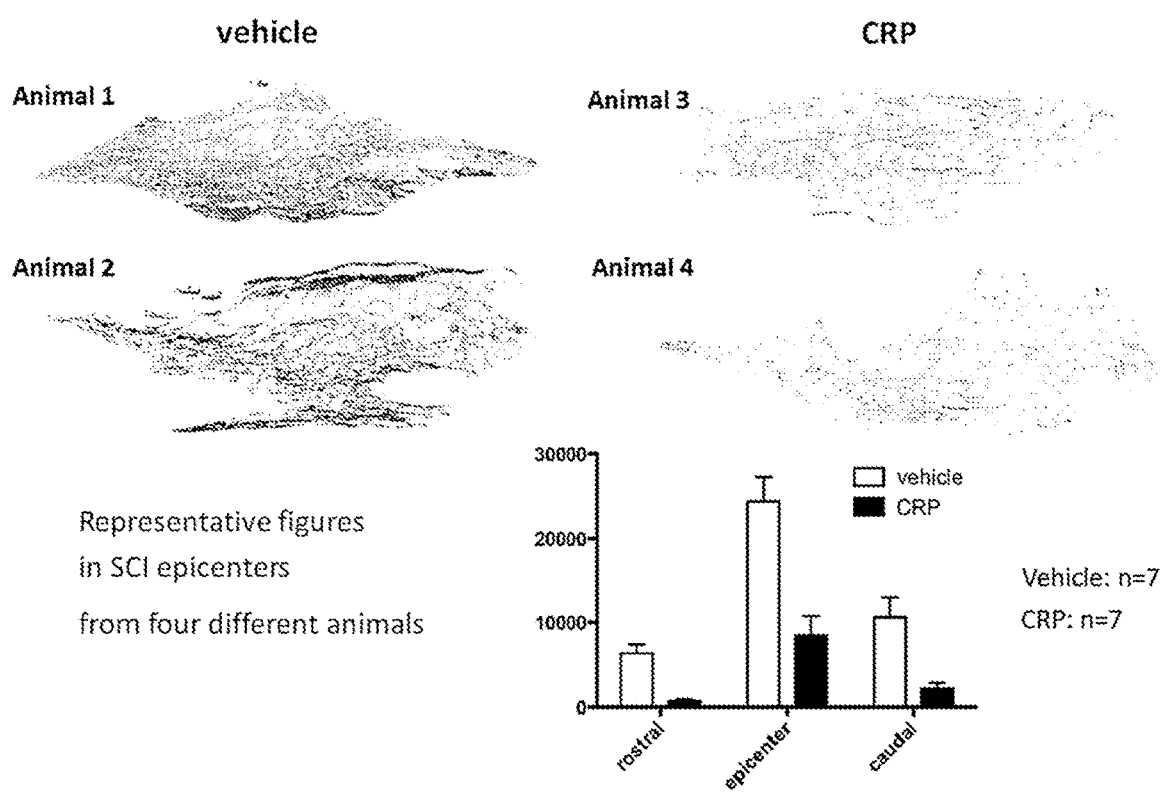
FIG. 4 shows results from the testing when CRP was applied sub-acutely, where the exemplary CRP significantly decreased CSPG three months after SCI.
Figure 5:
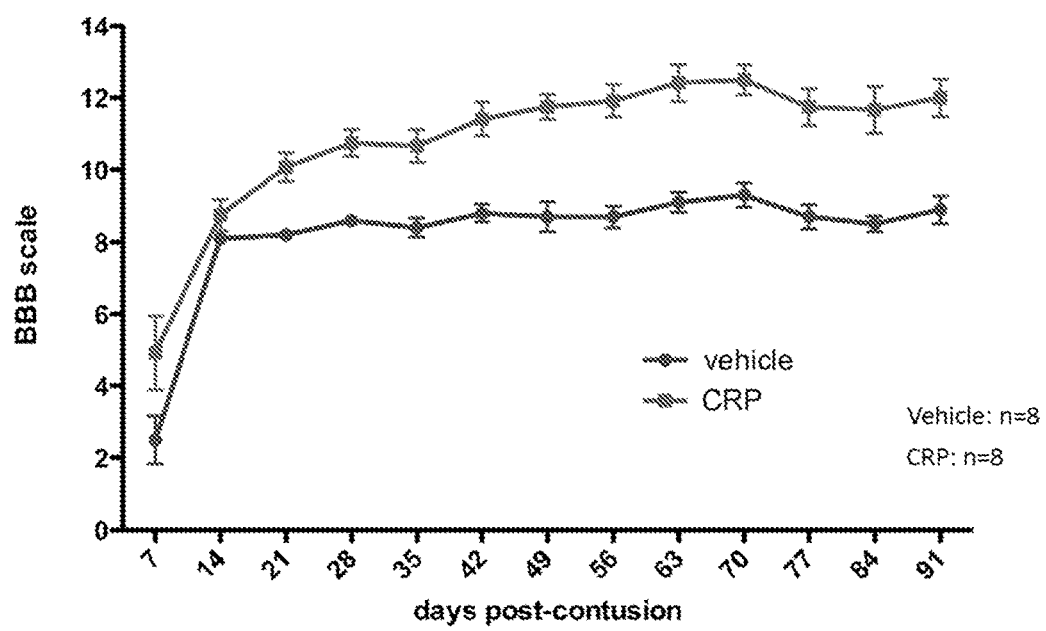
FIG. 5 shows results out to 91 days post-contusion shows that the CRP significantly promotes motor function recovery after SCI.
Figure 6:
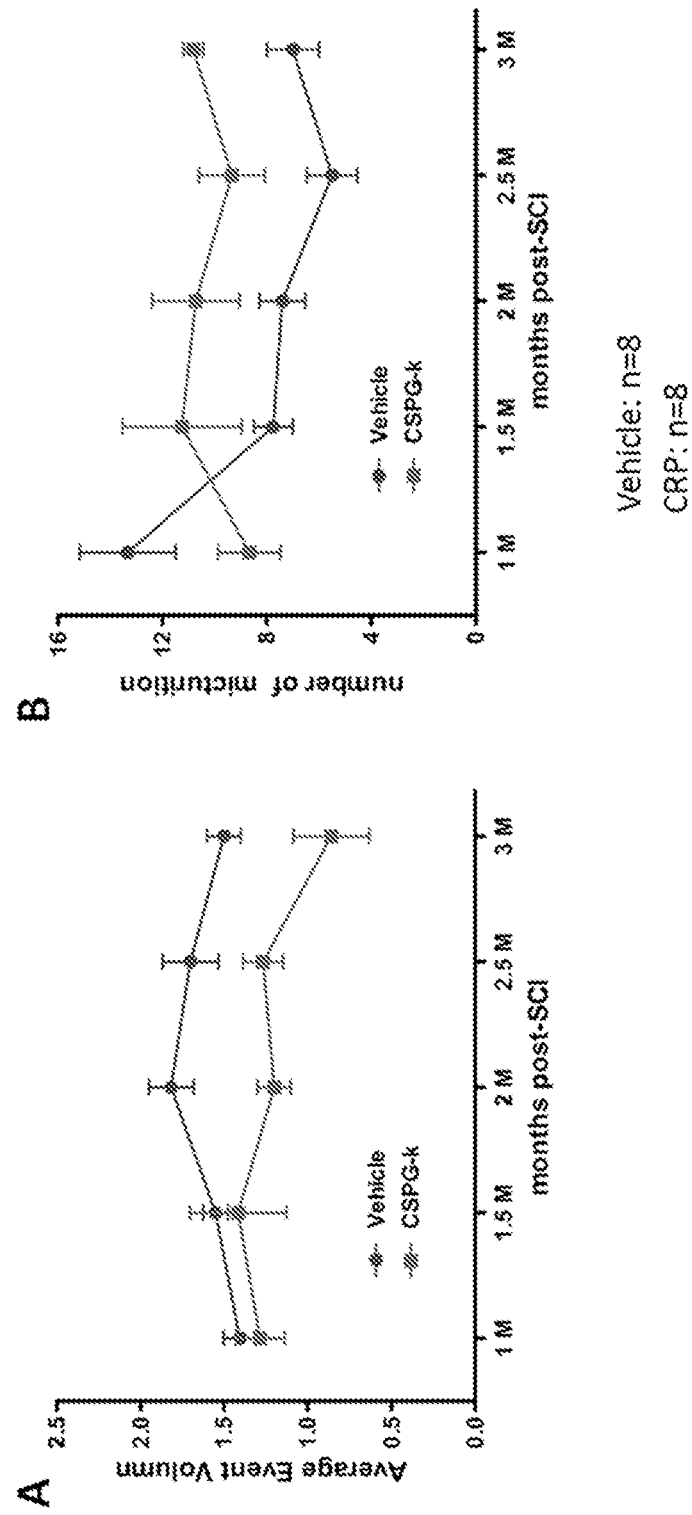
FIG. 6 shows that the CRP improves voiding patterns after SCI.
Figure 7:
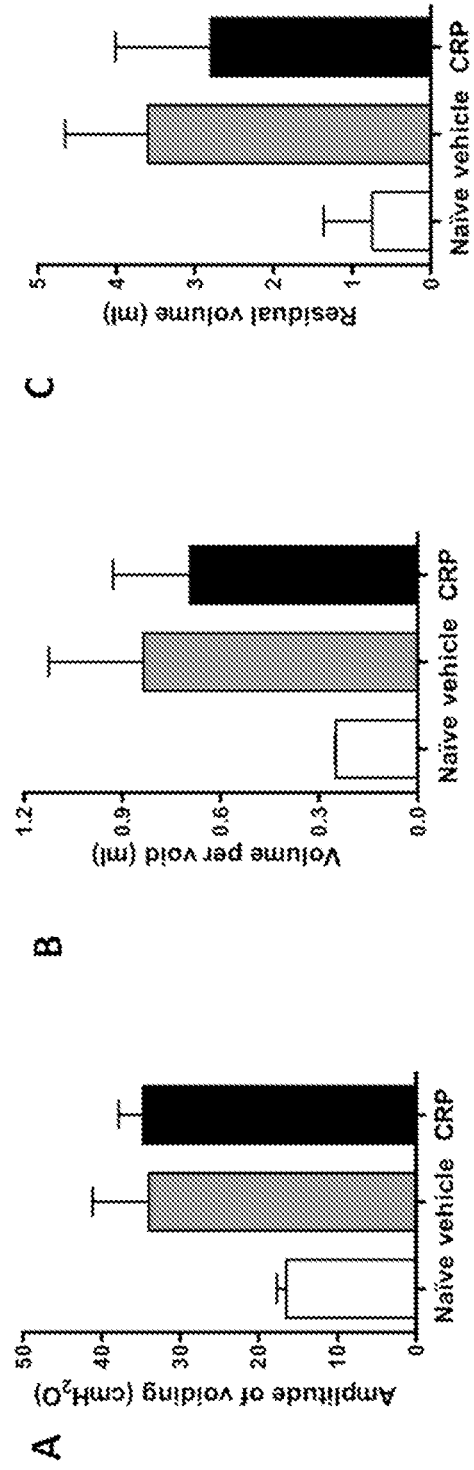
FIG. 7 shows that the CRP improves bladder function after SCI, reducing residual volume and volume per void toward normal condition.
Figure 8:
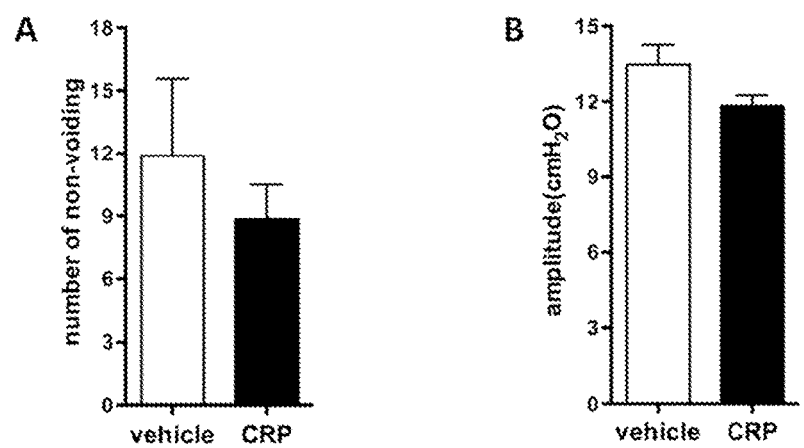
FIG. 8 shows that the CRP improves bladder function after SCI, reducing overactive bladder by the reduction of both the number and amplitude of non-voiding contraction.
Figure 9:
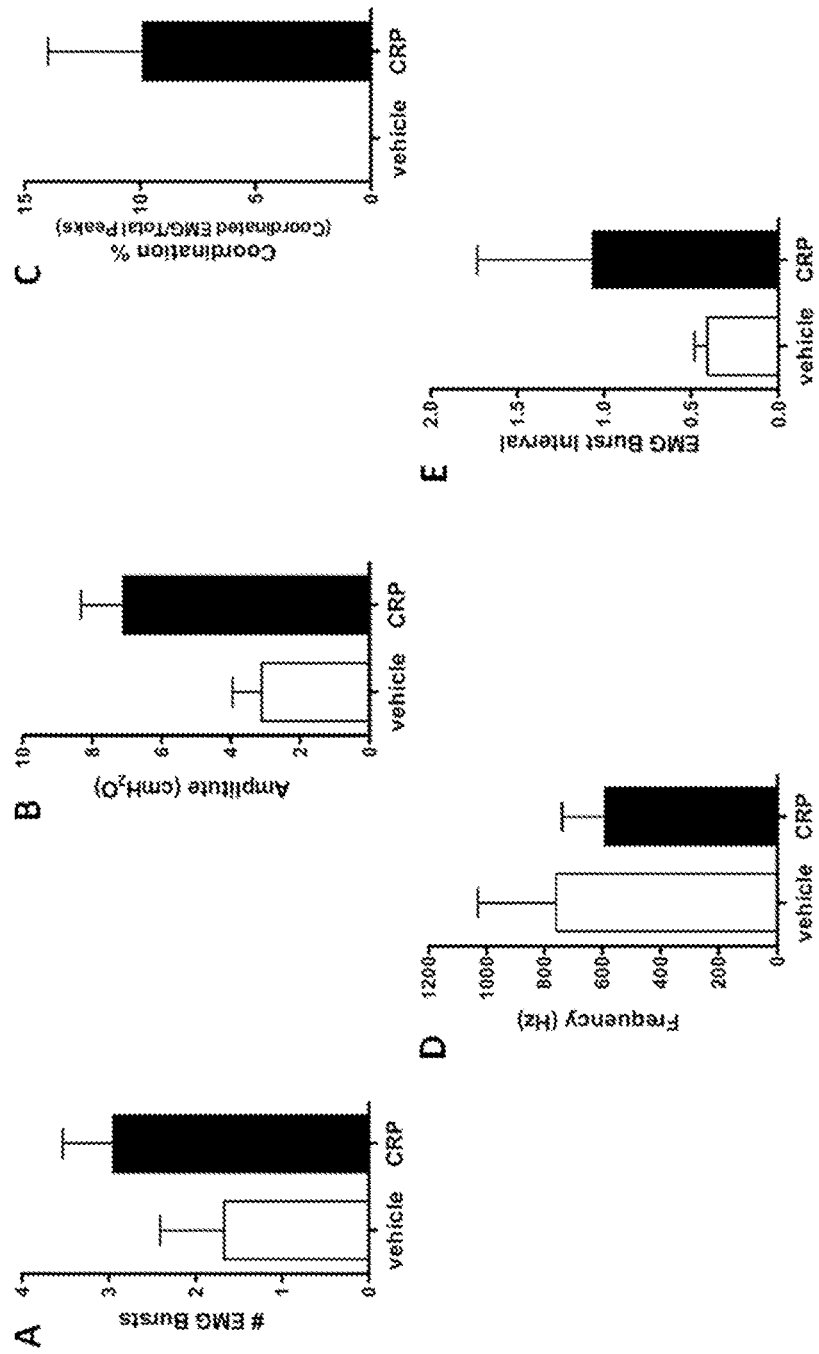
FIG. 9 shows that the CRP improves bladder function after SCI, improving external urethral sphincter (EUS) activity by increasing the number of burst, the EMG amplitude, and the coordination with detrusor contraction during the void period.
Figure 10:
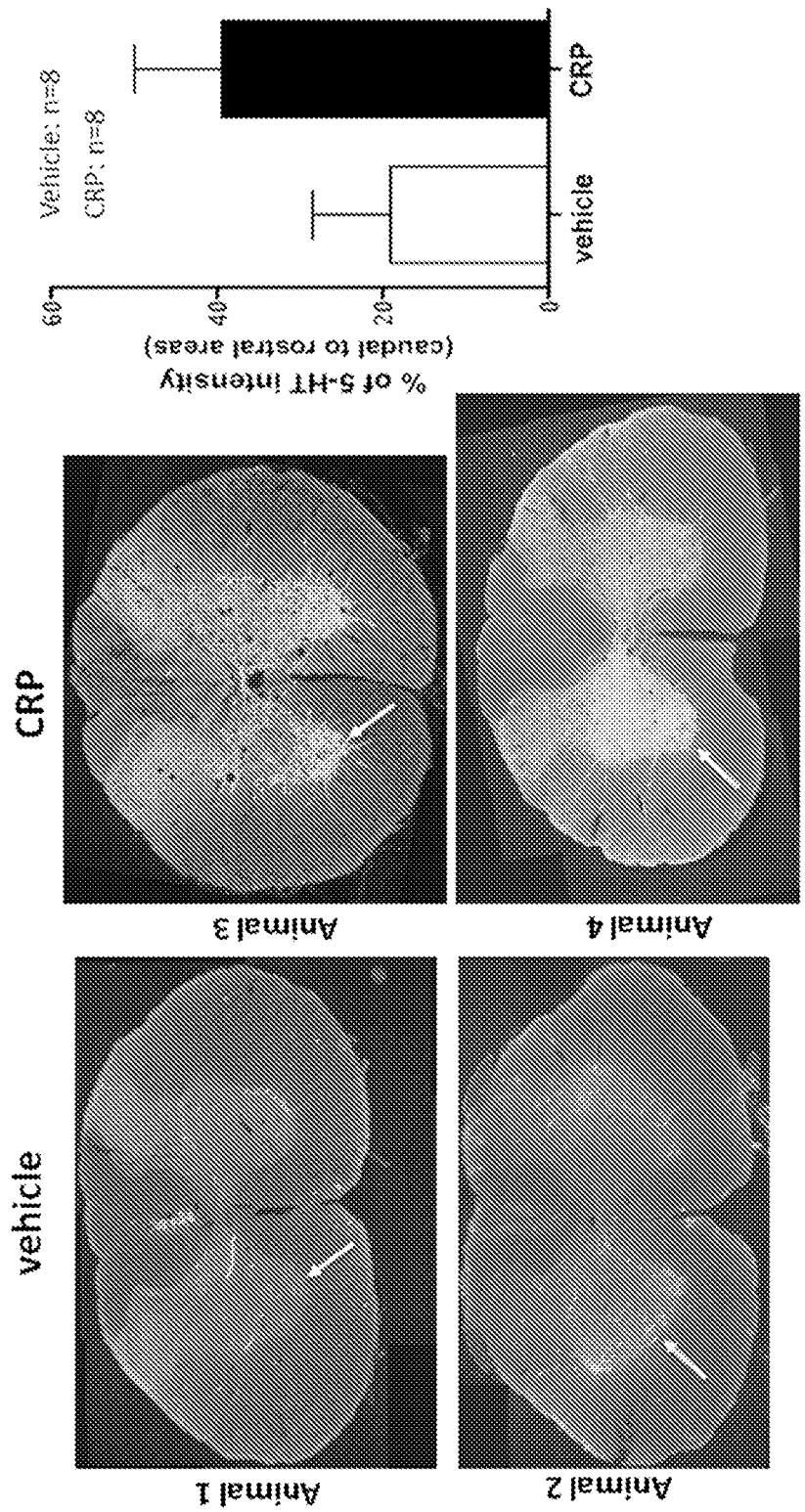
FIG. 10 shows the CRP enhances sprouting of serotonin (5-HT) fibers below lesion after SCI.
Figure 11:
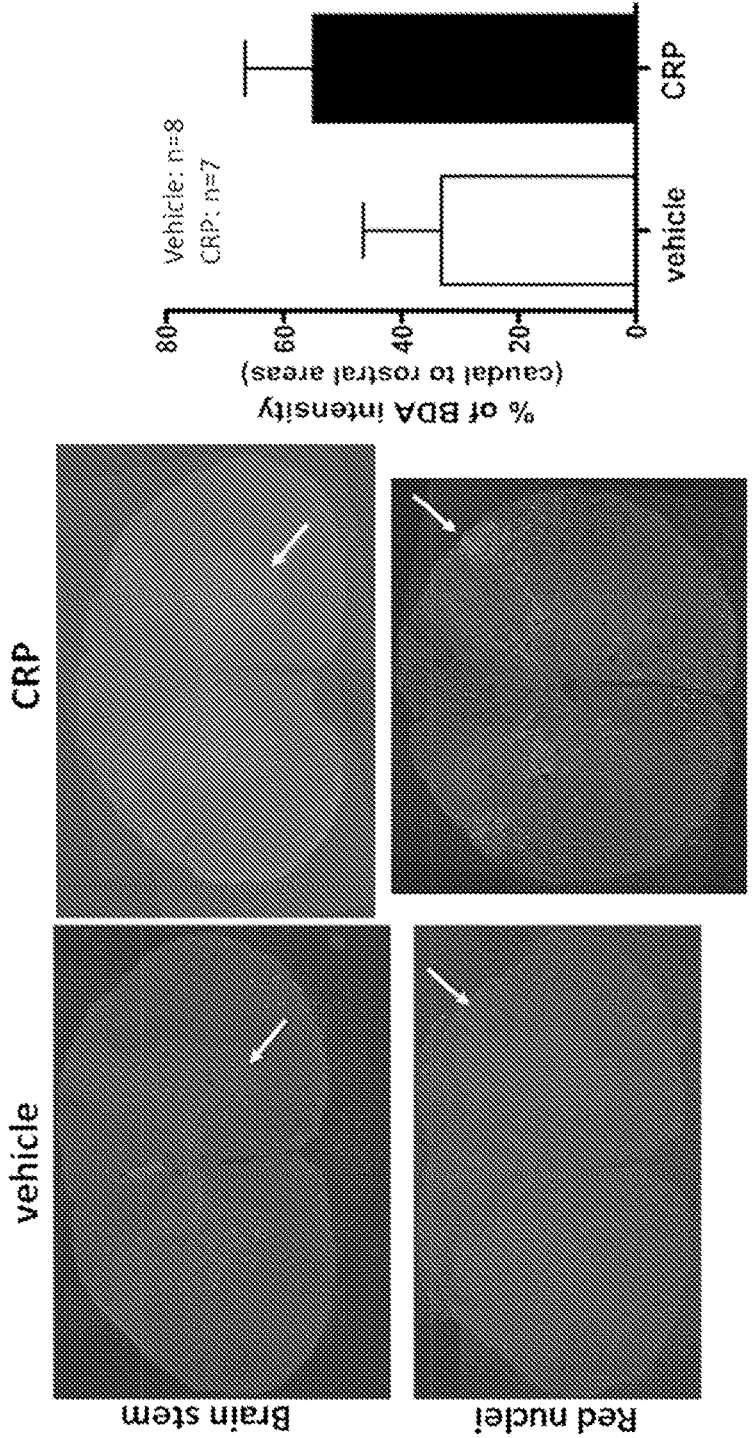
FIG. 11 shows that the CRP enhances nerve sprouting below lesion from neuron in brain stem and red nucleic after SCI.

The results of this testing are shown in the figures. In particular, FIG. 3 shows histological results from the sub-acute treatment, where CRP effectively decreased CSPG in lesion epicenter and adjacent tissue two weeks after SCI. FIG. 4 shows results from the sub-acute treatment, where CRP significantly decreased CSPG three months after SCI. FIG. 5 shows results out to 91 days post-contusion shows that CRP significantly promotes motor function recovery after SCI. FIG. 6 shows that CRP improves voiding patterns after SCI. FIG. 7 shows that CRP improves bladder function after SCI, reducing residual volume and volume per void toward normal condition. FIG. 8 shows that CRP improves bladder function after SCI, reducing overactive bladder by the reduction of both the number and amplitude of non-voiding contraction. FIG. 9 shows that CRP improves bladder function after SCI, improving external urethral sphincter (EUS) activity by increasing the number of burst, the EMG amplitude, and the coordination with detrusor contraction during the void period. FIG. 10 shows CRP enhances sprouting of serotonin (5-HT) fibers below lesion after SCI. FIG. 11 shows that CRP enhances nerve sprouting below lesion from neuron in brain stem and red nucleic after SCI.

Figure 12:
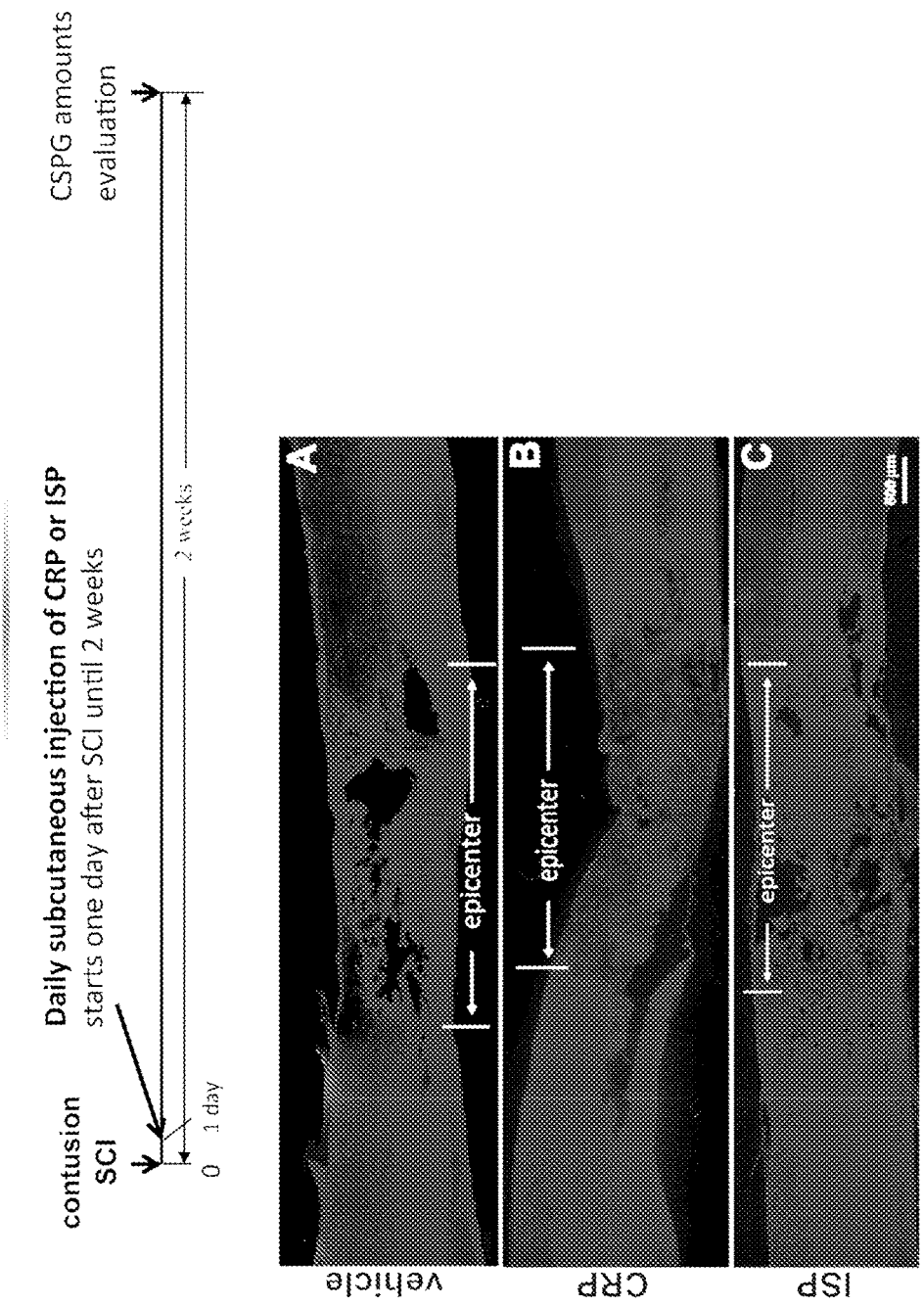
FIG. 12 shows the CRP, but not ISP, when applied one day after SCI effectively decreases CSPG in lesion epicenter and adjacent tissue two weeks after SCI. The expression of inhibitory chondroitin sulfate proteoglycan (CSPG) is upregulated surround the lesion in spinal cord two weeks after contusive SCI in the vehicle-treated animal (A). CSPG reduction peptide (CRP) treatment (B) starting one day after SCI significantly decreases SCI-induced increases in CSPG. However, intracellular sigma peptide (ISP) treatment (C) does not decrease CSPG as compared to vehicle-treated group (A).
Figure 13:
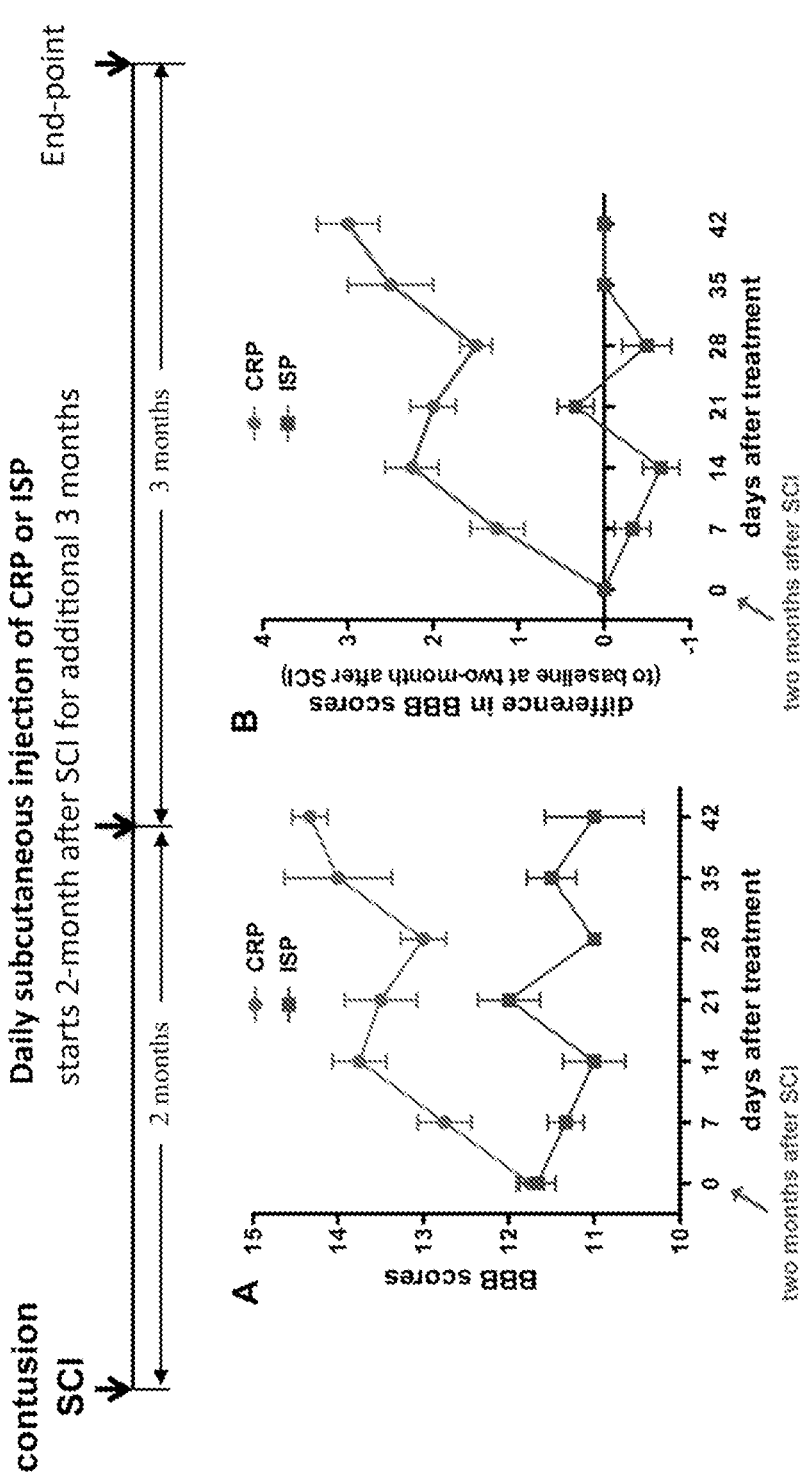
FIG. 13 shows that the CRP, but not ISP, when applied two months after SCI effectively promotes locomotion recovery. Basso, Beattie, and Bresnahan (BBB) 21-point scoring test is used as the locomotion assessment after SCI. SCI causes significant deficits on locomotion function as indicated by the significant drop of BBB scores from 21 of the normal rats. CRP treatment starting two months after contusive SCI significantly improves locomotion recovery indicated by BBB score increased from 11.75±0.164 (two months after SCI) to 14.33±0.211 (A) with average increases in BBB scores by 3.0±0.365 (B) by two months plus 42 days after SCI. However, ISP treatment slightly decreases BBB scores from 11.667±0.211 (two months after SCI) to 11.00±0.577 (two months plus 42 days after SCI) (A).

The above were followed up with studies to evaluate the treatment effects of CRP in chronic SCI. The chronic SCI is not only way more challenge to be repaired but also is the clinical status of the majority of patients with SCI. Our results find that CRP subcutaneously injected even beginning two-month after SCI still significantly improves the locomotion and voiding patterns In addition, we made a comparison of CRP with recently developed peptides, intracellular sigma peptide (ISP) targeting CSPG receptor pathways. Our data showed (1) CRP but not ISP could reduce CSPG after SCI and (2) importantly, CRP but not ISP could improve functional outcomes after chronic phase of SCI. FIG. 12 shows CRP, but not ISP, effectively decreases CSPG in lesion epicenter and adjacent tissue two weeks after SCI. FIG. 13 shows that CRP, but not ISP, when applied two months after SCI effectively promoted locomotion recovery.

Because CSPGs are the major physical barriers for axonal regeneration and functional recovery after trauma in both PNS and CNS and after neurodegenerative disorders, CRP type construction could apply to many disorders other than SCI. Indeed, CRP could be applied to limb transplants. In addition, neurodegeneration-induced increases in heparin sulfate proteoglycans (HSPGs) as well as CSPGs are unbeatable barriers for current treatment of Multiple Sclerosis (MS), which indicates the therapeutic potential of CRP to treat neurodegenerative disorders such as MS and related conditions.

Example 2

This Example describes treating spinal cord injury (SCI) in a rat model using a SOCS3 reduction peptide (SRP). The SRP had the following three components:

N-terminal cell membrane penetrating domain:

```
                                          (SEQ ID NO: 1)
YGRKKRRQRRR;
```

Central SOCS3 binding domain from PTP sigma:

```
                                          (SEQ ID NO: 54)
VQpYSTVVHS;
```

C-terminal lysosome targeting domain:

```
                                          (SEQ ID NO: 3)
KFERQKILDQRFFE.
```

The full SRP sequence is as follows:

(SEQ ID NO: 90)
N - YGRKKRRQRRR-VQpYSTVVHS-KFERQKILDQRFFE - C.

Figure 14:
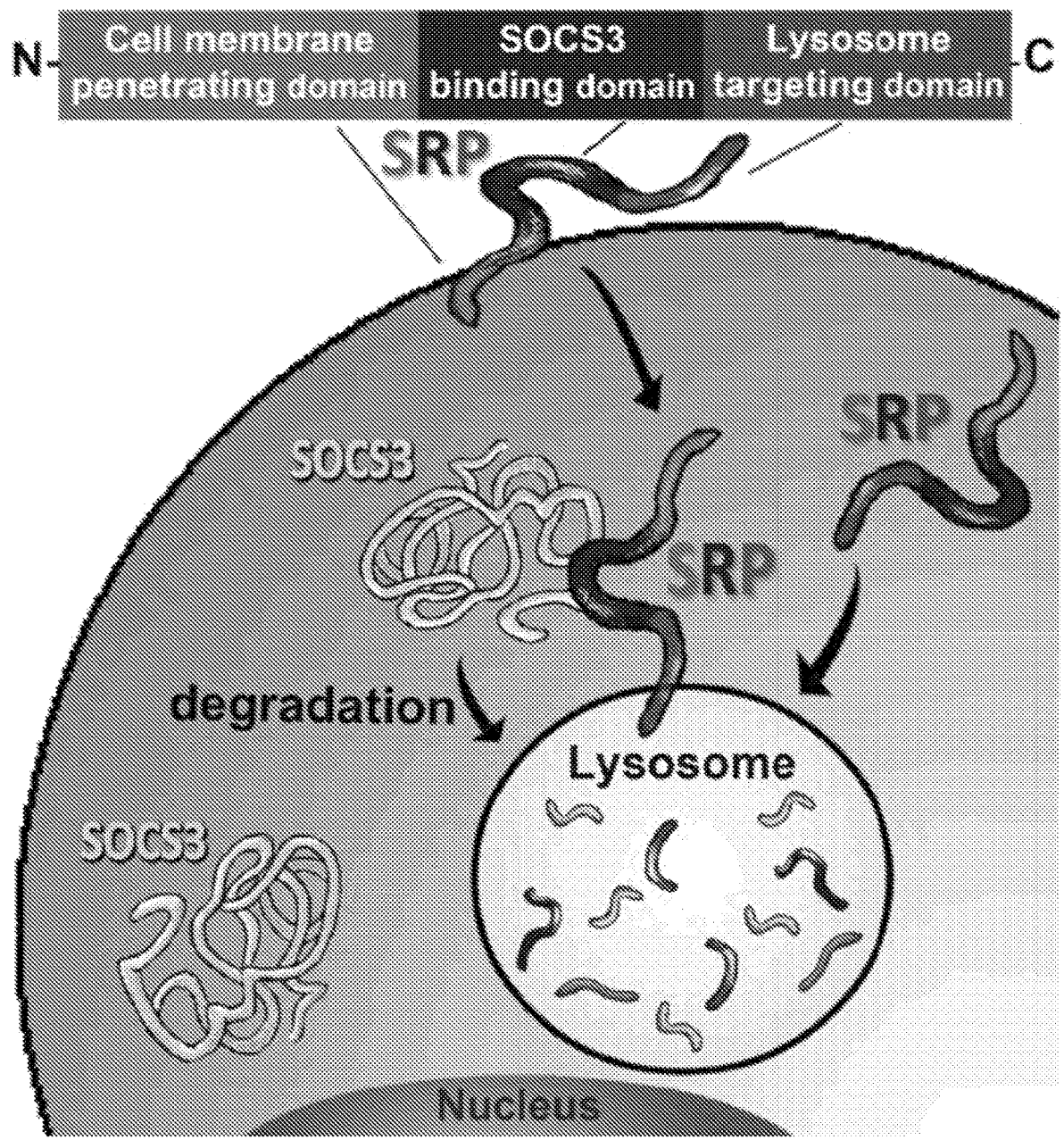
FIG. 14 shows exemplary degradation of SOCS3 using an exemplary SRP peptide. At the top of FIG. 4 is an illustration of an exemplary design of an SRP peptide, including the N-terminal cell membrane penetration domain, the central SOCS3 binding domain, and the C-terminal lysosome targeting domain that directs SRP-bound SOCS3 to lysosomes for degradation.

The designed SRP (SEQ ID NO:90) includes an N-terminal cell membrane-penetrating domain (SEQ ID NO:1), a central SOCS3 binding domain (SEQ ID NO:54), and a C-terminal lysosome targeting domain (SEQ ID NO:3) for directing the SRP-SOCS3 complex to lysosomes for degradation. FIG. 14 shows a schematic of the exemplary SRP employed in this Example.

In this Example, the SRP has been applied in a preclinical rat model to test the efficacy of the treatment of spinal cord injury (SCI) in a manner similar to Example 1 above for CRP. The results are as follows.

Figure 15:
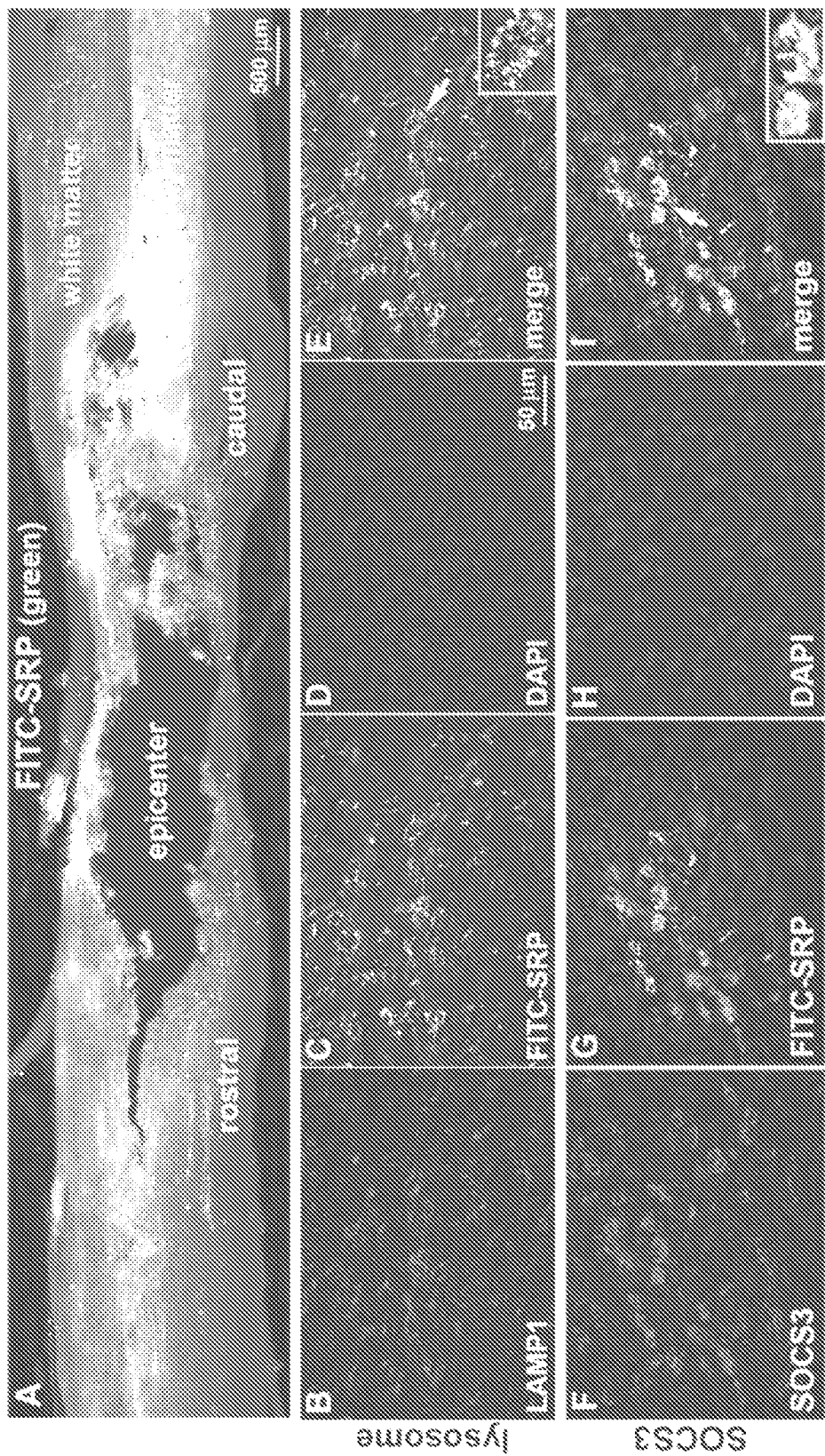
FIG. 15, panels A-I, shows the distribution of FITC-labeled SRP in the spinal cord and in lysosomes of target cells 8 days after contusive SCI. A single subcutaneous injection of FITC-SRP was administered 8 days after contusive SCI. Spinal cords were harvested 3 hours after injection. A, Representative image demonstrating FITC-labeled SRP (green) distributed surrounding the injury epicenter and in both gray matter and white matter. B-E, Representative 3D deconvolution images of co-localization (arrow, E) of FITC-SRP (C) with the lysosomal marker LAMP1 (B) in the spinal cord surrounding the injury epicenter. F-I, Singly injected FITC-SRP (G) co-localized (I) with SCI increased SOCS3 (F) in the areas surrounding the lesion epicenter at 8 days post SCI. The boxed area shows higher magnification of co-localization observed in the area indicated by the arrow.

FIG. 15, panels A-I, shows the distribution of FITC-labeled SRP (FITC-SRP) in the spinal cord and in lysosomes of target cells 8 days after contusive SCI. A single subcutaneous injection of FITC-SRP was administered 8 days after contusive SCI. Spinal cords were harvested 3 hours after injection. A, Representative image demonstrating FITC-labeled SRP (green) distributed surrounding the injury epicenter and in both gray matter and white matter. B-E, Representative 3D deconvolution images of co-localization (arrow, E) of FITC-SRP (C) with the lysosomal marker LAMP1 (B) in the spinal cord surrounding the injury epicenter. F-I, Singly injected FITC-SRP (G) co-localized (I) with SCI increased SOCS3 (F) in the areas surrounding the lesion epicenter at 8 days post SCI. The boxed area shows higher magnification of co-localization observed in the area indicated by the arrow.

Figure 16:
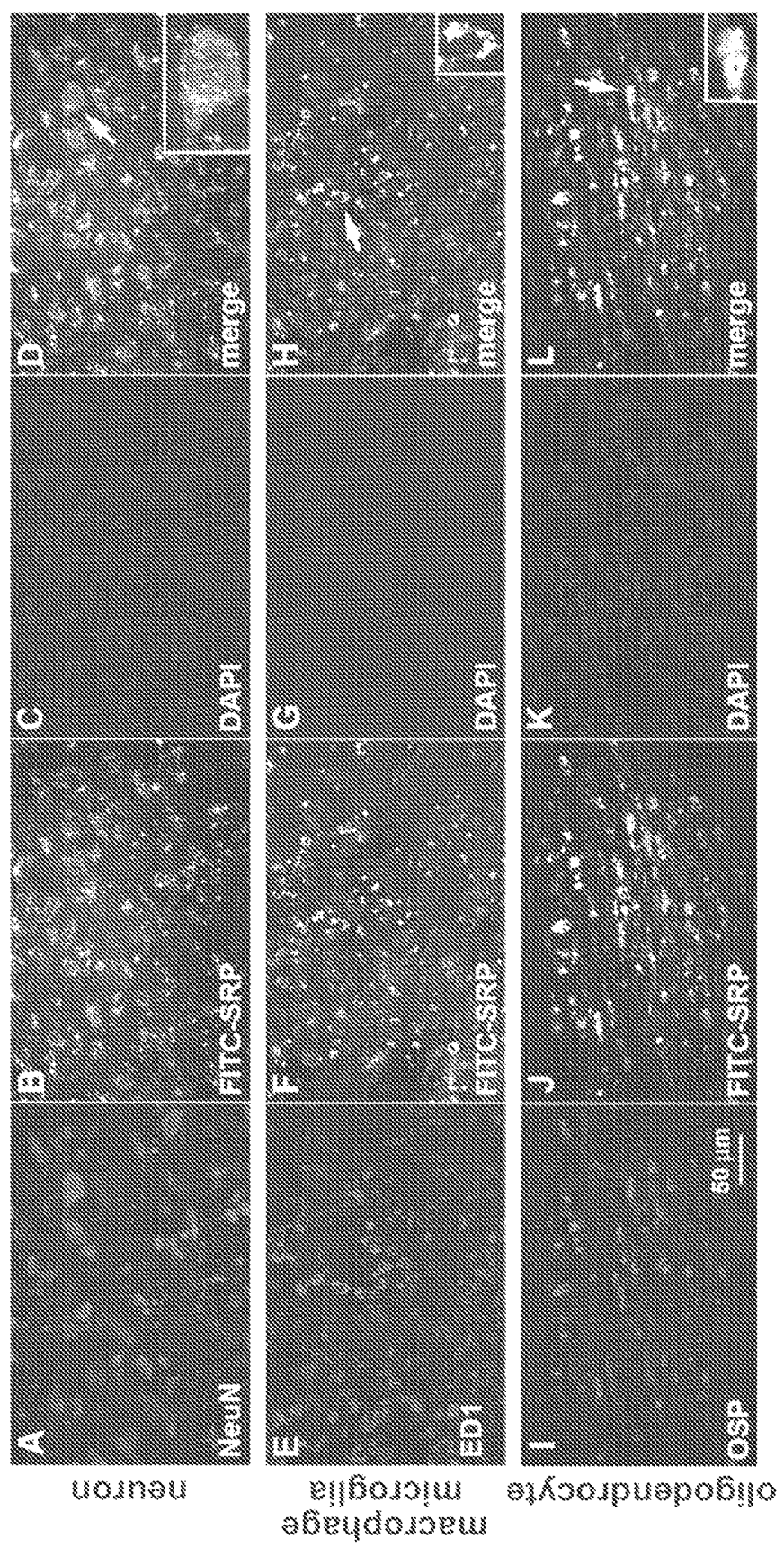
FIG. 16, panels A-L, shows that FITC-SRP was identified in neurons, microglia/macrophages, and oligodendrocytes. Representative 3D deconvolution images show the co-localization of FITC-SRP and neurons (NeuN+; A-D), or microglia/macrophages (ED1+; E-H), or oligodendrocytes (OSP+; I-L). The boxed area shows higher magnification of co-localized cells (arrow).

FIG. 16, panels A-L, shows that FITC-SRP was identified in neurons, microglia/macrophages, and oligodendrocytes. Representative 3D deconvolution images show the co-localization of FITC-SRP and neurons (NeuN+; A-D), or microglia/macrophages (ED1+; E-H), or oligodendrocytes (OSP+; I-L). The boxed area shows higher magnification of co-localized cells (arrow).

Figure 17:
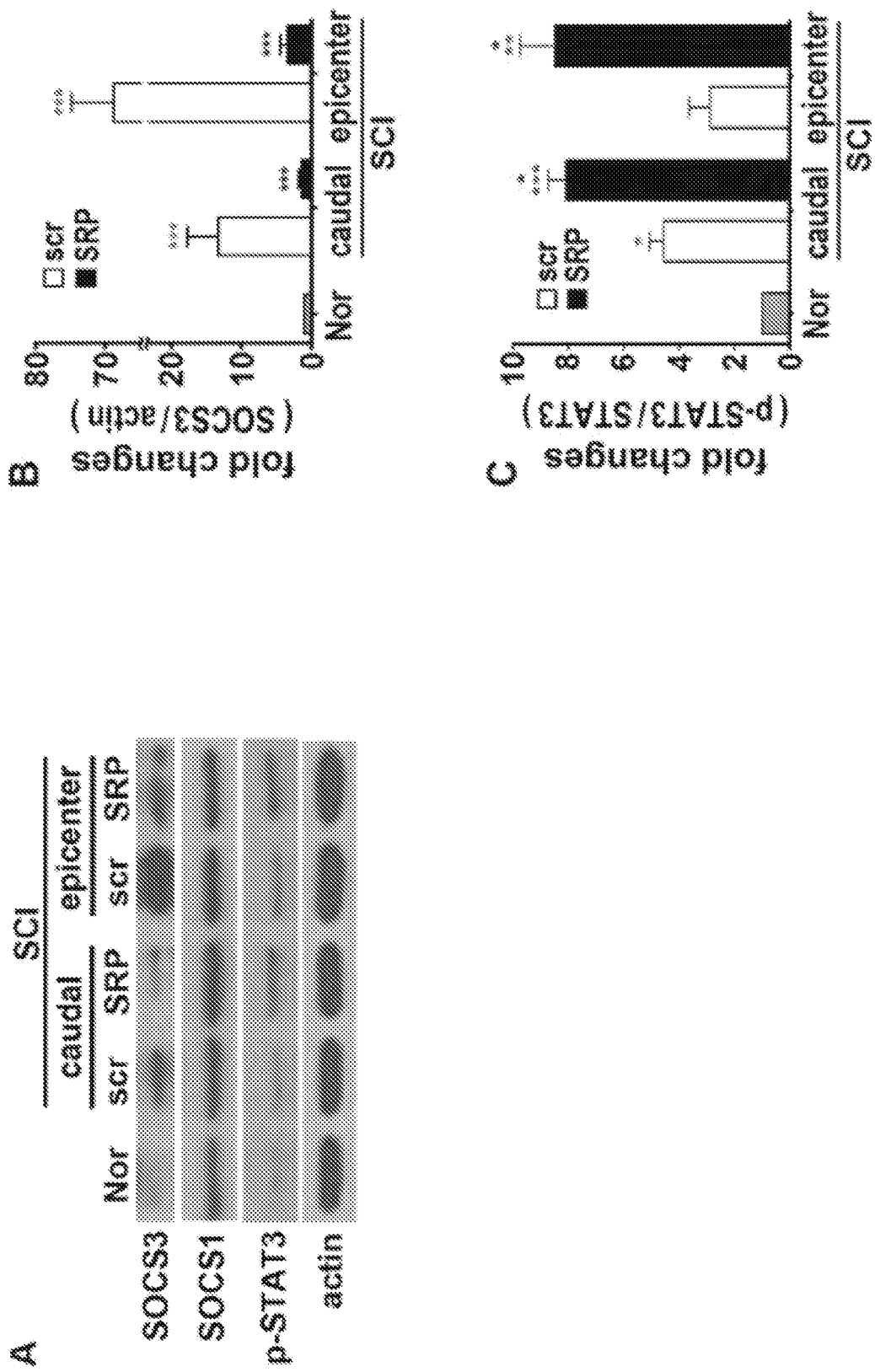
FIG. 17, panels A-C, shows SRP significantly reduced SOCS3 levels in the spinal cord after SCI. SOCS3 protein expression in the spinal cord of the scrambled peptide group (scr) was significantly increased 7 days after SCI at the epicenter and in areas caudal to the injured site compared to normal rats (Nor). The SCI-upregulated SOCS3 was significantly reduced by SRP treatment (SRP) beginning one day after SCI (once per day). Additionally, significant activation of STAT3, as indicated by phospho-STAT3 Tyr705 (p-STAT3) expression, was observed in SRP-treated SCI animals. SOCS1 and actin were not significantly altered by SRP treatment (A). Graphs represent mean±SEM of five samples per group for the ratios of SOCS3 to actin (B) and p-STAT3 to STAT3 (C).

FIG. 17, panels A-C, shows SRP significantly reduced SOCS3 levels in the spinal cord after SCI. SOCS3 protein expression in the spinal cord of the scrambled peptide group (scr) was significantly increased 7 days after SCI at the epicenter and in areas caudal to the injured site compared to normal rats (Nor). The SCI-upregulated SOCS3 was significantly reduced by SRP treatment (SRP) beginning one day after SCI (once per day). Additionally, significant activation of STAT3, as indicated by phospho-STAT3 Tyr705 (p-STAT3) expression, was observed in SRP-treated SCI animals. SOCS1 and actin were not significantly altered by SRP treatment (A). Graphs represent mean±SEM of five samples per group for the ratios of SOCS3 to actin (B) and p-STAT3 to STAT3 (C). +$p<0.05$, ++$p<0.01$, and +++$p<0.001$ compared to normal animals, and *$p<0.05$ and ***$p<0.001$ compared to scrambled peptide animals (two way ANOVA with Bonferroni multiple analyses).

Figure 18:
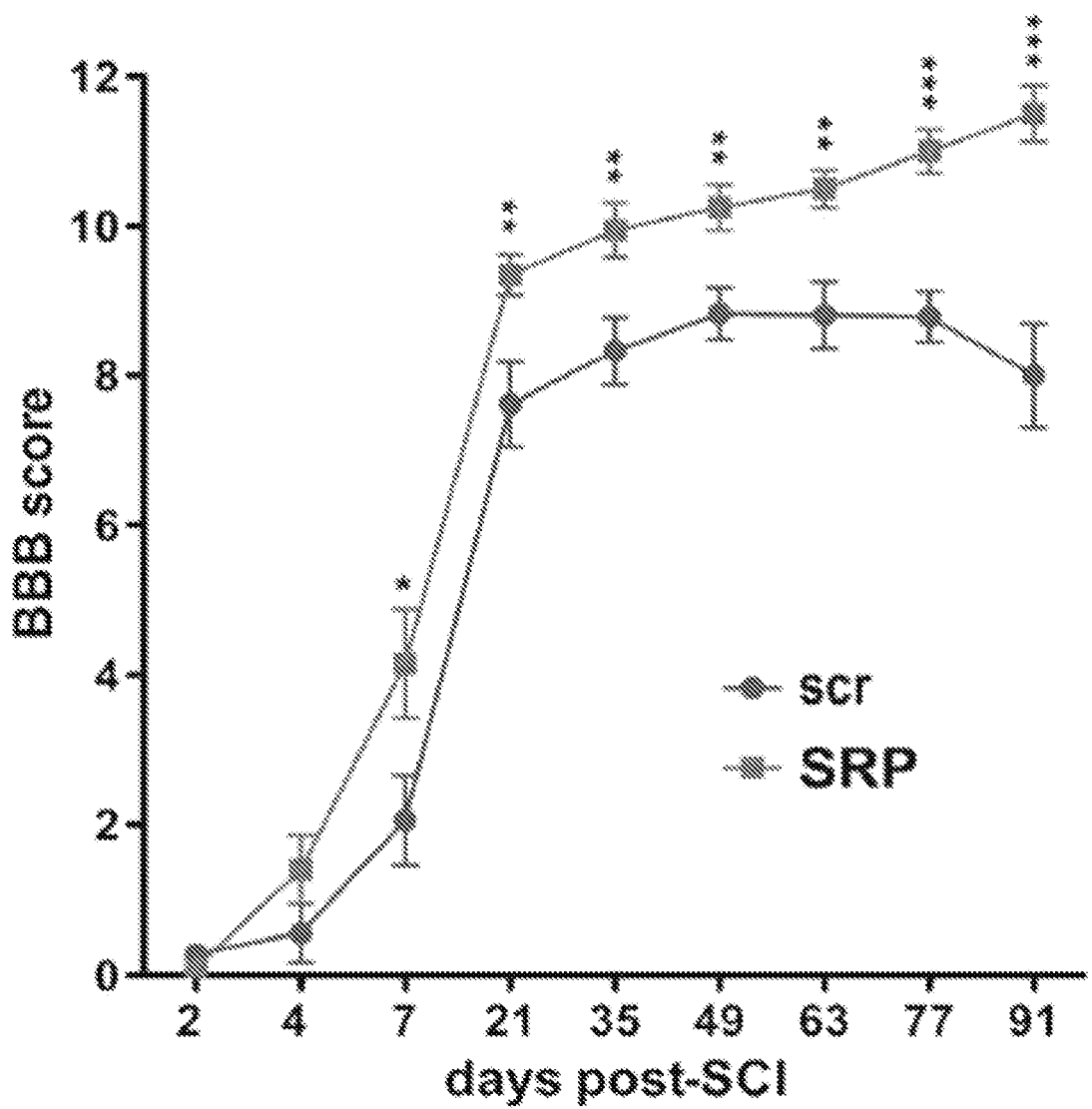
FIG. 18 shows improvement of hind limb motor function with SRP treatment following T8 contusive SCI. Animals were subcutaneously injected with SRP daily for one month beginning one day after SCI and assessed by the BBB open field locomotion test to evaluate hind limb motor function at the designated time points. SRP-treated animals showed significant improvement in hind limb locomotion as compared to scrambled peptide (scr)-treated animals over the entire observation period.
Figure 19F:
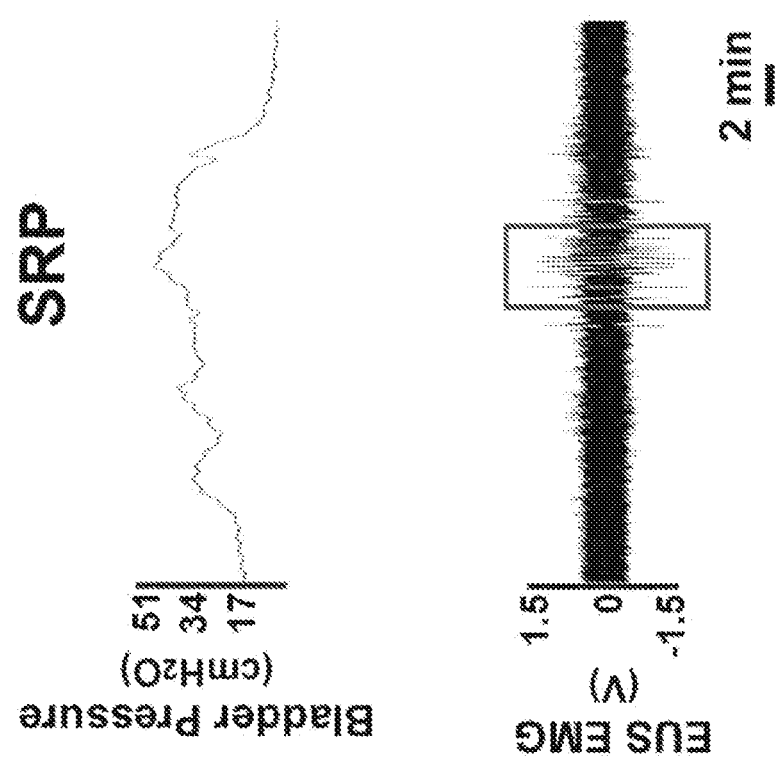
Figure 19G:
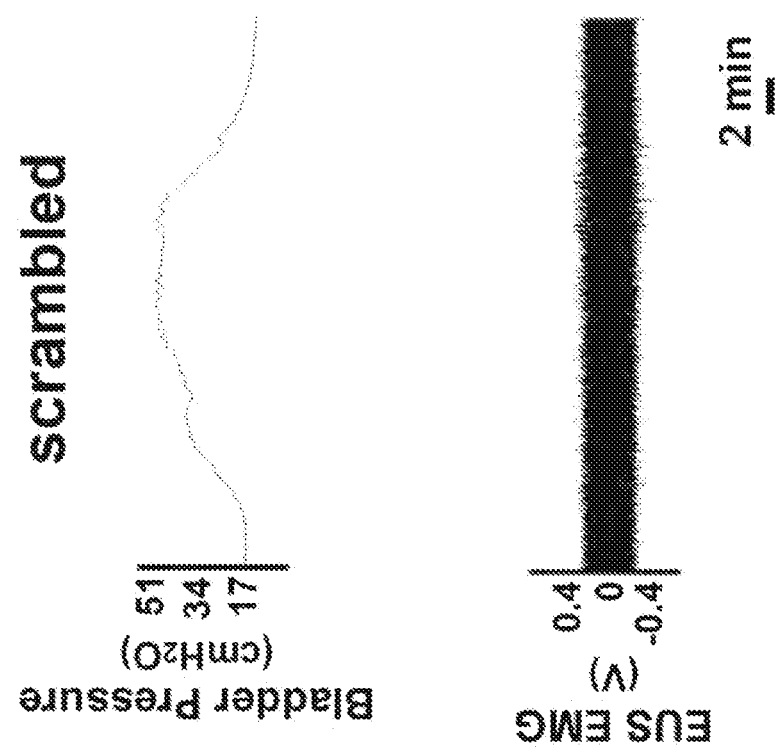

FIG. 18 shows improvement of hindlimb motor function with SRP treatment following T8 contusive SCI. Animals were subcutaneously injected with SRP daily for one month beginning one day after SCI and assessed by the BBB open field locomotion test to evaluate hind limb motor function at the designated time points. SRP-treated animals showed significant improvement in hind limb locomotion as compared to scrambled peptide (scr)-treated animals over the entire observation period. *$p<0.05$, $p<0.01$, and *$p<0.001$; two-way ANOVA. Values represent mean±SEM.

FIGS. 19A-G shows SRP treatment improved bladder function after T8 contusive SCI. Animals were treated daily with SRP for one month, beginning one day after SCI. Urodynamic analyses were conducted 3 months post-SCI. A representative cystometrograms (CMG) of three cycles of micturition events (red * indicates where micturition occurred) shows hyperactive bladder activity before reaching the voiding point in scrambled peptide-treated animals (A). SRP treatment (SRP) significantly reduced bladder hyperactivity (B). Statistical analysis revealed that SRP significantly reduced (C) residual volume, (D) the number of non-voiding contractions, and (E) the non-voiding contraction amplitude when compared to the scrambled peptide group (scr). *$p<0.05$, $p<0.01$ and *$p<0.001$ (two-tailed t test, n=8 per group). FIG. 19 (F and G) also shows SRP treatment improved bursting activities of external urethral sphincter (EUS) recorded by electromyogram (EMG) after T8 contusive SCI. EUS EMG recording were conducted 3 months post-SCI. The EUS EMG during the void period showed improvement in bursting activity indicated by red rectangle following SRP (G) when compared to the scrambled peptide (scrambled) group (F).

FIG. 20, panels A-B, shows that SRP significantly increased TBK1 and mitophagy adaptors in the spinal cord after SCI. SCI-upregulated SOCS3 was significantly reduced by SRP treatment (SRP) beginning one day after SCI (once per day) compared to the scrambled peptide group (scr). The protein levels of TBK1 and optineurin were significantly increased with SRP treatment. Additionally, significant activation of TBK1 and p62, as indicated by phospho-TBK1 Ser172 (p-TBK1) and phosphor-p62 Ser403 (p-p62) expression, was observed in SRP-treated SCI animals. (A). Graphs represented mean±SEM of six samples per group for the % to GAPDH (B). *$p<0.05$, $p<0.01$ and *$p<0.001$ compared to scrambled peptide animals (two-tailed t test, n=3 per group).

Figure 21:
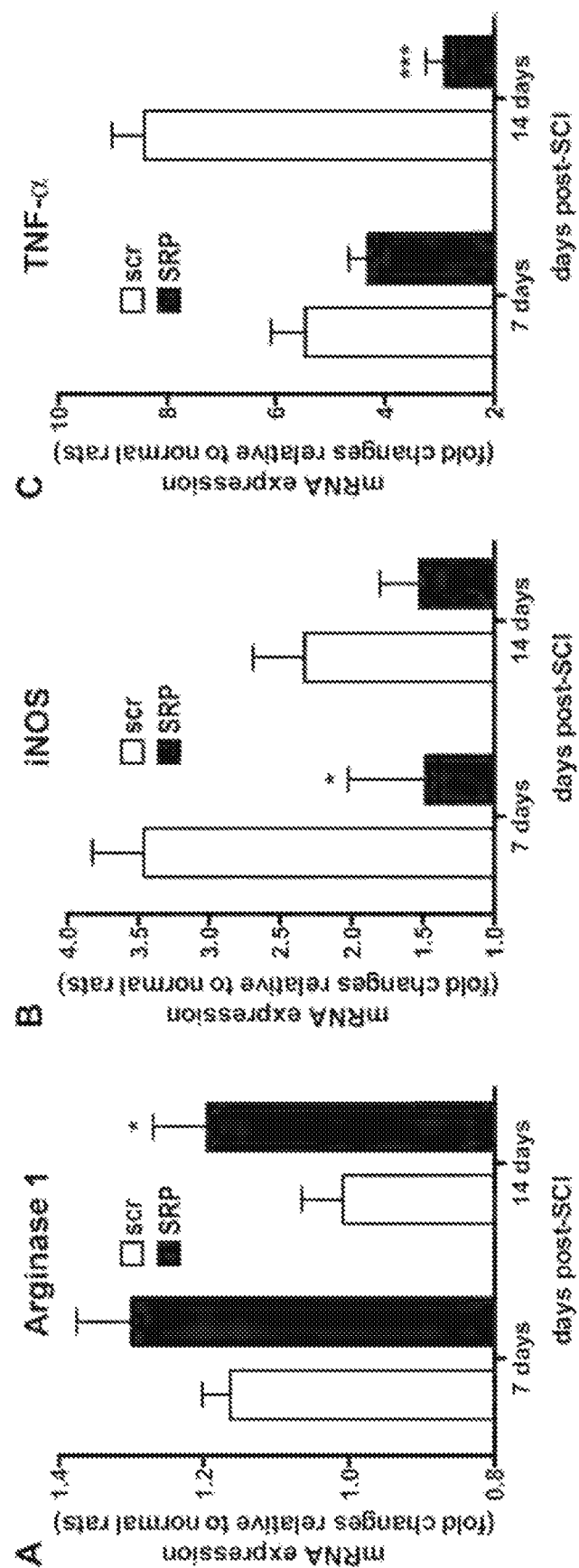
FIG. 21, panels A-C, shows qRT-PCR analyses of markers for pro-vs. anti-inflammatory macrophages in spinal cord segments caudal to the injury site. Rats were treated once per day beginning one day after SCI with SRP or scrambled peptide (scr) and mRNA was then harvested and analyzed by qRT-PCR. As shown, SRP treatment increased arginase 1 (A), but decreased iNOS (B) expression, at both 7 and 14 days post-SCI. C. Notably, SRP decreased TNF-α expression at 7 days post-SCI, which was even more pronounced at 14 days post-SCI.

FIG. 21, panels A-C, shows qRT-PCR analyses of markers for pro-vs. anti-inflammatory macrophages in spinal cord segments caudal to the injury site. Rats were treated once per day beginning one day after SCI with SRP or scrambled peptide (scr) and mRNA was then harvested and analyzed by qRT-PCR. As shown, SRP treatment increased arginase 1 (A), but decreased iNOS (B) expression, at both 7 and 14 days post-SCI. C. Notably, SRP decreased TNF-α expression at 7 days post-SCI, which was even more pronounced at 14 days post-SCI. *$p<0.05$ and ***$p<0.001$ compared to scrambled peptide-treated animals, two-way ANOVA with Bonferroni multiple analyses, mean±SEM, n=3 per group.

Figure 22:
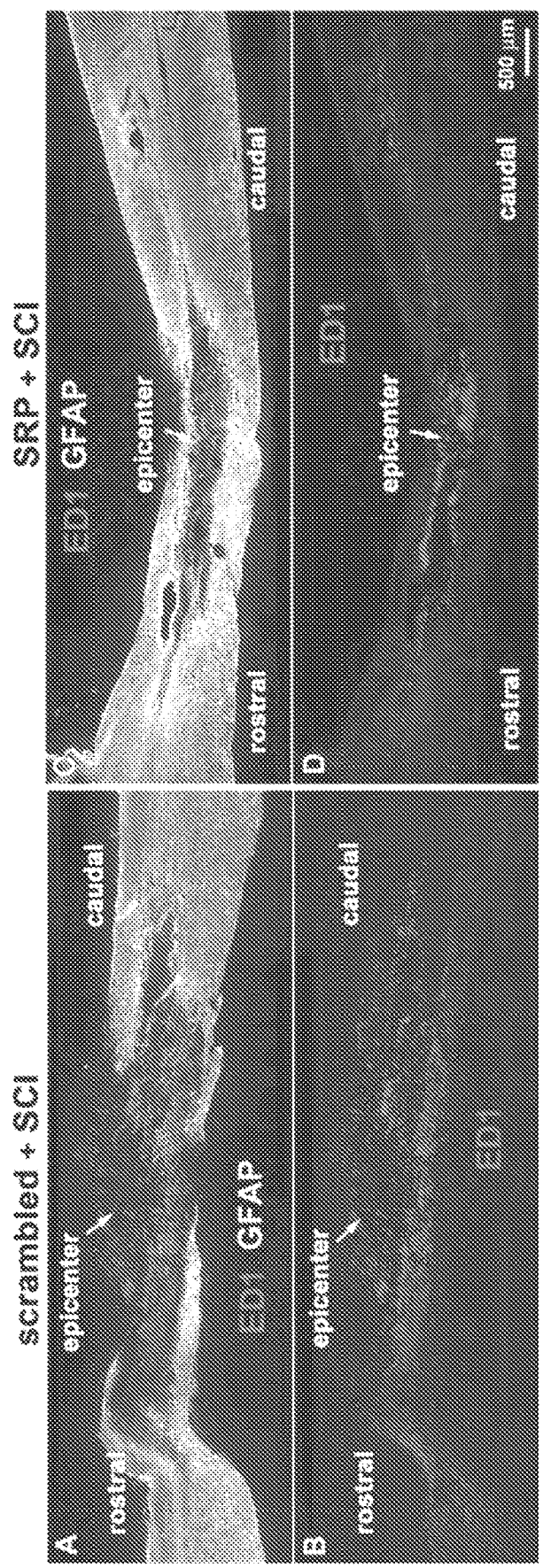
FIG. 22, panels A-D, shows SRP treatment robustly decreased SCI-increased ED1+macrophages/microglia. SRP treatment beginning one day after SCI was administered for 30 consecutive days and then spinal cords were harvested three months post-SCI for double immunolabeling of ED1 and GFAP. As shown, SRP treatment blocked SCI-induced upregulation of ED1+macrophages (C, D), but preserved more GFAP+ tissues (A, B) in the areas surrounding the lesion epicenter when compared to scrambled peptide (scrambled)-treated groups.

FIG. 22, panels A-D, shows SRP treatment robustly decreased SCI-increased ED1+macrophages/microglia. SRP treatment beginning one day after SCI was administered for 30 consecutive days and then spinal cords were harvested three months post-SCI for double immunolabeling of ED1 and GFAP. As shown, SRP treatment blocked SCI-induced upregulation of ED1+macrophages (C, D), but preserved more GFAP+tissues (A, B) in the areas surrounding the lesion epicenter when compared to scrambled peptide (scrambled)-treated groups.

Figure 23:
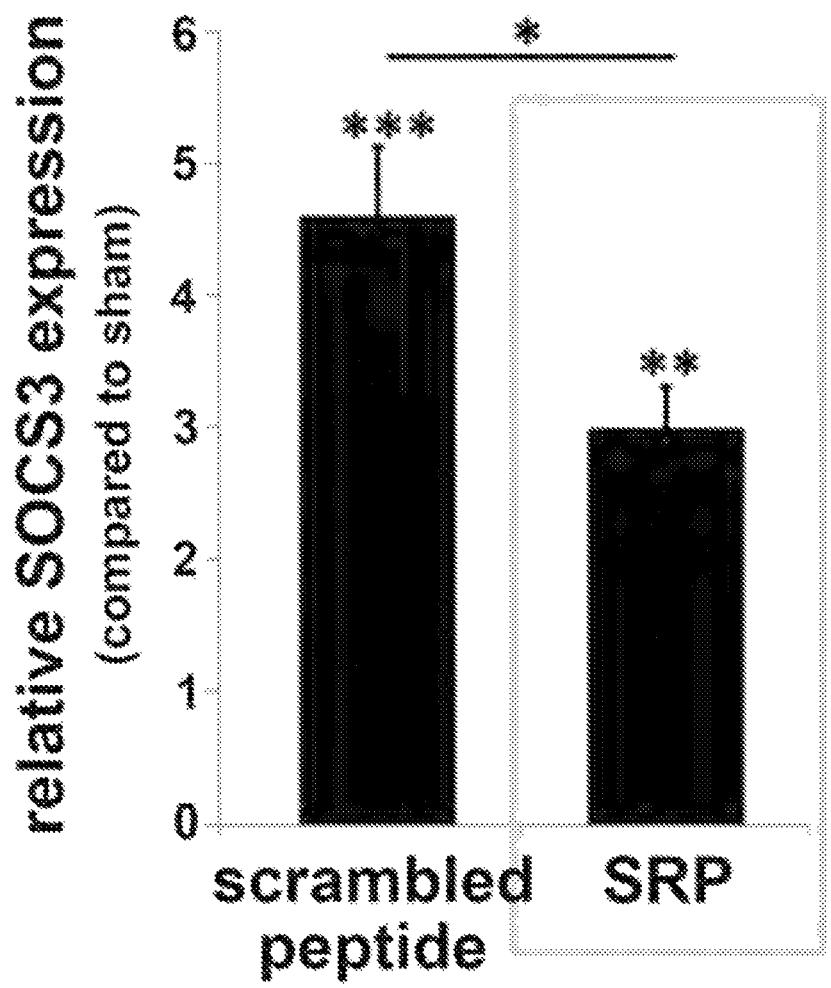
FIG. 23 shows SRP significantly reduced SOCS3 levels in the sciatic nerve after sciatic nerve transection. The sciatic nerve transection-upregulated SOCS3 was significantly reduced by SRP treatment (SRP) beginning immediately after sciatic nerve transection for 4 consecutive days (once per day).

FIG. 23 shows SRP significantly reduced SOCS3 levels in the sciatic nerve after sciatic nerve transection. The sciatic nerve transection-upregulated SOCS3 was significantly reduced by SRP treatment (SRP) beginning immediately after sciatic nerve transection for 4 consecutive days (once per day). $p<0.01$ and *$p<0.001$ compared to normal animals, and *p<0.05 compared to scrambled peptide treated animals (two-tailed t test, n=4 per group).

Example 3

This Example describes additional in vitro and in vivo work with the CSPG reduction peptide (CRP) described in Example 1.

FIG. 24 shows that applied CRP is found in the lysosome of Neu7 astrocytes and provides the results of an in vitro assays that demonstrates the concept of lysosomal target domain in CRP. Such an in vitro assay was used to demonstrate the co-localization of FITC-CRP and lysosomal marker (LAMP1). Representative images indicate that FITC-CRP is brought to lysosomes (LAMP1+) for degradation after entering Neu7 cells (arrow).

Figure 25:
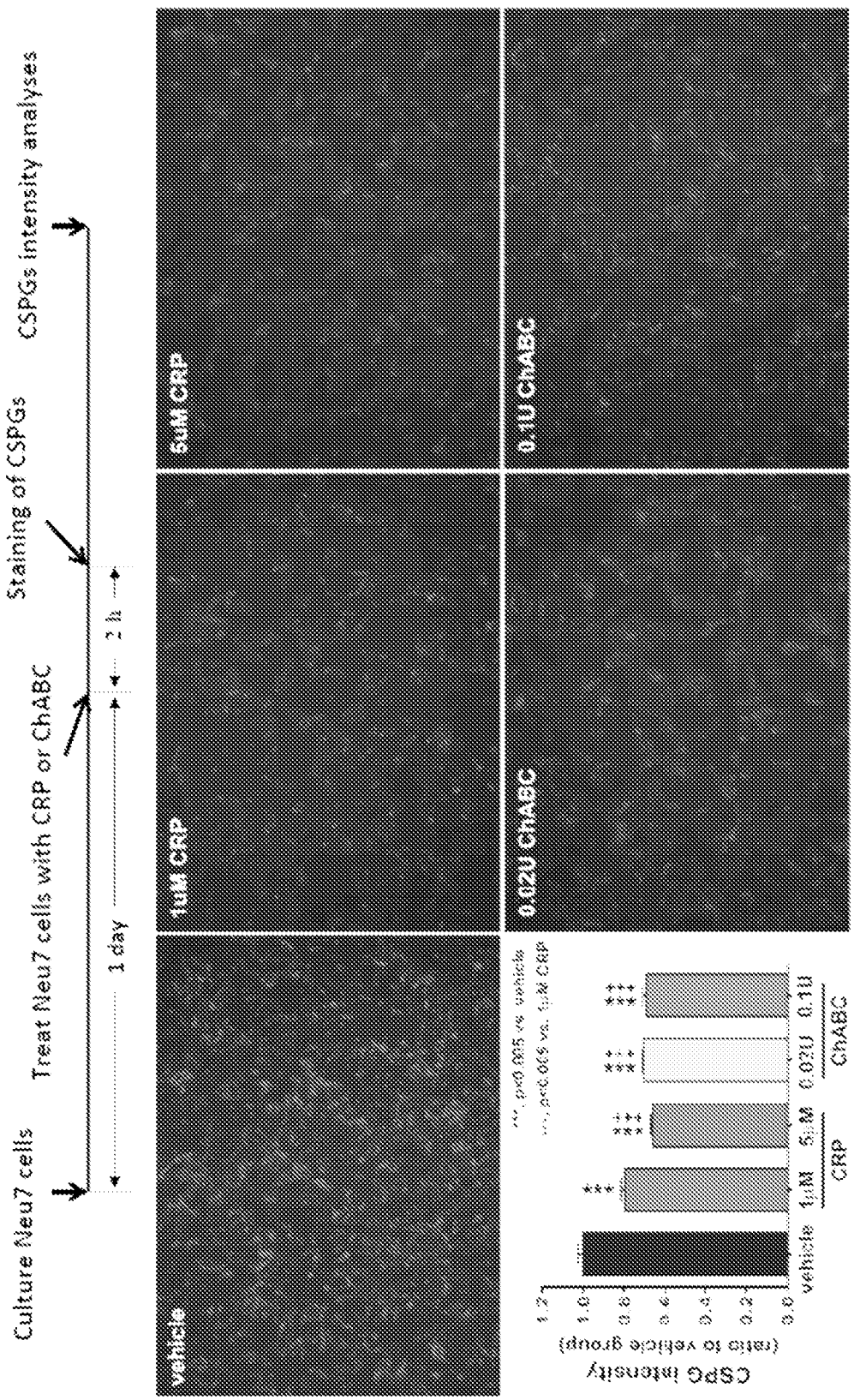
FIG. 25 shows that CRP significantly decreases Neu7-produced CSPGs. In particular.
Figure 26A:
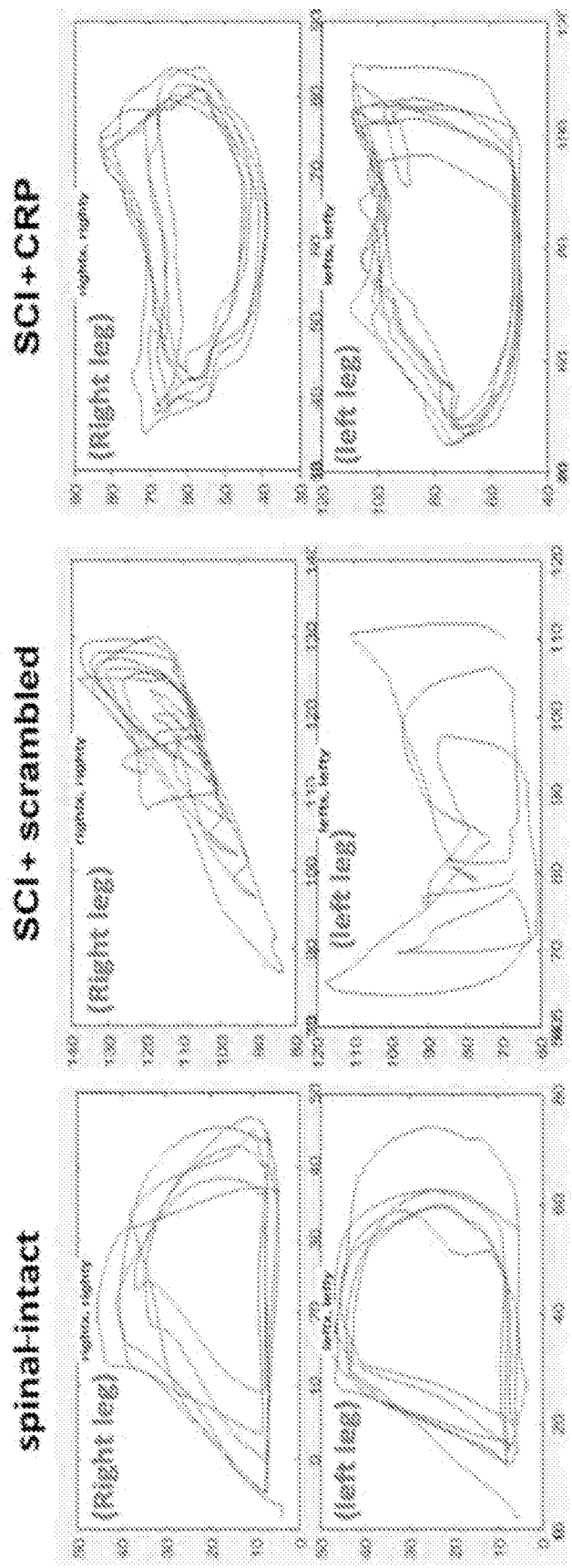
FIG. 26A-G show that CRP treatment improves gait patterns after SCI in rats. In particular
Figures 26B, 26C, 26D:
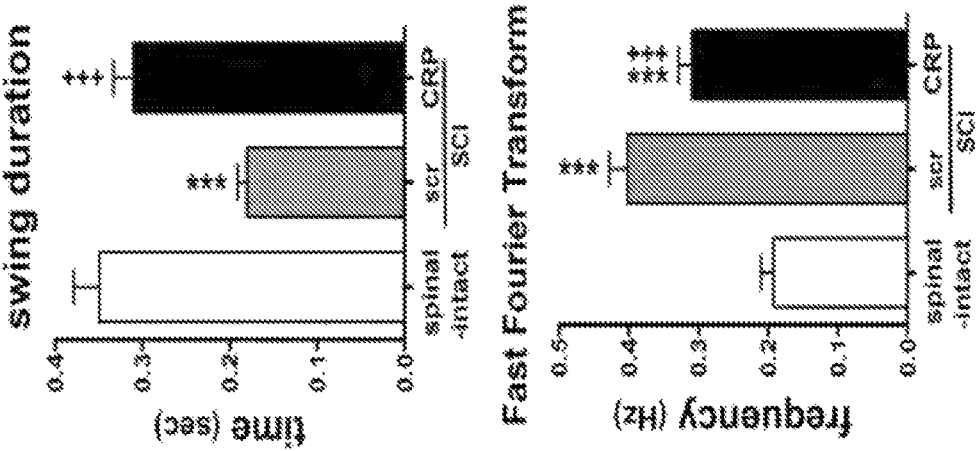
Figures 26E, 26F, 26G:
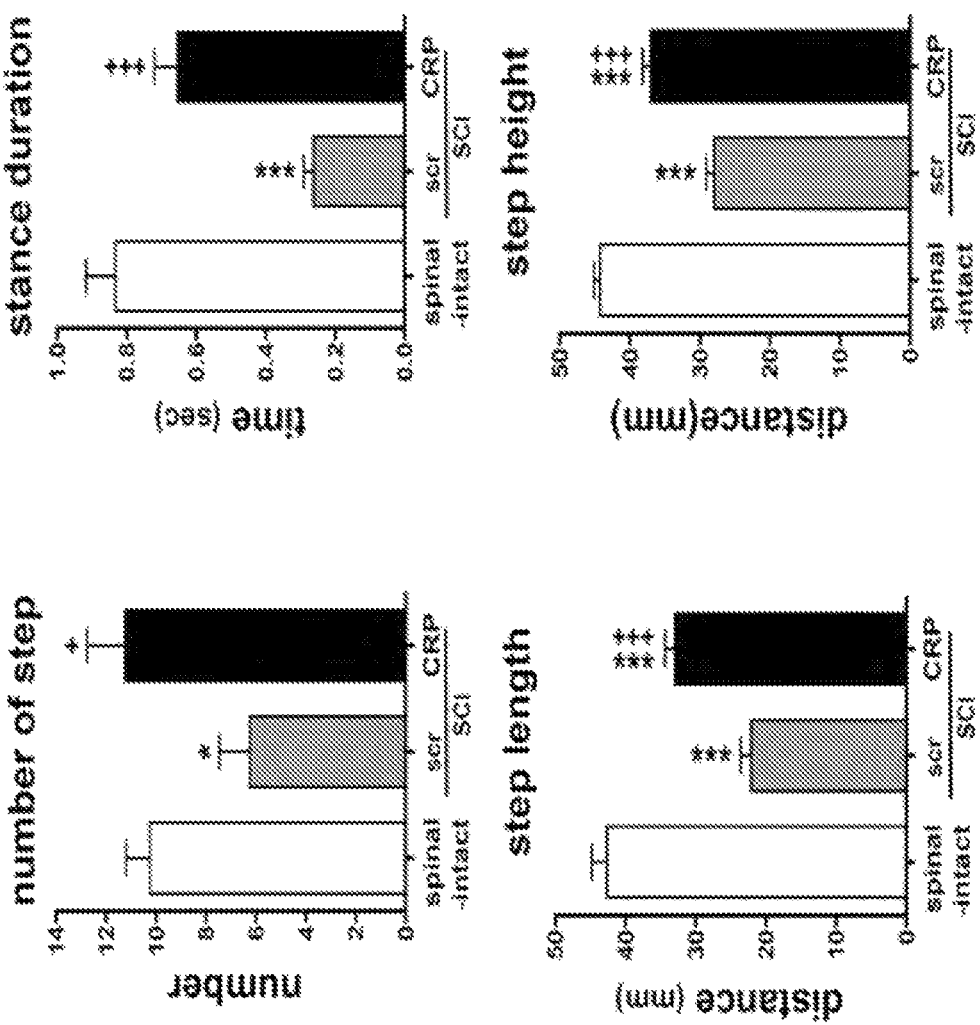
Figure 27A:
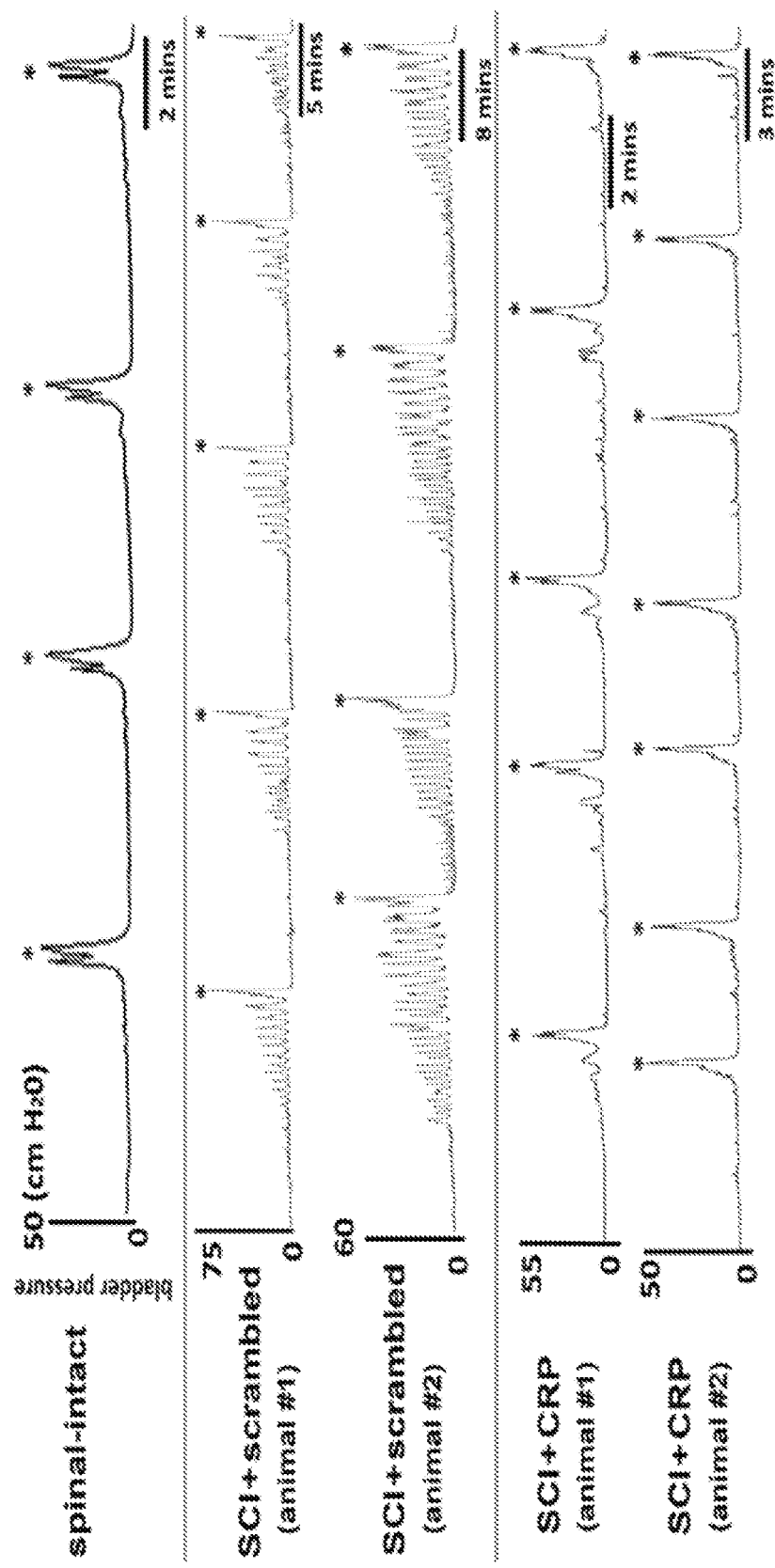

FIG. 25 shows that CRP significantly decreases Neu7-produced CSPGs. In particular, FIG. 25 shows that CRP significantly reduces CSPG produced by Neu7 cells to a comparable level what ChABC does. Note there is also a dosage response by CRP application.

FIGS. 26A-G show that CRP treatment improves gait patterns after SCI in rats. In particular, FIG. 26A-G show Kinematics assessment in SCI rats. (A) Representative total of hindlimb movement trajectories for spinal-intact, SCI+ scrambled peptide (scr) and SCI+CRP groups at 3 months post-SCI. (B-G) CRP treatment significantly improved several parameters of gait pattern with trajectories more consistent to what the spinal-intact animals did, when compared to scr treatment. *, P<0.05; ***, P<0.001 when compared to the spinal-intact group; +, P<0.05; +++, P<0.001 when compared to scr group. N=6 to 8 per group.

FIGS. 27A-H show that CRP treatment improves bladder function after SCI. (A) Representative cystometrograms (CMG) with micturition (voiding) events (indicated by asterisk) for spinal-intact, SCI+scrambled peptide (scr) and SCI+CRP groups at 3 months post-SCI. (B~H) CRP treatment reduces hyperactive bladder and improve CMG parameters including lower voiding pressure and smaller bladder capacity when compared to scr application after T8 SCI. *, P<0.05; , P<0.01; *, P<0.001 when compared to the spinal-intact group; +++, P<0.001 when compared to the scr group. N=6 to 8 per group.

Figure 28:
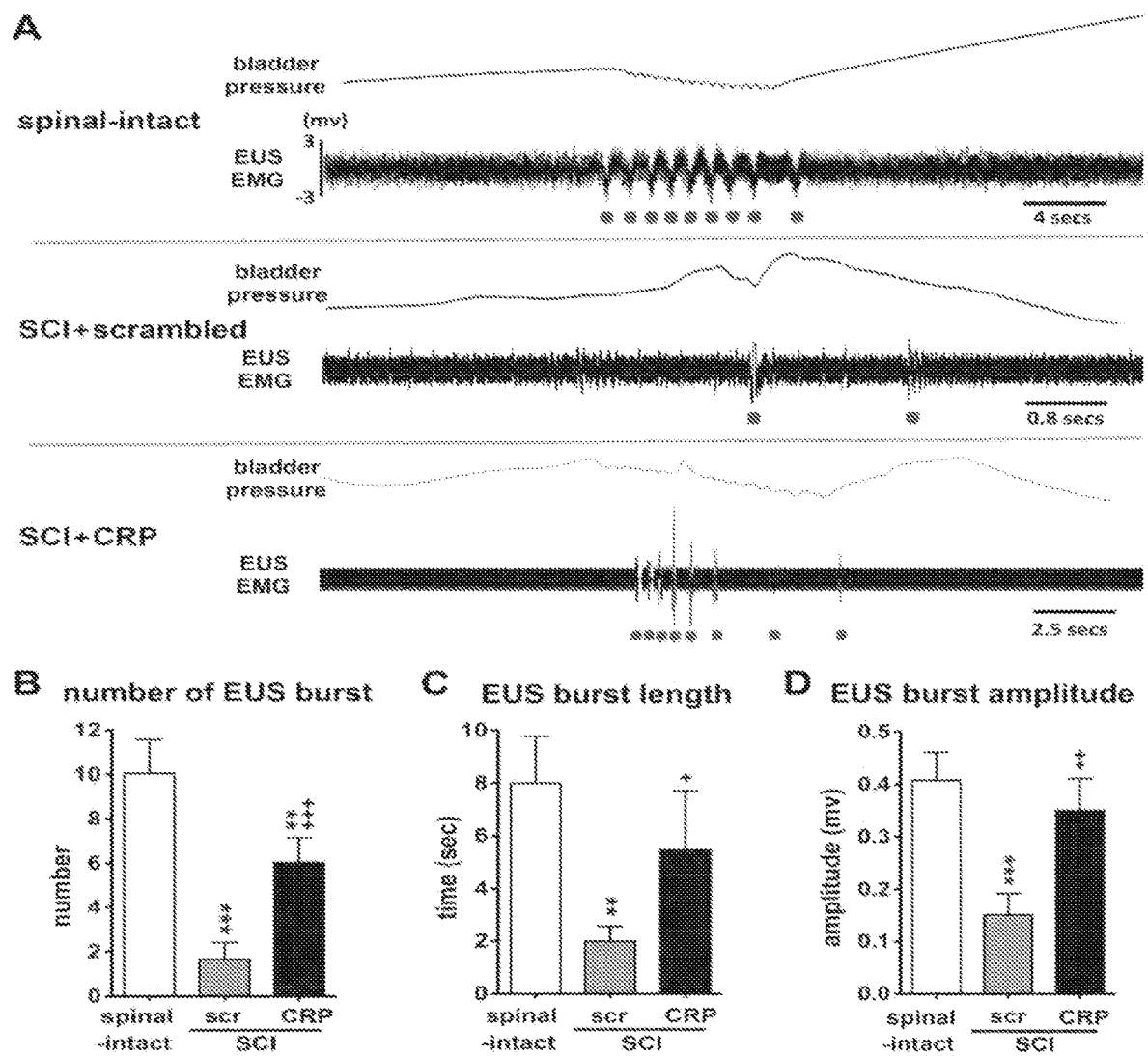
FIG. 28, panels A-D, shows that CRP treatment improves EUS EMG activity during the void after SCI (more bursting number and larger bursting amplitude). (A) Representative cystometrograms (CMG) with external urethral sphincter (EUS) electromyogram (EMG) recordings at micturition events for spinal-intact, SCI+scrambled peptide (scr) and SCI+CRP groups at 3 months post-SCI. (B~D) CRP treatment improves EUS bursting activity when compared to scr application after T8 SCI. The red dot indicates bursting activity.

FIG. 28, panels A-D, shows that CRP treatment improves EUS EMG activity during the void after SCI (more bursting number and larger bursting amplitude). (A) Representative cystometrograms (CMG) with external urethral sphincter (EUS) electromyogram (EMG) recordings at micturition events for spinal-intact, SCI+scrambled peptide (scr) and SCI+CRP groups at 3 months post-SCI. (B~D) CRP treatment improves EUS bursting activity when compared to scr application after T8 SCI. The red dot indicates bursting activity. , P<0.01; *, P<0.001 when compared to the spinal-intact group; +, P<0.05; ++, P<0.01; +++, P<0.001 when compared to the scr group. N=6 to 8 per group.

Figure 29:
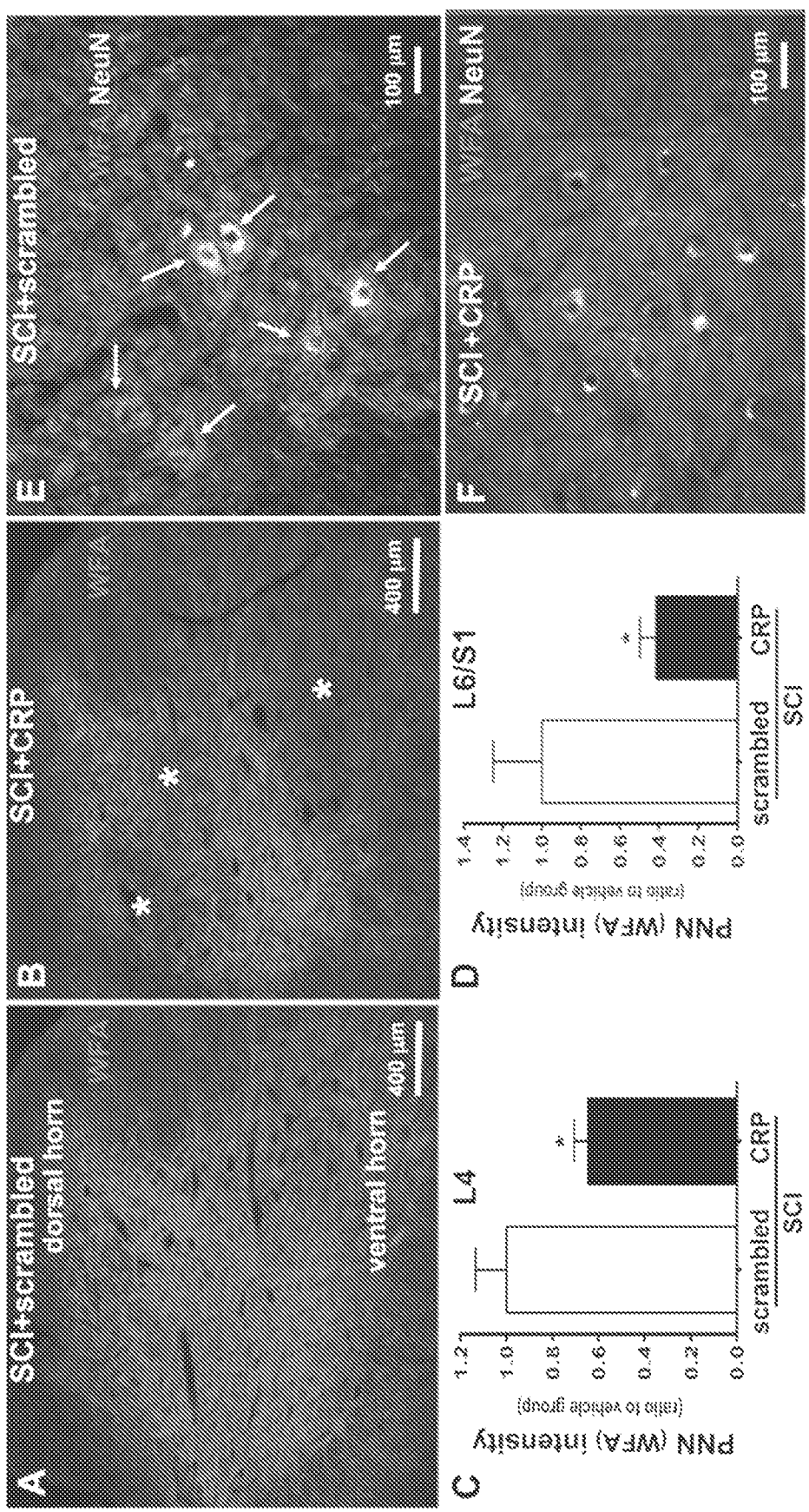
FIG. 29, panels A-F, shows that CRP treatment reduced PNN in lumbosacral spinal cord after T8 SCI, and particularly shows the anatomical assessments of perineuronal nets (PNN) in SCI rats. (A, B) Representative L4 spinal cord transverse images show CRP treatment reduces overall PNN in grey matter of lumbar spinal cord neurons at 3 months post SCI. Notice areas with clear decreased WFA staining of the PNN (asterisk). (C, D) Statistical analyses show the significant reduction of PNN at both L4 and L6/S1 levels in CRP group when compared to the scrambled peptide group. (E, F) Representative higher power immunostaining images of the ventral horn of transverse L4 sections show the strong PNN intensity (arrow) surrounding the NeuN+ cells in scr treated SCI rats (E), while CRP treatment reduces them (F).

FIG. 29, panels A-F, shows that CRP treatment reduced PNN in lumbosacral spinal cord after T8 SCI, and particularly shows the anatomical assessments of perineuronal nets (PNN) in SCI rats. (A, B) Representative L4 spinal cord transverse images show CRP treatment reduces overall PNN in grey matter of lumbar spinal cord neurons at 3 months post SCI. Notice areas with clear decreased WFA staining of the PNN (asterisk). (C, D) Statistical analyses show the significant reduction of PNN at both L4 and L6/S1 levels in CRP group when compared to the scrambled peptide group. (E, F) Representative higher power immunostaining images of the ventral horn of transverse L4 sections show the strong PNN intensity (arrow) surrounding the NeuN+ cells in scr treated SCI rats (E), while CRP treatment reduces them (F). *, P<0.05 when compared to the scr treatment. N=8 per group.

Figure 30:
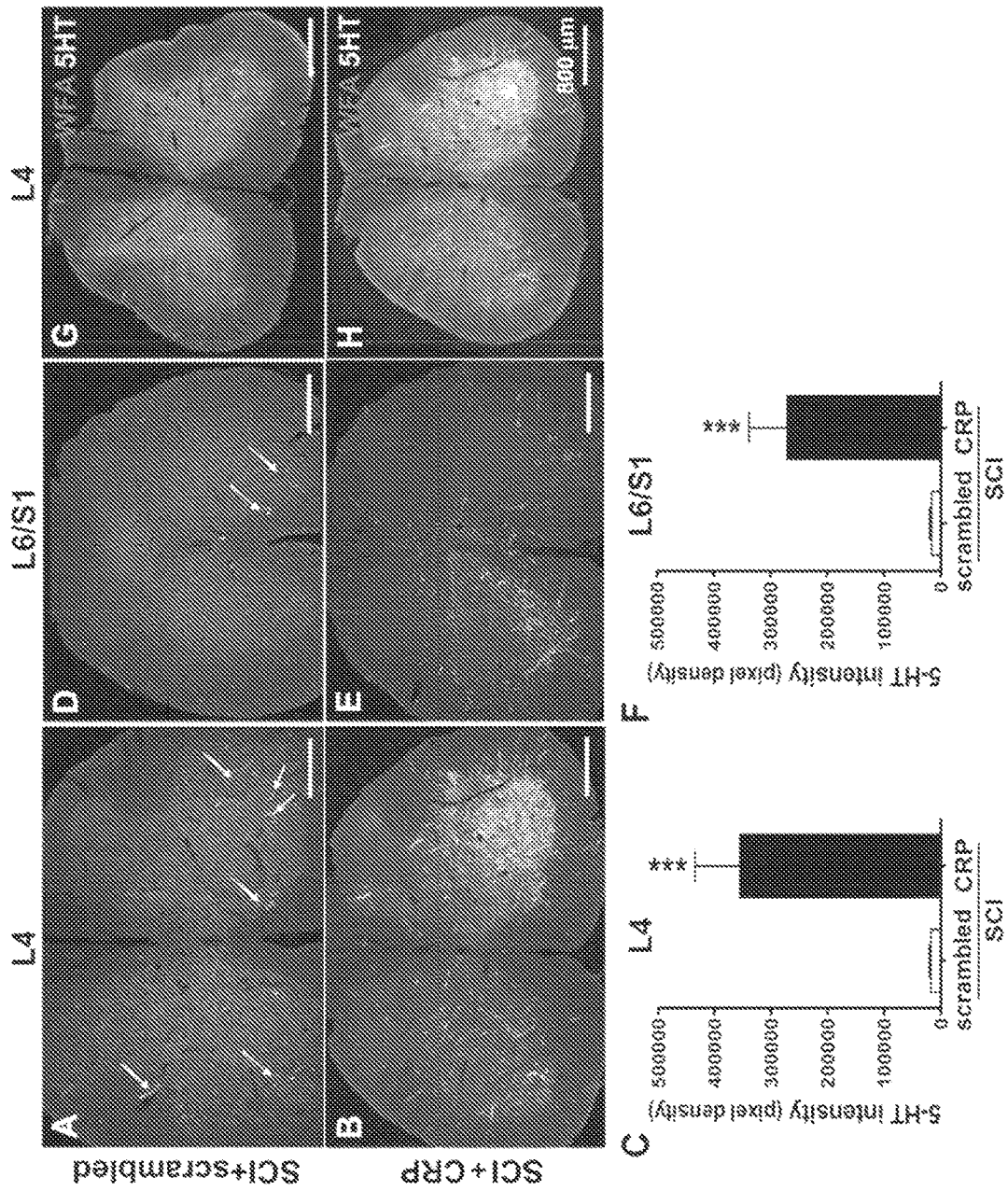
FIG. 30, panels A-F, shows that CRP enhances serotonergic fibers sprouting in lumbrosacral spinal cord. In particular, 5HT immunoreactivity in lumbosacral level after SCI. (A-F) Representative spinal cord transverse images show that pretty low amount of 5HT fibers (arrow) found at both L4 (A-C) and L6/S1 (D-F) levels after severe contusive SCI, while CRP treatment significantly increases immunoreactivity of 5HT fibers. (G, H) Representative images with double staining of
WFA and 5HT showing areas of clear decreased PNN indicated by WFA+, in areas of intense 5-HT sprouting (asterisk).

FIG. 30, panels A-F, shows that CRP enhances serotonergic fibers sprouting in lumbrosacral spinal cord. In particular, 5HT immunoreactivity in lumbosacral level after SCI. (A-F) Representative spinal cord transverse images show that pretty low amount of 5HT fibers (arrow) found at both L4 (A-C) and L6/S1 (D-F) levels after severe contusive SCI, while CRP treatment significantly increases immunoreactivity of 5HT fibers. (G, H) Representative images with double staining of WFA and 5HT showing areas of clear decreased PNN indicated by WFA+, in areas of intense 5-HT sprouting (asterisk). ***, P<0.001 when compared to the scrambled peptide treatment. N=8 per group.

Figure 31:
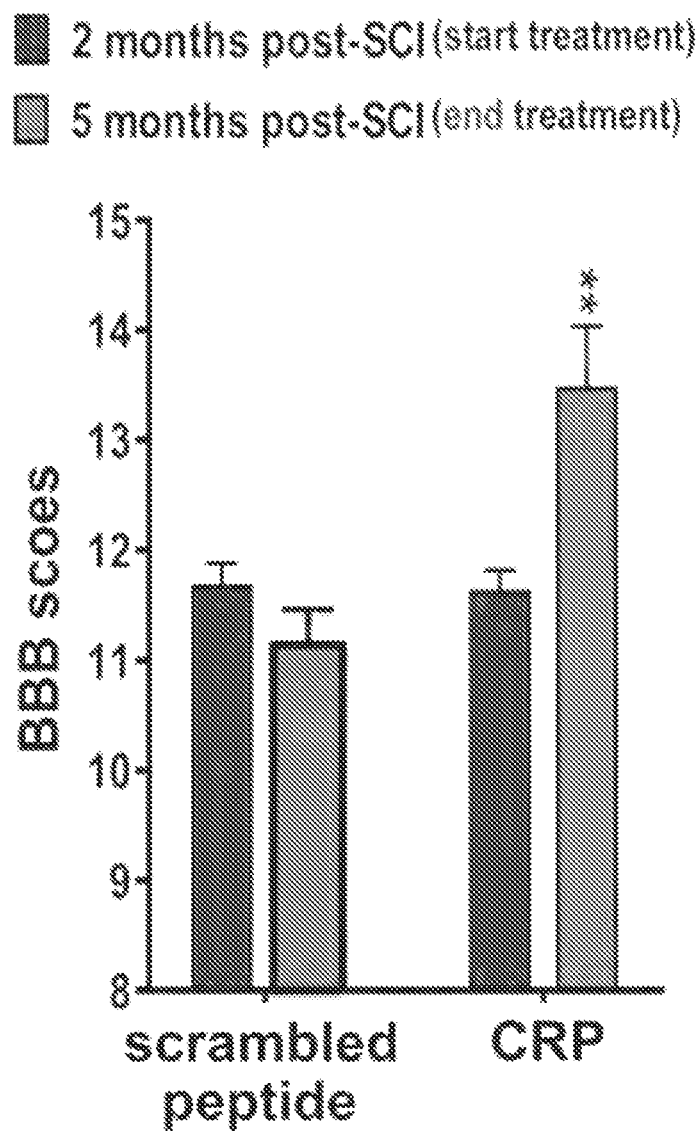
FIG. 31 shows that CRP improves locomotion after chronic SCI. In particular.

FIG. 31 shows that CRP improves locomotion after chronic SCI. In particular, FIG. 31 shows BBB scores that show that CRP treatment improves hindlimb locomotion after chronic SCI (N=6 to 8 animals per group). Note the significant increases in BBB locomotion scale by CRP at 5 months post SCI when compared to what at the time (two months post SCI) of beginning treatment.

Figure 32:
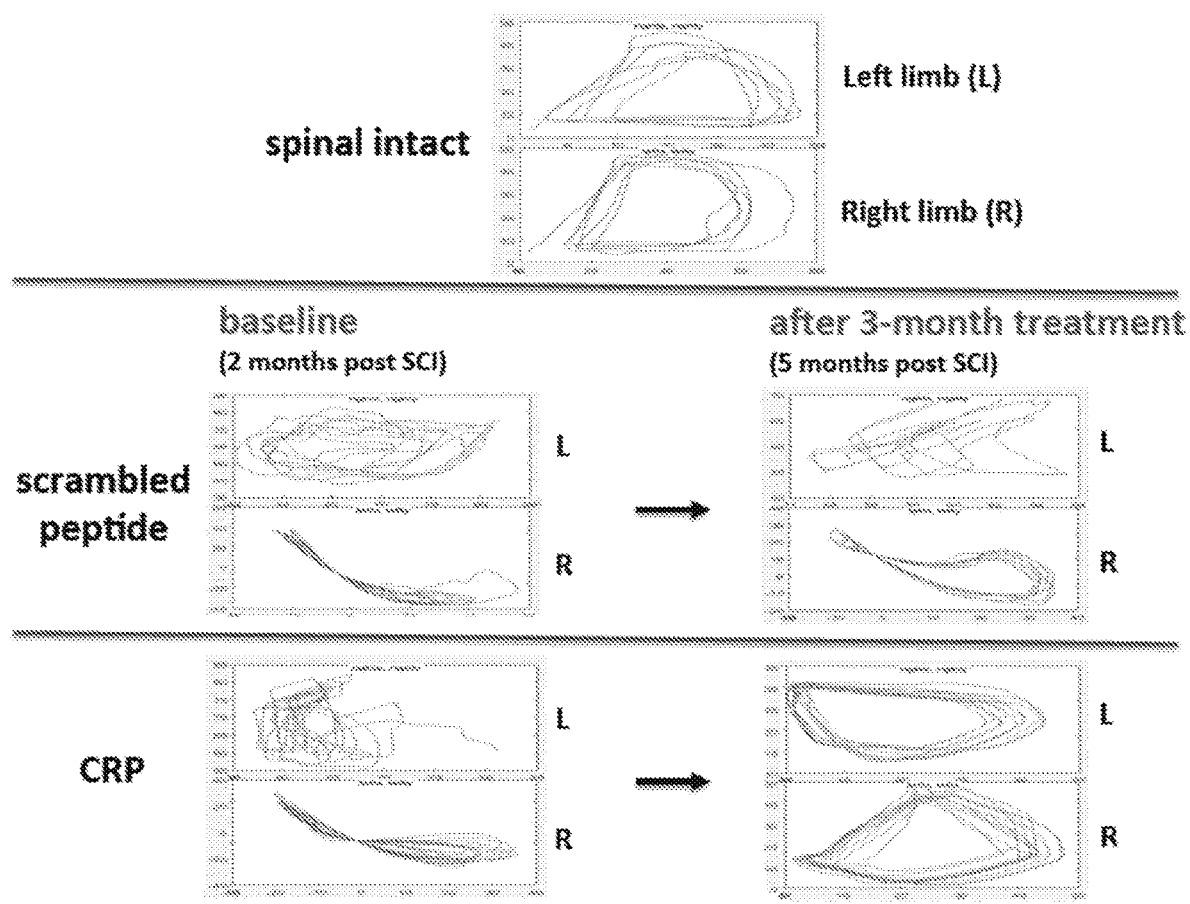
FIG. 32 shows that CRP treatment improves gait patterns after chronic SCI. In particular.

FIG. 32 shows that CRP treatment improves gait patterns after chronic SCI. In particular, FIG. 32 shows representative 2D trajectory patterns indicated CRP treatment improved stepping kinematic of both hindlimbs by CRP at 5 months post SCI when it compared to what at the time (two months post SCI) of beginning treatment.

Figure 33:
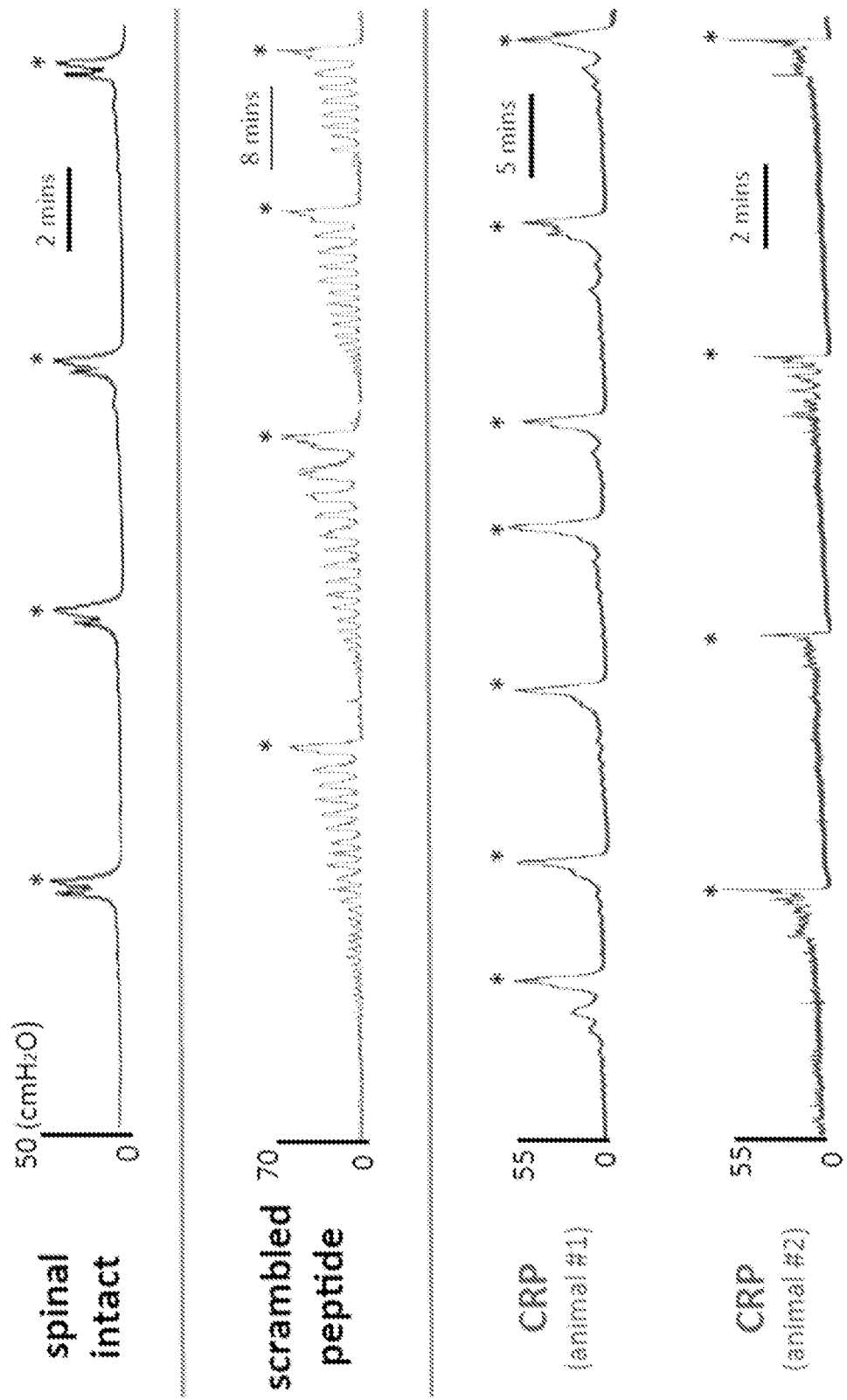
FIG. 33 shows that CRP treatment improves bladder function after chronic SCI. In particular.

FIG. 33 shows that CRP treatment improves bladder function after chronic SCI. In particular, FIG. 33 shows representative cystometrograms (CMG) data indicated 3 months of CRP treatment (starting at 2 months post SCI) can reduce hyperactive bladder and improve other CMG parameters.

Figure 34:
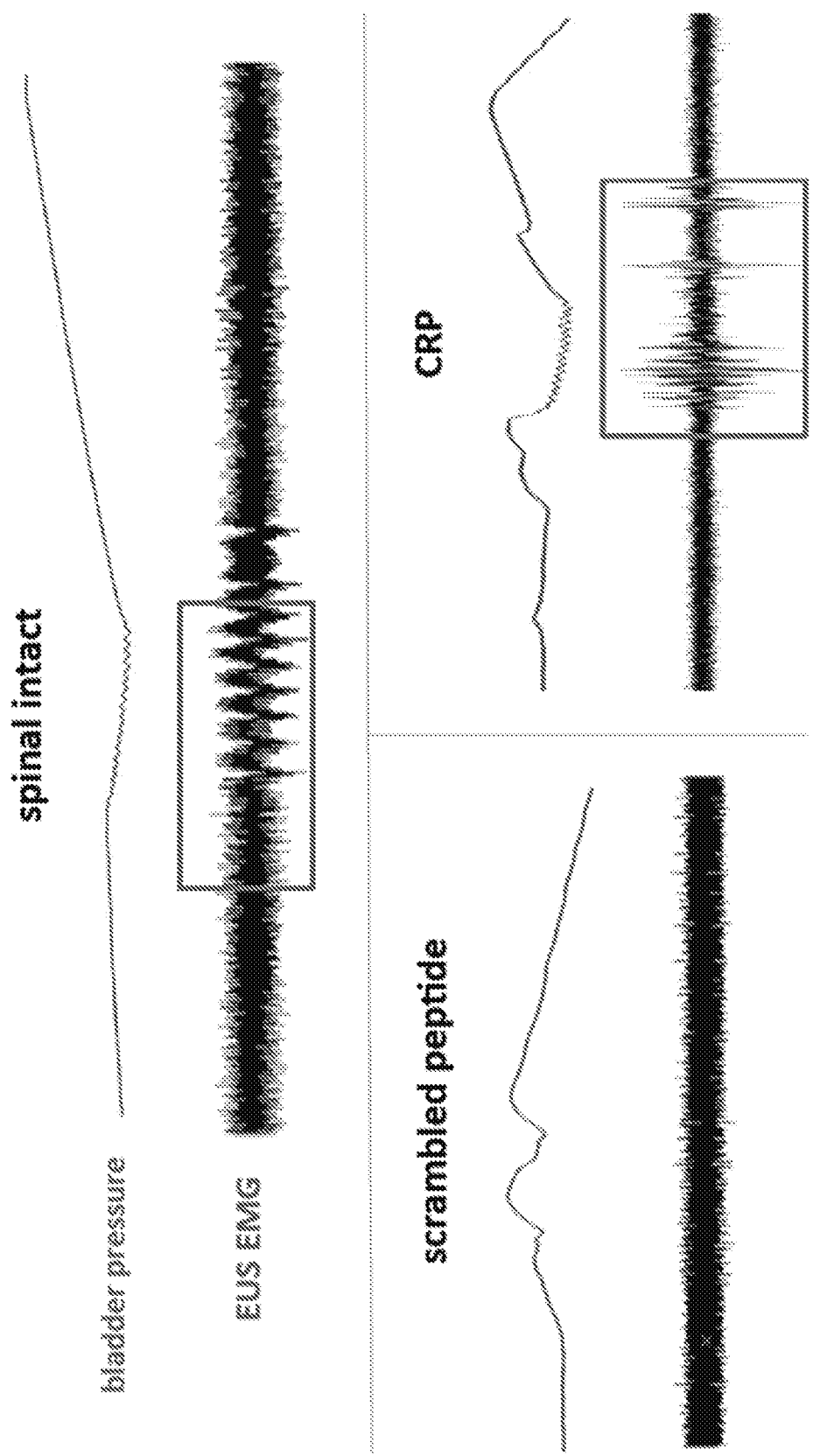
FIG. 34 shows that CRP treatment improves EUS EMG activity during the void after chronic SCI. In particular.

FIG. 34 shows that CRP treatment improves EUS EMG activity during the void after chronic SCI. In particular, FIG. 34 shows representative urodynamic and external urethral sphincter (EUS) electromyogram (EMG) recordings indicated CRP treatment can improve EUS bursting activity during the void period when compared to the scrambled peptide application after chronic SCI. The box area indicates the bursting activity.

FIG. 35 shows CRP enhances 5HT fibers sprouting in lumbar cord after chronic SCI. In particular, FIG. 35 shows representative spinal cord transverse images that CRP treatment can enhance 5HT+nerve fibers sprouting in lumbosacral level when compared to the scrambled peptide treatment after chronic SCI.

Figure 36:
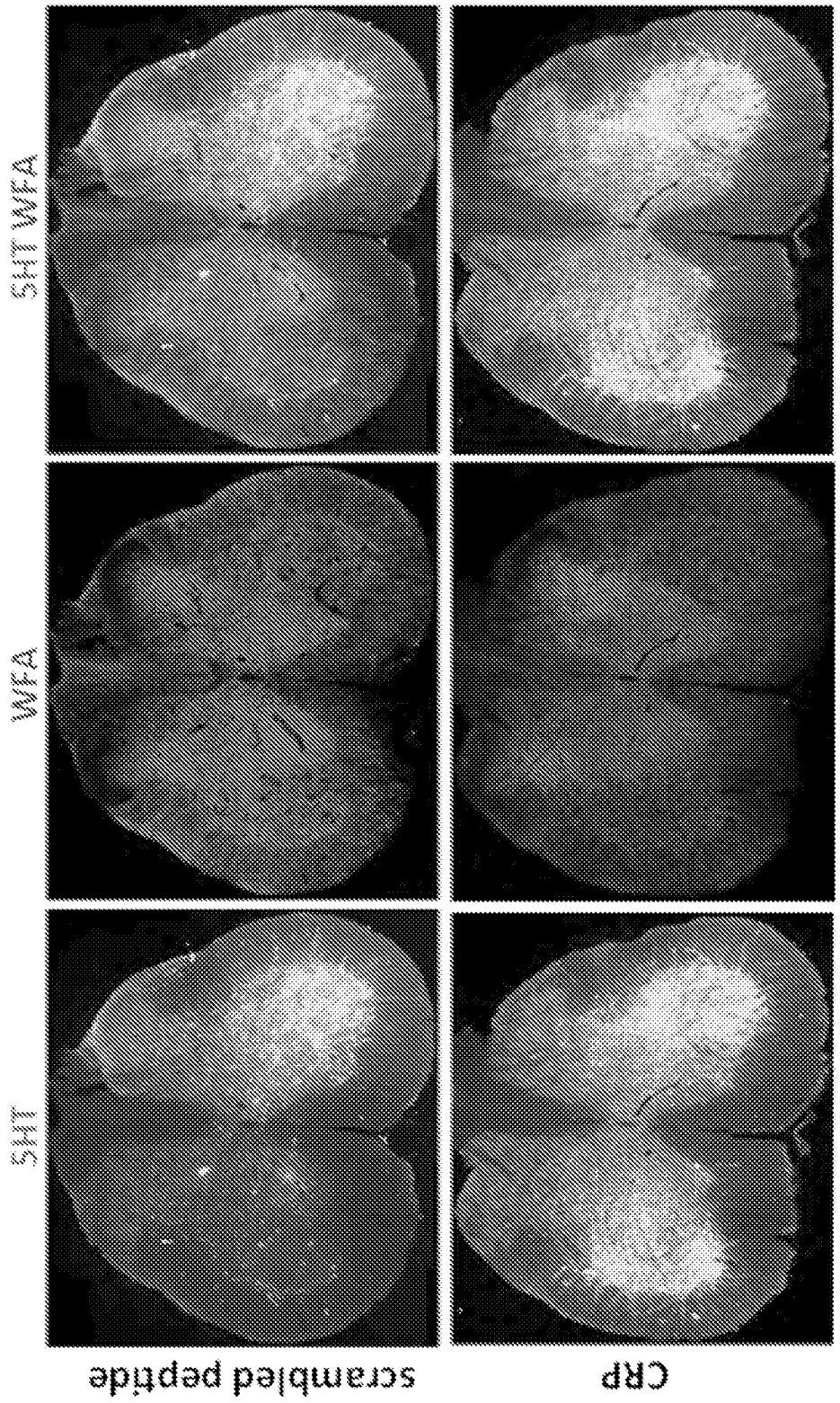
FIG. 36 shows CRP treatment enhances 5HT sprouting but decreases PNN in lumbar cord after chronic SCI. In particular.

FIG. 36 shows CRP treatment enhances 5HT sprouting but decreases PNN in lumbar cord after chronic SCI. In particular, FIG. 36 shows 5HT immunoreactivity in lumbosacral level after chronic SCI. Representative spinal cord transverse images show that low amount of 5HT fibers found at L4 levels after contusive SCI, while CRP treatment significantly increases immunoreactivity of 5HT fibers. Representative images with double staining of WFA and 5HT shows areas with robustly decreased PNN (indicated by WFA+) but enhanced 5-HT sprouting.

Figure 37:
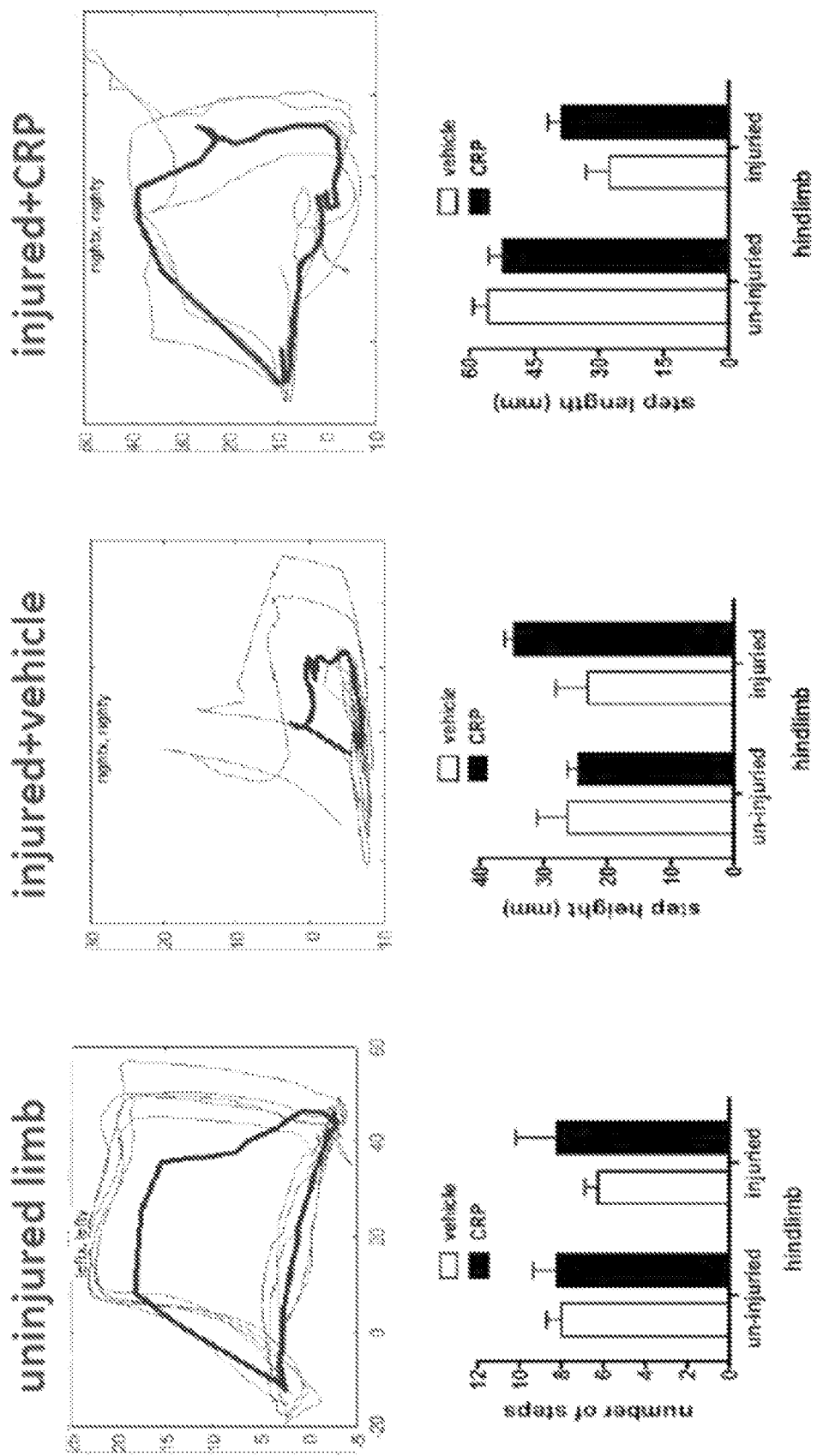
FIG. 37 shows CRP treatment improves gait patterns after sciatic nerve injury. In particular.

FIG. 37 shows CRP treatment improves gait patterns after sciatic nerve injury. In particular, FIG. 37 shows the acute treatment of CRP with allograft of a peripheral nerve segment (2 cm) improved the stepping performance of hindlimbs at 3 months after complete sciatic nerve transection. The representative 2D trajectory and improved kinematics parameters indicated CRP treated animals improved the stepping more toward to what the uninjured limb did, while compared to the vehicle treated animals. The CRP was delivered through subcutaneous injection near the injured site (once per day) staring immediately after surgery for 3 months.

All publications and patents mentioned in the specification and/or listed below are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope described herein.

We claim:

1. A method of promoting motor function recovery and/or bladder function recovery, after spinal cord injury caused by trauma in a subject comprising: administering a suppressor of cytokine signaling 3 (SOCS3) reduction peptide (SRP), or a nucleic acid encoding the SRP, to a subject with a spinal cord injury caused by trauma, wherein the SRP comprises the amino acid sequence of SEQ ID NO:90.

2. The method of claim 1, wherein the administering is conducted within about 24 hours of the spinal cord injury.

3. The method of claim 1, wherein the administering is conducted after at least two days of the spinal cord injury.

4. The method of claim 1, wherein the administering is conducted at least one week after the spinal cord injury.

5. The method of claim 1, wherein the administering is conducted at least two weeks after the spinal cord injury.

6. The method of claim 1, wherein the administering is conducted at least one month after the spinal cord injury.

7. The method of claim 1, wherein the administering is conducted at least two months after the spinal cord injury.

* * * * *

```
                           SEQUENCE LISTING

Sequence total quantity: 90
SEQ ID NO: 1            moltype = AA  length = 11
FEATURE                 Location/Qualifiers
source                  1..11
                        mol_type = protein
                        organism = synthetic construct
SEQUENCE: 1
YGRKKRRQRR R                                                                11

SEQ ID NO: 2            moltype = AA  length = 19
FEATURE                 Location/Qualifiers
source                  1..19
                        mol_type = protein
                        organism = synthetic construct
SEQUENCE: 2
PKPRVTWNKK GKKVNSQRF                                                        19

SEQ ID NO: 3            moltype = AA  length = 14
FEATURE                 Location/Qualifiers
source                  1..14
                        mol_type = protein
                        organism = synthetic construct
SEQUENCE: 3
KFERQKILDQ RFFE                                                             14

SEQ ID NO: 4            moltype = AA  length = 46
FEATURE                 Location/Qualifiers
source                  1..46
                        mol_type = protein
                        organism = synthetic construct
SEQUENCE: 4
NYGRKKRRQR RRPKPRVTWN KKGKKVNSQR FKFERQKILD QRFFEC                          46

SEQ ID NO: 5            moltype = AA  length = 12
FEATURE                 Location/Qualifiers
source                  1..12
                        mol_type = protein
                        organism = synthetic construct
SEQUENCE: 5
YGRKKRRQRR RC                                                               12

SEQ ID NO: 6            moltype = AA  length = 13
FEATURE                 Location/Qualifiers
source                  1..13
                        mol_type = protein
                        organism = synthetic construct
SEQUENCE: 6
YGRKKRRQRR RGC                                                              13

SEQ ID NO: 7            moltype = AA  length = 13
FEATURE                 Location/Qualifiers
source                  1..13
                        mol_type = protein
                        organism = synthetic construct
SEQUENCE: 7
CAYGRKKRRQ RRR                                                              13

SEQ ID NO: 8            moltype = AA  length = 33
FEATURE                 Location/Qualifiers
source                  1..33
                        mol_type = protein
                        organism = synthetic construct
SEQUENCE: 8
YGRKKRRQRR RYGRKKRRQR RRYGRKKRRQ RRR                                        33

SEQ ID NO: 9            moltype = AA  length = 10
```

```
FEATURE                 Location/Qualifiers
source                  1..10
                        mol_type = protein
                        organism = synthetic construct
SEQUENCE: 9
GRKKRRQRRR                                                                      10

SEQ ID NO: 10           moltype = AA   length = 11
FEATURE                 Location/Qualifiers
source                  1..11
                        mol_type = protein
                        organism = synthetic construct
SEQUENCE: 10
GRKKRRQRRR G                                                                    11

SEQ ID NO: 11           moltype = AA   length = 12
FEATURE                 Location/Qualifiers
source                  1..12
                        mol_type = protein
                        organism = synthetic construct
SEQUENCE: 11
GRKKRRQRRR CG                                                                   12

SEQ ID NO: 12           moltype = AA   length = 12
FEATURE                 Location/Qualifiers
source                  1..12
                        mol_type = protein
                        organism = synthetic construct
SEQUENCE: 12
GRKKRRQRRR PP                                                                   12

SEQ ID NO: 13           moltype = AA   length = 13
FEATURE                 Location/Qualifiers
source                  1..13
                        mol_type = protein
                        organism = synthetic construct
SEQUENCE: 13
GRKKRRQRRR PPQ                                                                  13

SEQ ID NO: 14           moltype = AA   length = 14
FEATURE                 Location/Qualifiers
source                  1..14
                        mol_type = protein
                        organism = synthetic construct
SEQUENCE: 14
GRKKRRQRRR PPQC                                                                 14

SEQ ID NO: 15           moltype = AA   length = 9
FEATURE                 Location/Qualifiers
source                  1..9
                        mol_type = protein
                        organism = synthetic construct
SEQUENCE: 15
RKKRRQRRR                                                                       9

SEQ ID NO: 16           moltype = AA   length = 9
FEATURE                 Location/Qualifiers
source                  1..9
                        mol_type = protein
                        organism = synthetic construct
SEQUENCE: 16
RKKRRQRRR                                                                       9

SEQ ID NO: 17           moltype = AA   length = 9
FEATURE                 Location/Qualifiers
source                  1..9
                        mol_type = protein
                        organism = synthetic construct
SEQUENCE: 17
RRRQRRKKR                                                                       9

SEQ ID NO: 18           moltype = AA   length = 9
FEATURE                 Location/Qualifiers
source                  1..9
                        mol_type = protein
                        organism = synthetic construct
SEQUENCE: 18
RRRQRRKKR                                                                       9
```

-continued

| | | |
|---|---|---|
| SEQ ID NO: 19<br>FEATURE<br>source | moltype = AA   length = 13<br>Location/Qualifiers<br>1..13<br>mol_type = protein<br>organism = synthetic construct | |
| SEQUENCE: 19<br>GRRRRRRRR PPQ | | 13 |
| SEQ ID NO: 20<br>FEATURE<br>source | moltype = AA   length = 19<br>Location/Qualifiers<br>1..19<br>mol_type = protein<br>organism = synthetic construct | |
| SEQUENCE: 20<br>TRQARRNRRR RWRERQRGC | | 19 |
| SEQ ID NO: 21<br>FEATURE<br>source | moltype = AA   length = 15<br>Location/Qualifiers<br>1..15<br>mol_type = protein<br>organism = synthetic construct | |
| SEQUENCE: 21<br>TRRQRTRRAR RNRGC | | 15 |
| SEQ ID NO: 22<br>FEATURE<br>source | moltype = AA   length = 21<br>Location/Qualifiers<br>1..21<br>mol_type = protein<br>organism = synthetic construct | |
| SEQUENCE: 22<br>KLTRAQRRAA ARKNKRNTRG C | | 21 |
| SEQ ID NO: 23<br>FEATURE<br>source | moltype = AA   length = 15<br>Location/Qualifiers<br>1..15<br>mol_type = protein<br>organism = synthetic construct | |
| SEQUENCE: 23<br>RRRRNRTRRN RRRVR | | 15 |
| SEQ ID NO: 24<br>FEATURE<br>source | moltype = AA   length = 8<br>Location/Qualifiers<br>1..8<br>mol_type = protein<br>organism = synthetic construct | |
| SEQUENCE: 24<br>RRRRRRGC | | 8 |
| SEQ ID NO: 25<br>FEATURE<br>source | moltype = AA   length = 10<br>Location/Qualifiers<br>1..10<br>mol_type = protein<br>organism = synthetic construct | |
| SEQUENCE: 25<br>RRRRRRRRGC | | 10 |
| SEQ ID NO: 26<br>FEATURE<br>source | moltype = AA   length = 21<br>Location/Qualifiers<br>1..21<br>mol_type = protein<br>organism = synthetic construct | |
| SEQUENCE: 26<br>KETWWETWWT EWSQPKKKRK V | | 21 |
| SEQ ID NO: 27<br>FEATURE<br>source | moltype = AA   length = 16<br>Location/Qualifiers<br>1..16<br>mol_type = protein<br>organism = synthetic construct | |
| SEQUENCE: 27<br>RQILIWFQNR RMKWKK | | 16 |
| SEQ ID NO: 28<br>FEATURE<br>source | moltype = AA   length = 5<br>Location/Qualifiers<br>1..5<br>mol_type = protein<br>organism = synthetic construct | |
| SEQUENCE: 28<br>KFERQ | | 5 |

```
SEQ ID NO: 29            moltype = AA   length = 5
FEATURE                  Location/Qualifiers
source                   1..5
                         mol_type = protein
                         organism = synthetic construct SEQUENCE: 29
KFERQ                                                                     5

SEQ ID NO: 30            moltype = AA   length = 5
FEATURE                  Location/Qualifiers
source                   1..5
                         mol_type = protein
                         organism = synthetic construct SEQUENCE: 30
QKILD                                                                     5

SEQ ID NO: 31            moltype = AA   length = 5
FEATURE                  Location/Qualifiers
source                   1..5
                         mol_type = protein
                         organism = synthetic construct SEQUENCE: 31
QRFFE                                                                     5

SEQ ID NO: 32            moltype = AA   length = 9
FEATURE                  Location/Qualifiers
source                   1..9
                         mol_type = protein
                         organism = synthetic construct SEQUENCE: 32
KFERQKILD                                                                 9

SEQ ID NO: 33            moltype = AA   length = 10
FEATURE                  Location/Qualifiers
source                   1..10
                         mol_type = protein
                         organism = synthetic construct SEQUENCE: 33
QKILDQRFFE                                                               10

SEQ ID NO: 34            moltype = AA   length = 9
FEATURE                  Location/Qualifiers
source                   1..9
                         mol_type = protein
                         organism = synthetic construct SEQUENCE: 34
KFERQRFFE                                                                 9

SEQ ID NO: 35            moltype = AA   length = 7
FEATURE                  Location/Qualifiers
source                   1..7
                         mol_type = protein
                         organism = synthetic construct SEQUENCE: 35
QRFFERQ                                                                   7

SEQ ID NO: 36            moltype = AA   length = 7
FEATURE                  Location/Qualifiers
source                   1..7
                         mol_type = protein
                         organism = synthetic construct SEQUENCE: 36
QRKFERQ                                                                   7

SEQ ID NO: 37            moltype = AA   length = 5
FEATURE                  Location/Qualifiers
source                   1..5
                         mol_type = protein
                         organism = synthetic construct SEQUENCE: 37
KKGKK                                                                     5

SEQ ID NO: 38            moltype = AA   length = 7
FEATURE                  Location/Qualifiers
source                   1..7
                         mol_type = protein
                         organism = synthetic construct

SEQUENCE: 38
```

```
NKKGKKV                                                               7

SEQ ID NO: 39         moltype = AA  length = 9
FEATURE               Location/Qualifiers
source                1..9
                      mol_type = protein
                      organism = synthetic construct
SEQUENCE: 39
NKKGKKVNS                                                             9

SEQ ID NO: 40         moltype = AA  length = 11
FEATURE               Location/Qualifiers
source                1..11
                      mol_type = protein
                      organism = synthetic construct
SEQUENCE: 40
KKGKKVNSQR F                                                          11

SEQ ID NO: 41         moltype = AA  length = 15
FEATURE               Location/Qualifiers
source                1..15
                      mol_type = protein
                      organism = synthetic construct
SEQUENCE: 41
RVTWNKKGKK VNSQR                                                      15

SEQ ID NO: 42         moltype = AA  length = 20
FEATURE               Location/Qualifiers
source                1..20
                      mol_type = protein
                      organism = synthetic construct
SEQUENCE: 42
PKPRVTWNKK GKKVNSQRFE                                                 20

SEQ ID NO: 43         moltype = AA  length = 22
FEATURE               Location/Qualifiers
source                1..22
                      mol_type = protein
                      organism = synthetic construct
SEQUENCE: 43
TGDPKPRVTW NKKGKKVNSQ RF                                              22

SEQ ID NO: 44         moltype = AA  length = 23
FEATURE               Location/Qualifiers
source                1..23
                      mol_type = protein
                      organism = synthetic construct
SEQUENCE: 44
TGDPKPRVTW NKKGKKVNSQ RFE                                             23

SEQ ID NO: 45         moltype = AA  length = 19
FEATURE               Location/Qualifiers
source                1..19
                      mol_type = protein
                      organism = synthetic construct
SEQUENCE: 45
PKPRVTWNRK GKKVNSQRF                                                  19

SEQ ID NO: 46         moltype = AA  length = 19
FEATURE               Location/Qualifiers
source                1..19
                      mol_type = protein
                      organism = synthetic construct
SEQUENCE: 46
PKPRVTWNRR GKKVNSQRF                                                  19

SEQ ID NO: 47         moltype = AA  length = 19
FEATURE               Location/Qualifiers
source                1..19
                      mol_type = protein
                      organism = synthetic construct
SEQUENCE: 47
PKPRVTWNRR GRKVNSQRF                                                  19

SEQ ID NO: 48         moltype = AA  length = 19
FEATURE               Location/Qualifiers
source                1..19
                      mol_type = protein
                      organism = synthetic construct
```

```
SEQUENCE: 48
PKPRVTWNRR GRRVNSQRF                                                    19

SEQ ID NO: 49          moltype = AA   length = 19
FEATURE                Location/Qualifiers
source                 1..19
                       mol_type = protein
                       organism = synthetic construct
SEQUENCE: 49
PKPRVTWNKR GKKVNSQRF                                                    19

SEQ ID NO: 50          moltype = AA   length = 19
FEATURE                Location/Qualifiers
source                 1..19
                       mol_type = protein
                       organism = synthetic construct
SEQUENCE: 50
PKPRVTWNKR GRKVNSQRF                                                    19

SEQ ID NO: 51          moltype = AA   length = 19
FEATURE                Location/Qualifiers
source                 1..19
                       mol_type = protein
                       organism = synthetic construct
SEQUENCE: 51
PKPRVTWNKR GRRVNSQRF                                                    19

SEQ ID NO: 52          moltype = AA   length = 19
FEATURE                Location/Qualifiers
source                 1..19
                       mol_type = protein
                       organism = synthetic construct
SEQUENCE: 52
PKPRVTWNKK GRKVNSQRF                                                    19

SEQ ID NO: 53          moltype = AA   length = 19
FEATURE                Location/Qualifiers
source                 1..19
                       mol_type = protein
                       organism = synthetic construct
SEQUENCE: 53
PKPRVTWNKK GRRVNSQRF                                                    19

SEQ ID NO: 54          moltype = AA   length = 10
FEATURE                Location/Qualifiers
source                 1..10
                       mol_type = protein
                       organism = synthetic construct
SEQUENCE: 54
VQPYSTVVHS                                                              10

SEQ ID NO: 55          moltype = AA   length = 9
FEATURE                Location/Qualifiers
source                 1..9
                       mol_type = protein
                       organism = synthetic construct
SEQUENCE: 55
VQYSTVVHS                                                               9

SEQ ID NO: 56          moltype = AA   length = 10
FEATURE                Location/Qualifiers
source                 1..10
                       mol_type = protein
                       organism = synthetic construct
SEQUENCE: 56
VEPYSTVVHS                                                              10

SEQ ID NO: 57          moltype = AA   length = 9
FEATURE                Location/Qualifiers
source                 1..9
                       mol_type = protein
                       organism = synthetic construct
SEQUENCE: 57
VEYSTVVHS                                                               9

SEQ ID NO: 58          moltype = AA   length = 9
FEATURE                Location/Qualifiers
source                 1..9
                       mol_type = protein
```

```
                        -continued organism = synthetic construct
SEQUENCE: 58
VXPYXXVVX                                                               9

SEQ ID NO: 59           moltype = AA  length = 9
FEATURE                 Location/Qualifiers
source                  1..9
                        mol_type = protein
                        organism = synthetic construct
SEQUENCE: 59
VXPYXXLVX                                                               9

SEQ ID NO: 60           moltype = AA  length = 9
FEATURE                 Location/Qualifiers
source                  1..9
                        mol_type = protein
                        organism = synthetic construct
SEQUENCE: 60
VXPYXXVLX                                                               9

SEQ ID NO: 61           moltype = AA  length = 9
FEATURE                 Location/Qualifiers
source                  1..9
                        mol_type = protein
                        organism = synthetic construct
SEQUENCE: 61
LXPYXXVVX                                                               9

SEQ ID NO: 62           moltype = AA  length = 9
FEATURE                 Location/Qualifiers
source                  1..9
                        mol_type = protein
                        organism = synthetic construct
SEQUENCE: 62
VXPYXXLLX                                                               9

SEQ ID NO: 63           moltype = AA  length = 9
FEATURE                 Location/Qualifiers
source                  1..9
                        mol_type = protein
                        organism = synthetic construct
SEQUENCE: 63
LXPYXXVLX                                                               9

SEQ ID NO: 64           moltype = AA  length = 9
FEATURE                 Location/Qualifiers
source                  1..9
                        mol_type = protein
                        organism = synthetic construct
SEQUENCE: 64
LXPYXXLVX                                                               9

SEQ ID NO: 65           moltype = AA  length = 9
FEATURE                 Location/Qualifiers
source                  1..9
                        mol_type = protein
                        organism = synthetic construct
SEQUENCE: 65
LXPYXXLLX                                                               9

SEQ ID NO: 66           moltype = AA  length = 8
FEATURE                 Location/Qualifiers
source                  1..8
                        mol_type = protein
                        organism = synthetic construct
SEQUENCE: 66
VXYXXVVX                                                                8

SEQ ID NO: 67           moltype = AA  length = 8
FEATURE                 Location/Qualifiers
source                  1..8
                        mol_type = protein
                        organism = synthetic construct
SEQUENCE: 67
VXYXXLVX                                                                8

SEQ ID NO: 68           moltype = AA  length = 8
FEATURE                 Location/Qualifiers
source                  1..8
```

```
                                mol_type = protein
                                organism = synthetic construct
SEQUENCE: 68
VXYXXVLX                                                                               8

SEQ ID NO: 69                   moltype = AA  length = 8
FEATURE                         Location/Qualifiers
source                          1..8
                                mol_type = protein
                                organism = synthetic construct
SEQUENCE: 69
LXYXXVVX                                                                               8

SEQ ID NO: 70                   moltype = AA  length = 8
FEATURE                         Location/Qualifiers
source                          1..8
                                mol_type = protein
                                organism = synthetic construct
SEQUENCE: 70
VXYXXLLX                                                                               8

SEQ ID NO: 71                   moltype = AA  length = 8
FEATURE                         Location/Qualifiers
source                          1..8
                                mol_type = protein
                                organism = synthetic construct
SEQUENCE: 71
LXYXXVLX                                                                               8

SEQ ID NO: 72                   moltype = AA  length = 8
FEATURE                         Location/Qualifiers
source                          1..8
                                mol_type = protein
                                organism = synthetic construct
SEQUENCE: 72
LXYXXLVX                                                                               8

SEQ ID NO: 73                   moltype = AA  length = 8
FEATURE                         Location/Qualifiers
source                          1..8
                                mol_type = protein
                                organism = synthetic construct
SEQUENCE: 73
LXYXXLLX                                                                               8

SEQ ID NO: 74                   moltype = AA  length = 10
FEATURE                         Location/Qualifiers
source                          1..10
                                mol_type = protein
                                organism = synthetic construct
SEQUENCE: 74
VXPYXXVVXS                                                                            10

SEQ ID NO: 75                   moltype = AA  length = 10
FEATURE                         Location/Qualifiers
source                          1..10
                                mol_type = protein
                                organism = synthetic construct
SEQUENCE: 75
VXPYXXLVXS                                                                            10

SEQ ID NO: 76                   moltype = AA  length = 10
FEATURE                         Location/Qualifiers
source                          1..10
                                mol_type = protein
                                organism = synthetic construct
SEQUENCE: 76
VXPYXXVLXS                                                                            10

SEQ ID NO: 77                   moltype = AA  length = 10
FEATURE                         Location/Qualifiers
source                          1..10
                                mol_type = protein
                                organism = synthetic construct
SEQUENCE: 77
LXPYXXVVXS                                                                            10

SEQ ID NO: 78                   moltype = AA  length = 10
FEATURE                         Location/Qualifiers
```

| | | |
|---|---|---|
| source | 1..10<br>mol_type = protein<br>organism = synthetic construct | |
| SEQUENCE: 78<br>VXPYXXLLXS | | 10 |
| SEQ ID NO: 79<br>FEATURE<br>source | moltype = AA   length = 10<br>Location/Qualifiers<br>1..10<br>mol_type = protein<br>organism = synthetic construct | |
| SEQUENCE: 79<br>LXPYXXVLXS | | 10 |
| SEQ ID NO: 80<br>FEATURE<br>source | moltype = AA   length = 10<br>Location/Qualifiers<br>1..10<br>mol_type = protein<br>organism = synthetic construct | |
| SEQUENCE: 80<br>LXPYXXLVXS | | 10 |
| SEQ ID NO: 81<br>FEATURE<br>source | moltype = AA   length = 10<br>Location/Qualifiers<br>1..10<br>mol_type = protein<br>organism = synthetic construct | |
| SEQUENCE: 81<br>LXPYXXLLXS | | 10 |
| SEQ ID NO: 82<br>FEATURE<br>source | moltype = AA   length = 16<br>Location/Qualifiers<br>1..16<br>mol_type = protein<br>organism = synthetic construct | |
| SEQUENCE: 82<br>STASTVEPYS TVVHSG | | 16 |
| SEQ ID NO: 83<br>FEATURE<br>source | moltype = AA   length = 15<br>Location/Qualifiers<br>1..15<br>mol_type = protein<br>organism = synthetic construct | |
| SEQUENCE: 83<br>STASTVEPYS TVVHS | | 15 |
| SEQ ID NO: 84<br>FEATURE<br>source | moltype = AA   length = 14<br>Location/Qualifiers<br>1..14<br>mol_type = protein<br>organism = synthetic construct | |
| SEQUENCE: 84<br>STASTVQPYS TVVH | | 14 |
| SEQ ID NO: 85<br>FEATURE<br>source | moltype = AA   length = 13<br>Location/Qualifiers<br>1..13<br>mol_type = protein<br>organism = synthetic construct | |
| SEQUENCE: 85<br>STASTVQPYS TVV | | 13 |
| SEQ ID NO: 86<br>FEATURE<br>source | moltype = AA   length = 16<br>Location/Qualifiers<br>1..16<br>mol_type = protein<br>organism = synthetic construct | |
| SEQUENCE: 86<br>STASTVQPYS TVVHSG | | 16 |
| SEQ ID NO: 87<br>FEATURE<br>source | moltype = AA   length = 15<br>Location/Qualifiers<br>1..15<br>mol_type = protein<br>organism = synthetic construct | |
| SEQUENCE: 87<br>STASTVQPYS TVVHS | | 15 |
| SEQ ID NO: 88 | moltype = AA   length = 14 | |

```
FEATURE              Location/Qualifiers
source               1..14
                     mol_type = protein
                     organism = synthetic construct
SEQUENCE: 88
STASTVQPYS TVVH                                                              14

SEQ ID NO: 89        moltype = AA  length = 13
FEATURE              Location/Qualifiers
source               1..13
                     mol_type = protein
                     organism = synthetic construct
SEQUENCE: 89
STASTVQPYS TVV                                                               13

SEQ ID NO: 90        moltype = AA  length = 35
FEATURE              Location/Qualifiers
source               1..35
                     mol_type = protein
                     organism = synthetic construct
SEQUENCE: 90
YGRKKRRQRR RVQPYSTVVH SKFERQKILD QRFFE                                       35
```